(12) United States Patent
Katsumata et al.

(10) Patent No.: US 8,798,931 B2
(45) Date of Patent: Aug. 5, 2014

(54) EVALUATION METHOD FOR EVALUATING A STATE OF A PHOTOSYNTHESIS SAMPLE

(75) Inventors: Masakazu Katsumata, Hamamatsu (JP); Ryosuke Mochizuki, Hamamatsu (JP); Hiroshi Satozono, Hamamatsu (JP); Kimiko Kazumura, Hamamatsu (JP); Ayano Takeuchi, Hamamatsu (JP)

(73) Assignee: Hamamatsu Photonics KK., Hamamatsu-shi, Shizuoka (JP)

( * ) Notice: Subject to any disclaimer, the term of this patent is extended or adjusted under 35 U.S.C. 154(b) by 1519 days.

(21) Appl. No.: 12/279,789

(22) PCT Filed: Feb. 20, 2007

(86) PCT No.: PCT/JP2007/053103
§ 371 (c)(1),
(2), (4) Date: Feb. 20, 2009

(87) PCT Pub. No.: WO2007/097341
PCT Pub. Date: Aug. 30, 2007

(65) Prior Publication Data
US 2010/0159496 A1    Jun. 24, 2010

(30) Foreign Application Priority Data

Feb. 20, 2006 (JP) ............... P2006-042787
Nov. 7, 2006 (JP) ............... P2006-301850

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC ............ 702/19; 702/22; 703/11; 703/12

(58) Field of Classification Search
CPC ............... G01N 2021/635; G01N 21/6408; G01N 21/6486
See application file for complete search history.

(56) References Cited

U.S. PATENT DOCUMENTS 4,650,336 A  3/1987  Moll
4,942,303 A  7/1990  Kolber et al.
(Continued)

FOREIGN PATENT DOCUMENTS

DE    248 433 A1    8/1987
DE    199 10 436 A1   10/2000
(Continued)

OTHER PUBLICATIONS

Schneckenburger et al. (Radiat. Environ. Biophys. (1992, 31, 73-81).*

(Continued)

*Primary Examiner* — Larry D Riggs, II
(74) *Attorney, Agent, or Firm* — Drinker Biddle & Reath LLP

(57) ABSTRACT

An object of the present invention is to appropriately and easily evaluate a photosynthetic function of a photosynthetic sample contained in an evaluation sample.
An evaluation method for photosynthetic sample according to the present invention is for evaluating a state of a photosynthetic sample with a photosynthetic function based on temporal data of a luminescence amount of delayed luminescence emitted from the photosynthetic sample. First, characteristic values that indicate characteristics are determined for a plurality of time periods in the temporal data. An evaluation value is then computed by weighting the characteristic values. The state of the photosynthetic sample is then evaluated based on the evaluation value.

18 Claims, 44 Drawing Sheets

(56) References Cited

U.S. PATENT DOCUMENTS 5,854,063 A 12/1998 Li et al.
2005/0072935 A1 4/2005 Lussier

FOREIGN PATENT DOCUMENTS

| JP | 2003-501615 | 1/2003 |
|---|---|---|
| JP | 2004-101196 A | 4/2004 |
| JP | 2004-309458 | 11/2004 |
| WO | WO 2005/062027 | 7/2005 |

OTHER PUBLICATIONS

Fernandes et al. (Analytical Biochemistry, 2002, 307, 1-12).*
A. Dobek et al., "The First Events of Protochlorophyll (IDE) Photoreduction investigated in Etiolated Leaves by Means of the Fluorescence Excited by Short, 610 nm Laser Flashes at Room Temperature," Photobiochemistry and Photophysics, Elsevier Science Publishers B.V., Amsterdam, NL, vol. 2, No. 1-2, ISSN: 0165-8646, Mar. 1, 1981, pp. 35-44, XP009145914.
J. Xiong et al., Loss of Inhibition by formate in newly constructed photosystem II D1 mutants, D1-R257E and D1-R257M, of *Chlamydomonas reinhardtii*, Biochimica et Biophysica ACTA. Bioenergetics, Amsterdam, NL, vol. 1365, No. 3, ISSN: 0005-2728, DOI: DOI: 10.1016/S0005-2728(98)00101-7, Jul. 20, 1998, pp. 473-491, XP004338702.
B. R. Velthuys, "Binding of the Inhibitor $NH_3$ to the Oxygen-Evolving Apparatus of Spinach Chloroplasts", Biochimica et Biophysica Acta. Bioenergetics, Amsterdam, NL, vol. 396, No. 3, ISSN: 0005-2728, DOI: DOI:10.1016/0005-2728(75)90145-0, Sep. 8, 1975, pp. 392-401, XP025502570.
P. Haldimann et al., "Non-photochemical quenching of chlorophyll a fluorescence by oxidised plastoquinone: new evidences based on modulation of the redox state of the endogenous plastoquinone pool in broken spinach chloroplasts," Biochimica et Biophysica Acta. Bioenergetics, Amsterdam, NL, vol. 1706, No. 3, ISSN: 0005-2728, DOI: DOI:10.1016/J.BBABIO.2004.11.005, Feb. 17, 2005, pp. 239-249, XP004896573.
J. Bürger et al., "Long term delayed luminescence: A possible fast and convenient assay for nutrition deficiencies and environmental pollution damages in plants," Plant and Soil, vol. 109, No. 1, 1988, pp. 79-83.
Gulotty et al., "Low-Intensity Picosecond Fluorescence Kinetics and Excitation Dynamics in Barley Chloroplasts," Biochimica et Biophysica Acta, No. 682, 1982, pp. 322-331.
Xu et al., "Ulrafast spectroscopy studies on the mechanism of electron transfer and energy conversion in the isolated pseudo ginseng, water hyacinth and spinach chloroplasts," Science in China, vol. 44, No. 4, Aug. 2001, pp. 366-380.
Goltsev et al., "Kinetics of delayed chlorophyll α fluorescence registered in milliseconds time range," Photoshythesis Research, No. 84, 2005, pp. 209-215.
Ruth, "The fluorescence Pulse Method as a Tool to Characterize the Photosynthetic System of Plants and Algae," Geoscience and Remote Sensing Symposium, 1994, vol. 1, Aug. 8, 1994, pp. 646-648.
G. Kretsch et al., "Numerical analysis of delayed fluorescence kinetics of algae," E. Schweizerbart'sche Verlagsbuchhandlung, 1987, vol. 29, pp. 47-54 (with Abstract).
H. Krause et al., "Differential Equations for Delayed Fluorescence Kinetics in Living Plants," Journal of Luminescence, vols. 31 & 32, 1984, pp. 885-887.
W. Schmidt et al., "Long-term delayed luminescence in *Scenedesmus obliquus*. II. Influence of exogeneous factors," Biochimico et Biophysica Acta, vol. 891, 1987, pp. 22-27.
Y. Yan et al., "Further analysis of delayed luminescence of plants," Journal of Photochemistry and Photobiology B: Biology, vol. 78, 2005, pp. 234-244.
M. Katsumata et al., "Influences of Herbicides and Mercury on Blue-Green Alga *Spirulina platensis*—Analysis of Long-Term Behavior of *S. platensis* Delayed Fluorescence," Journal of Japan Society on Water Environment, vol. 28, No. 1, Jan. 10, 2005, pp. 23-28.
M. Katsumata et al., "Application of Delayed Luminescence for Algal Bioassay: Determination of Influences of Chemical Substance on Alga." Environmental Research Quarterly, No. 139, Dec. 20, 2005, pp. 107-112.
Office Action with double patenting rejection dated Apr. 3, 2014 in U.S. Appl. No. 10/583,128.

* cited by examiner

*Fig.15*
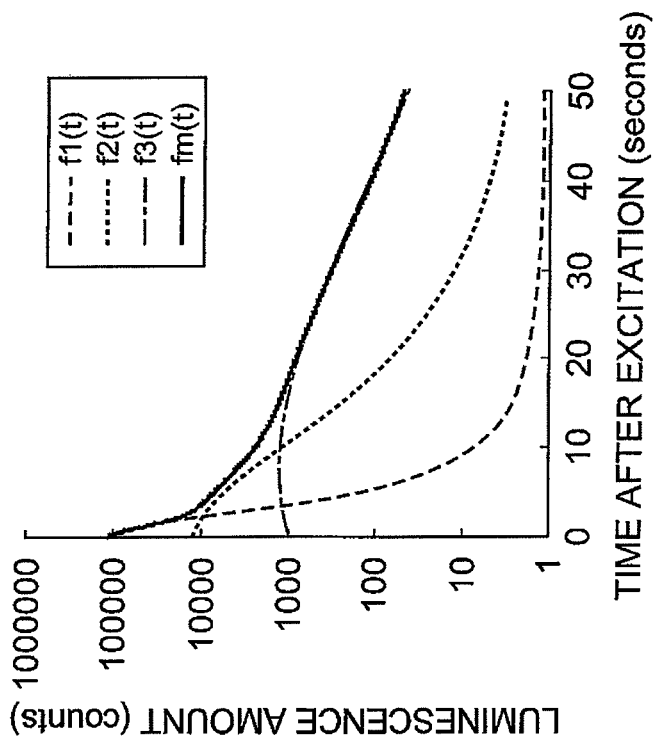
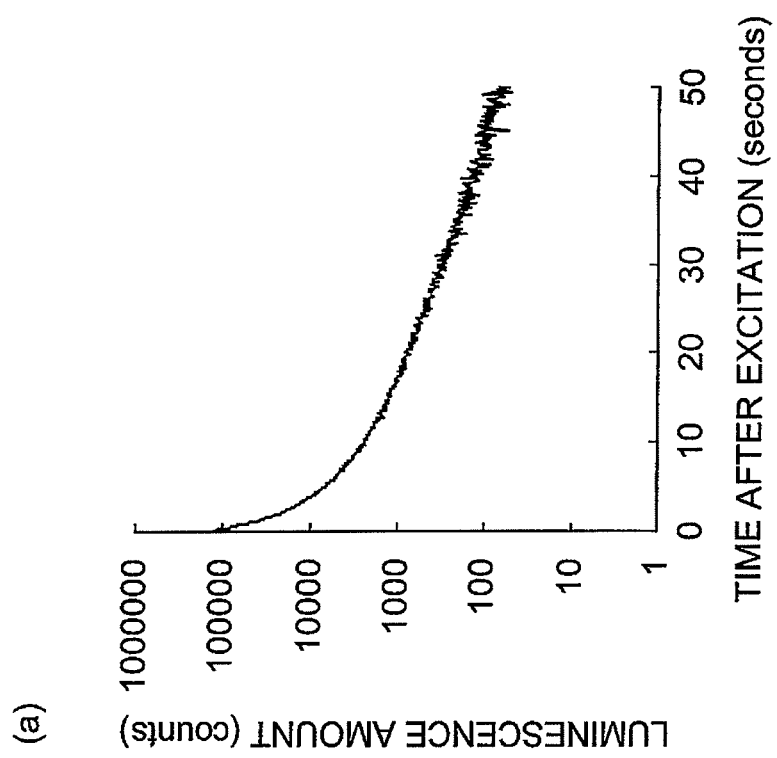

*Fig.32*
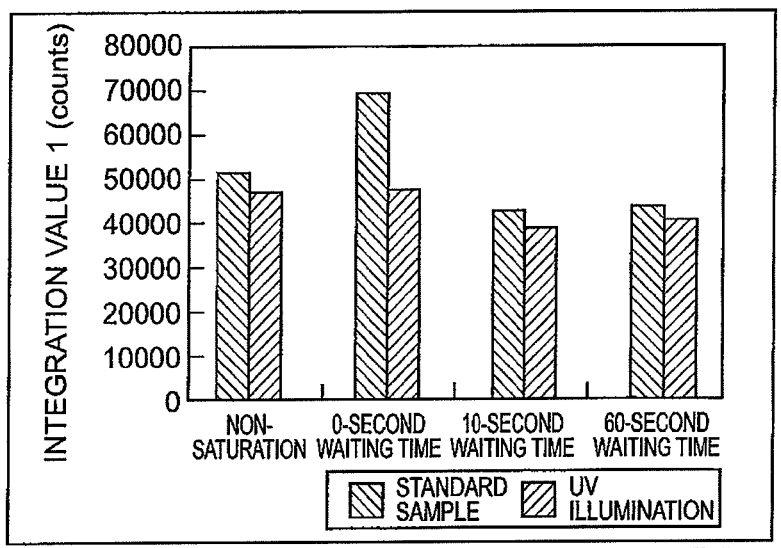
(a)
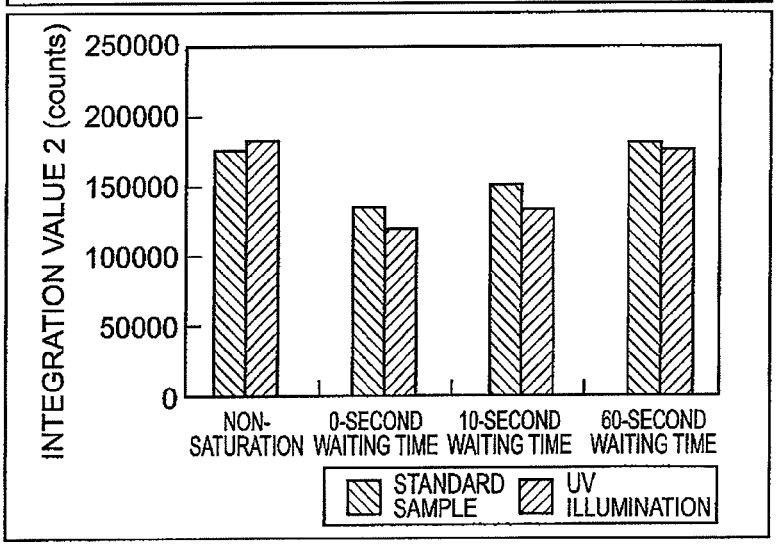
(b)
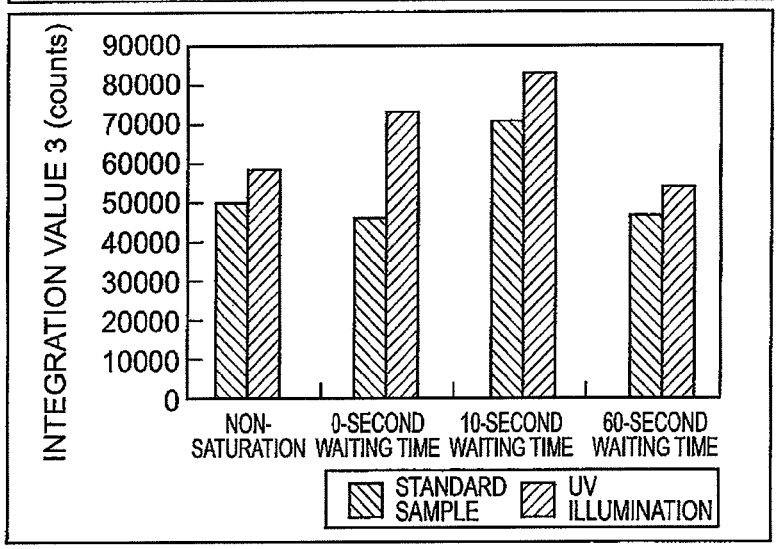
(c)

Fig.42

|  | eII | vII | |
|---|---|---|---|
|  |  | 0-SECOND TO 10-SECOND WAITING | 0-SECOND TO 60-SECOND WAITING |
| STANDARD SAMPLE | 100 | 100 | 100 |
| DCMU-EXPOSED SAMPLE | 188 | -31 | -45 |
| DBMIB-EXPOSED SAMPLE | 163 | 27 | 13 |
| Ant-A EXPOSED SAMPLE | 106 | -1 | 98 |

Fig.43

|  | vQ | %oQ | |
|---|---|---|---|
|  |  | 10-SECOND WAITING | 60-SECOND WAITING |
| STANDARD SAMPLE | 100 | 36 | 107 |
| DCMU-EXPOSED SAMPLE | 61 | 16 | 61 |
| DBMIB-EXPOSED SAMPLE | 30 | 4 | 22 |
| Ant-A EXPOSED SAMPLE | 132 | 75 | 129 |

*Fig.44*

|  | eI | cI | | |
|---|---|---|---|---|
|  |  | 0-SECOND WAITING | 10-SECOND WAITING | 60-SECOND WAITING |
| STANDARD SAMPLE | 100 | -6 | 38 | -5 |
| DCMU-EXPOSED SAMPLE | 40 | 56 | 74 | 13 |
| DBMIB-EXPOSED SAMPLE | 99 | -9 | 17 | 8 |
| Ant-A EXPOSED SAMPLE | 89 | -19 | -12 | 0 |

EVALUATION METHOD FOR EVALUATING A STATE OF A PHOTOSYNTHESIS SAMPLE

TECHNICAL FIELD

The present invention relates to an evaluation method for photosynthetic sample, an evaluation system for photosynthetic sample, and an evaluation program for photosynthetic sample.

BACKGROUND ART

As a conventional method for evaluating a photosynthetic sample contained in an evaluation sample (methods for evaluating a degree of impact of an environmental factor (such as a chemical substance) having impact on growth of a living organism, etc.), there is a method for ecological risk evaluation of a chemical substance, with which an evaluation is made using growth of cells of a plant, algae, or other plant origin. A most general type of such an evaluation method is an algae growth inhibition test, which is a bioassay for ecological risk evaluation of a chemical substance. The algae growth inhibition test is conducted in accordance with guidelines of the Organization of Economic Co-operation and Development (OECD). In the algae growth inhibition test, algae is cultured for 72 hours in a state of being exposed to a chemical substance and growth inhibition is measured to evaluate harmful properties of the chemical substance.

However, with the algae growth inhibition test, because a growth ability of a living organism is subject to testing, operations are complicated and a long time of 72 hours is required to obtain test results. Meanwhile, there is, for example, a method such as described in Patent Document 1 where a delayed luminescence, emitted from an algae, is measured to evaluate an environmental impact of a chemical substance. Delayed luminescence is phenomenon where, upon illumination of light on a living organism with a photosynthetic function, emission of fluorescence occurs from a photosynthetic pigment due to energy of the light. By this method, an environmental impact of a chemical substance can be evaluated in a short time.

Also, in Non-Patent Documents 1 and 2 is described a derivation of a luminescence model equation from reaction equations of a photosynthetic electron transport system for describing emission of delayed luminescence from a photosystem II, a plastoquinone pool, and a photosystem I, which are principal reaction sites of the photosynthetic electron transport system. The model equation is constituted of a plurality of exponential functions. These non-patent documents disclose that the model equation exhibits a shape close to experimental results.

A luminescence model equation, constituted of a plurality of exponential functions, is also disclosed in Non-Patent Document 3. It is also described here that by substituting suitable factors into the model equation, variations similar to experimental results are obtained.

Patent Document 1: International Patent Publication No. 2005/062027 Pamphlet
Non-Patent Document 1: Von G. Kretsch and V. Gerhardt, "Numerical analysis of delayed fluorescence kinetics of algae," F. Schweizerbart'sche Verlagsbuchhandlung, 1987, 29, pp. 47-54.
Non-Patent Document 2: Hans Krause, Gerd Kretsch, and Volkmar Gerhardt, "DIFFERENTIAL EQUATIONS FOR DELAYED FLUORESCENCE KINETICS IN LIVING PLANTS," Journal of Luminescence, Elsevier Science Publishers B. V., 1984, 31 & 32 (1984), pp. 885-887.
Non-Patent Document 3: Werner Schmidt and Horst Senger, "Long-term delayed luminescence in Scenesdesmus obliquus II Influence of exogenous factors," Biochimica et Biophysica Acta, Elsevier Science Publishers, 1987, 891 (1987), pp. 22-27.

DISCLOSURE OF THE INVENTION

Problem to be Solved by the Invention

With the method described in Patent Document 1, an algae or other plant sample having a photosynthetic function is exposed to a chemical substance and a temporal variation of a luminescence amount of delayed luminescence emitted from the plant sample is measured. A shape and a characteristic point of a decay curve of the delayed luminescence are then noted and a change due to exposure to the chemical substance is evaluated to evaluate an environmental impact of the chemical substance. With this evaluation method, although setting (by an inspector) of the characteristic point of change of the decay curve is important, because the setting of the characteristic point is arbitrary, there are infinite possibilities. In a case where the setting of the characteristic point is not adequate or appropriate, the change cannot be detected. If the number of characteristic points is increased, the number of evaluation elements increases and analysis becomes complicated. Although a method by which an environmental impact of a chemical substance can be evaluated more appropriately and easily is thus demanded, this demand cannot be answered even using the methods described in Non-Patent Documents 1 to 3.

An object of the present invention is to resolve the above issues by providing an evaluation method for photosynthetic sample, an evaluation system for photosynthetic sample, and an evaluation program for photosynthetic sample by which a photosynthetic function of a photosynthetic sample contained in an evaluation sample can be evaluated appropriately and yet easily.

Means for Solving the Problem

An evaluation method for photosynthetic sample according to the present invention is a method for evaluating a state of a photosynthetic sample with a photosynthetic function based on temporal data of a luminescence amount of delayed luminescence emitted from the photosynthetic sample and includes: a characteristic value computing step of computing, for a plurality of time periods in the temporal data, characteristic values that indicate characteristics; an evaluation value computing step of computing an evaluation value by weighting the characteristic values; and an evaluation step of evaluating the state of the photosynthetic sample based on the evaluation value.

An evaluation system for photosynthetic sample according to the present invention evaluates a state of a photosynthetic sample with a photosynthetic function based on temporal data of a luminescence amount of delayed luminescence emitted from the photosynthetic sample and includes: a characteristic value computing unit, computing, for a plurality of time periods in the temporal data, characteristic values that indicate characteristics; an evaluation value computing unit, computing an evaluation value by weighting the characteristic values; and an evaluating unit, evaluating the state of the photosynthetic sample based on the evaluation value.

An evaluation program for photosynthetic sample according to the present invention is a program for making a computer evaluate a state of a photosynthetic sample with a photosynthetic function based on temporal data of a luminescence amount of delayed luminescence emitted from the photosynthetic sample and includes: a characteristic value computing process of computing, for a plurality of time periods in the temporal data, characteristic values that indicate characteristics; an evaluation value computing process of computing an evaluation value by weighting the characteristic values; and an evaluating process of evaluating the state of the photosynthetic sample based on the evaluation value.

With the evaluation method for photosynthetic sample, the evaluation system for photosynthetic sample, and the evaluation program for photosynthetic sample, the characteristic values that indicate characteristics are computed for the plurality of time periods in the temporal data of the luminescence amount of delayed luminescence emitted from the photosynthetic sample, and the computed characteristic values are weighted. Then based on the computed evaluation value, the state of the photosynthetic sample is evaluated. It thus becomes possible to employ just the characteristic values effective for evaluation and consequently, a photosynthetic function of a photosynthetic sample contained in an evaluation sample can be evaluated appropriately and easily.

In the evaluation method for photosynthetic sample according to the present invention, preferably the characteristic value computing step includes a fitting step of determining, as the characteristic values, coefficient values of a plurality of priorly set functions so that the temporal data are fitted as a sum of the priorly set functions, and in the evaluation value computing step, the evaluation value is computed based on the coefficient values determined in the fitting step.

In the evaluation system for photosynthetic sample according to the present invention, preferably the characteristic value computing unit includes a fitting unit, determining, as the characteristic values, coefficient values of a plurality of priorly set functions so that the temporal data are fitted as a sum of the functions, and the evaluation value computing unit computes the evaluation value based on the coefficient values determined by the fitting unit.

In the evaluation program for photosynthetic sample according to the present invention, preferably the characteristic value computing process includes a fitting process of determining, as the characteristic values, coefficient values of a plurality of priorly set functions, so that the temporal data are fitted as a sum of the priorly set functions, and in the evaluation value computing process, the evaluation value is computed based on the coefficient values determined in the fitting process.

In these cases, evaluation is performed based on the coefficient values of the priorly set functions determined so that the sum of the functions fit the temporal data of the luminescence amount of delayed luminescence. Objective and mechanical evaluation in accordance with the functions is thus enabled. Also because the temporal data of the luminescence amount of delayed luminescence are fitted to the sum of the plurality of functions, an evaluation based on a mechanism of the delayed luminescence is enabled. Thus by the evaluation method for photosynthetic sample according to the present invention, the photosynthetic function of a photosynthetic sample contained in an evaluation sample can be evaluated appropriately and yet easily.

Preferably with the evaluation method for photosynthetic sample according to the present invention, the evaluation value computed in the evaluation value computing step is an area value computed based on the coefficient values of at least one function among the plurality of functions. By this configuration, the evaluation can be performed more easily.

Preferably with the evaluation method for photosynthetic sample according to the present invention, the functions are hill-shaped functions. With this configuration, fitting that is close to a mechanism of delayed luminescence is enabled to enable an even more appropriate evaluation to be made.

Preferably with the evaluation method for photosynthetic sample according to the present invention, the functions are Lorenz functions. With this configuration, an evaluation can made reliably with the specific evaluation basis.

Preferably with the evaluation method for photosynthetic sample according to the present invention, when $a_i$, $b_i$, and $c_i$ (i=1, 2, 3) are the coefficient values of the plurality of functions and t is a variable indicating an elapsed time from a base time, the functions are respectively expressed as:

$$10^{\frac{c_1}{1+a_1(t-b_1)^2}},$$
$$10^{\frac{c_2}{1+a_2(t-b_2)^2}},$$
$$10^{\frac{c_3}{1+a_3(t-b_3)^2}}$$

[Mathematical Formula 1]

With this configuration, an evaluation can be made reliably with the specific evaluation basis.

Preferably with the evaluation method for photosynthetic sample according to the present invention, the evaluation value computed in the evaluation value computing step is computed based on a computational formula containing coefficients of at least two or more functions among the plurality of functions. With this configuration, an evaluation that takes the mechanism of delayed luminescence into consideration can be made.

Preferably with the evaluation method for photosynthetic sample according to the present invention, when $a_i$, $b_i$, and $c_i$ (i=1, 2, 3) are the coefficient values of the plurality of functions, t is a variable indicating an elapsed time from a base time, and $b_1 < b_2 < b_3$, the functions are respectively expressed as:

$$10^{\frac{c_1}{1+a_1(t-b_1)^2}},$$
$$10^{\frac{c_2}{1+a_2(t-b_2)^2}},$$
$$10^{\frac{c_3}{1+a_3(t-b_3)^2}}$$

[Mathematical Formula 2]

and when $m_j$ (j=1 to 9) are constants, the evaluation value is computed by the following formula:

Evaluation value=$(m_1 \cdot a_3 \times m_2 \cdot b_3 \times m_3 \cdot c_3)/(m_4 \cdot a_2 \times m_5 \cdot b_2 \times m_6 \cdot c_2)/(m_7 \cdot a_1 \times m_8 \cdot b_1 \times m_9 \cdot c_1)$   [Mathematical Formula 3]

With this configuration, an evaluation can be made reliably with the specific evaluation basis.

The evaluation method for photosynthetic sample according to the present invention preferably further includes a measuring step of measuring the luminescence amount with time of the delayed luminescence emitted from the photosynthetic sample and making the measurement data the temporal data.

Also the evaluation system for photosynthetic sample according to the present invention preferably further includes a measuring unit, measuring the luminescence amount with time of the delayed luminescence emitted from the photosynthetic sample and making the measurement data the temporal data.

Also the evaluation program for photosynthetic sample according to the present invention preferably further includes a measuring process of measuring the luminescence amount with time of the delayed luminescence emitted from the photosynthetic sample and making the measurement data the temporal data.

With these configurations, an evaluation can be made from actually measured data and a more appropriate evaluation can be made.

The evaluation system for photosynthetic sample according to the present invention preferably further includes a light source controller, controlling a light source so as to illuminate excitation light onto the photosynthetic sample while changing illumination conditions. In this case, by controlling the light source inside the system, the illumination condition can be changed more easily.

Preferably with the evaluation method for photosynthetic sample according to the present invention, the measuring step includes: a first excitation step of illuminating a first excitation light onto the photosynthetic sample under a predetermined first illumination condition; and a second excitation step of illuminating, after the first excitation step, a second excitation light onto the photosynthetic sample under a second illumination condition that is less in light energy integration value than the first illumination condition; and in the characteristic value computing step, the characteristic values are computed based on temporal data obtained after the second excitation step.

Preferably with the evaluation program for photosynthetic sample according to the present invention, the measuring process includes: a first excitation process of illuminating a first excitation light onto the photosynthetic sample under a predetermined first illumination condition; and a second excitation process of illuminating, after the first excitation process, a second excitation light onto the photosynthetic sample under a second illumination condition that is less in light energy integration value than the first illumination condition; and in the characteristic value computing process, the characteristic values are computed based on temporal data obtained after the second excitation process.

In these cases, first, the first excitation light is illuminated onto the evaluation sample. Thereafter, the evaluation sample is illuminated with the second excitation light under the second illumination condition set so as to be lower in light energy integration value than the first excitation light. When illumination of the second excitation light ends, the luminescence amount of delayed luminescence from the evaluation sample is measured. The conditions for measuring the luminescence amount of delayed luminescence can thus be made fixed and consequently, the luminescence amount of delayed luminescence can be measured with high precision. The energy integration value is the light energy integration value of the photosynthetic sample.

Preferably with the evaluation method for photosynthetic sample according to the present invention, in the measuring step, a plurality of sets of temporal data are acquired by repeatedly measuring the luminescence amount a plurality of times with the second illumination condition being changed.

Preferably with the evaluation program for photosynthetic sample according to the present invention, in the measuring process, a plurality of sets of temporal data are acquired by repeatedly measuring the luminescence amount a plurality of times with the second illumination condition being changed.

In these cases, the processes from the illumination of the first excitation light to the measurement of the luminescence amount of delayed luminescence are repeated a plurality of times while changing the second illumination condition. An evaluation value corresponding to each measured luminescence amount is derived, and the evaluation sample is evaluated based on the evaluation value. By thus performing measurement of the luminescence amount of delayed luminescence a plurality of times while changing the second illumination condition within a comparatively short time, it becomes possible to appropriately evaluate a photosynthetic function of a photosynthetic sample contained in an evaluation sample without being influenced by external factors.

Preferably with the evaluation method for photosynthetic sample according to the present invention, the second illumination condition is a waiting time from an illumination ending time of the first excitation light to an illumination starting time of the second excitation light.

In this case, the processes from the illumination of the first excitation light to the measurement of the luminescence amount of delayed luminescence are performed with the illumination starting timing of the second excitation light being changed. The point at which the illumination of the second excitation light is started (the duration of the waiting time) is closely related to changes of a redox state of a photosynthetic sample. Thus by deriving the evaluation values based on the delayed luminescence amounts obtained by changing the illumination starting timing of the second excitation light, it becomes possible to appropriately evaluate a photosynthetic function of the photosynthetic sample contained in an evaluation sample. Also because it suffices to change the waiting time for changing the second illumination condition and the excitation light itself does not have to be changed, situations in which the redox state of the photosynthetic sample differs can be set readily.

Preferably with the evaluation method for photosynthetic sample according to the present invention, the second illumination condition is at least one condition selected from the group consisting of a light amount, wavelength, pulse width, and illumination duration of the second excitation light.

In this case, the processes from the illumination of the first excitation light to the measurement of the luminescence amount of delayed luminescence are performed while changing at least one condition selected from the group consisting of the light amount, wavelength, pulse width, and illumination duration of the second excitation light. These conditions that are changed are closely related to changes of a redox state of a photosynthetic sample. Thus by deriving the evaluation values based on the delayed luminescence amounts obtained by changing at least one of these factors, it becomes possible to appropriately evaluate a photosynthetic function of the photosynthetic sample contained in an evaluation sample.

Preferably with the evaluation method for photosynthetic sample according to the present invention, the evaluation step includes a comparing step of comparing the evaluation value computed in the evaluation value computing step and reference data on the evaluation value. With this configuration, by setting the evaluation value suited for evaluation and comparing it with the reference data, evaluation can be made more clearly.

The evaluation method for photosynthetic sample according to the present invention preferably further includes a reference data generating step of measuring the luminescence amount with time of a delayed luminescence emitted from a second photosynthetic sample and deriving, from the measurement data, the reference data used in the comparing step. With this configuration, evaluation based on measured data can be made in regard to the reference data as well and thus a more appropriate evaluation can be made.

Preferably with the evaluation method for photosynthetic sample according to the present invention, the characteristic value is an integration value determined by performing integration according to each time period.

In this case, the integration value of the luminescence amount of delayed luminescence is computed for a certain measurement time period and the evaluation is derived based on the integration value. By using the integration value, a redox state of a photosynthetic sample in the measurement time period, appearing in the temporal variation of the delayed luminescence amount, can be extracted easily and appropriately. Consequently, it becomes possible to appropriately evaluate a photosynthetic function of the photosynthetic sample contained in an evaluation sample. Also, in the case where a plurality of measurement time periods are configured and the integration values are computed for the respective time periods, it becomes possible to appropriately ascertain the temporal variation of the luminescence amount of delayed luminescence. It thus becomes possible to use a temporal variation across the plurality of measurement time periods to appropriately evaluate the photosynthetic function of the photosynthetic sample contained in the evaluation sample.

Preferably with the evaluation method for photosynthetic sample according to the present invention, in the evaluation step, an environmental factor to which the photosynthetic sample is subjected is evaluated.

Preferably with the evaluation system for photosynthetic sample according to the present invention, the evaluating unit evaluates an environmental factor to which the photosynthetic sample is subjected.

Preferably with the evaluation program for photosynthetic sample according to the present invention, in the evaluating process, an environmental factor to which the photosynthetic sample is subjected is evaluated.

In these cases, it becomes possible to appropriately evaluate an impact that an environmental factor applies to the photosynthetic sample in the evaluation sample.

Preferably with the evaluation method for photosynthetic sample according to the present invention the environmental factor is a plant cell growth inhibiting substance. With this configuration, a growth inhibition degree or other degree of harmfulness of the plant cell growth inhibiting substance can be evaluated.

Effect(S) of the Invention

With the present invention, a photosynthetic function of a photosynthetic sample contained in an evaluation sample can be evaluated appropriately and easily.

BRIEF DESCRIPTION OF THE DRAWINGS

FIG. 15 shows graphs of an example of a fitting result in Example 2.

FIG. 32 shows graphs of integration values based on the luminescence amounts of delayed luminescence shown in FIGS. 30 and 31, with FIG. 32A being a graph of the integration value 1, FIG. 32B being a graph of the integration value 2, and FIG. 32C being a graph of the integration value 3.

FIG. 42 is a table of values eII and vII in non-saturation cases of the standard sample and respective exposed samples in the example.

FIG. 43 is a table of values vQ and % oQ of the standard sample and respective exposed samples in the example.

FIG. 44 is a table of values eI and cI in the non-saturation cases of the standard sample and respective exposed samples in the example.

DESCRIPTION OF THE SYMBOLS

Figure 1:
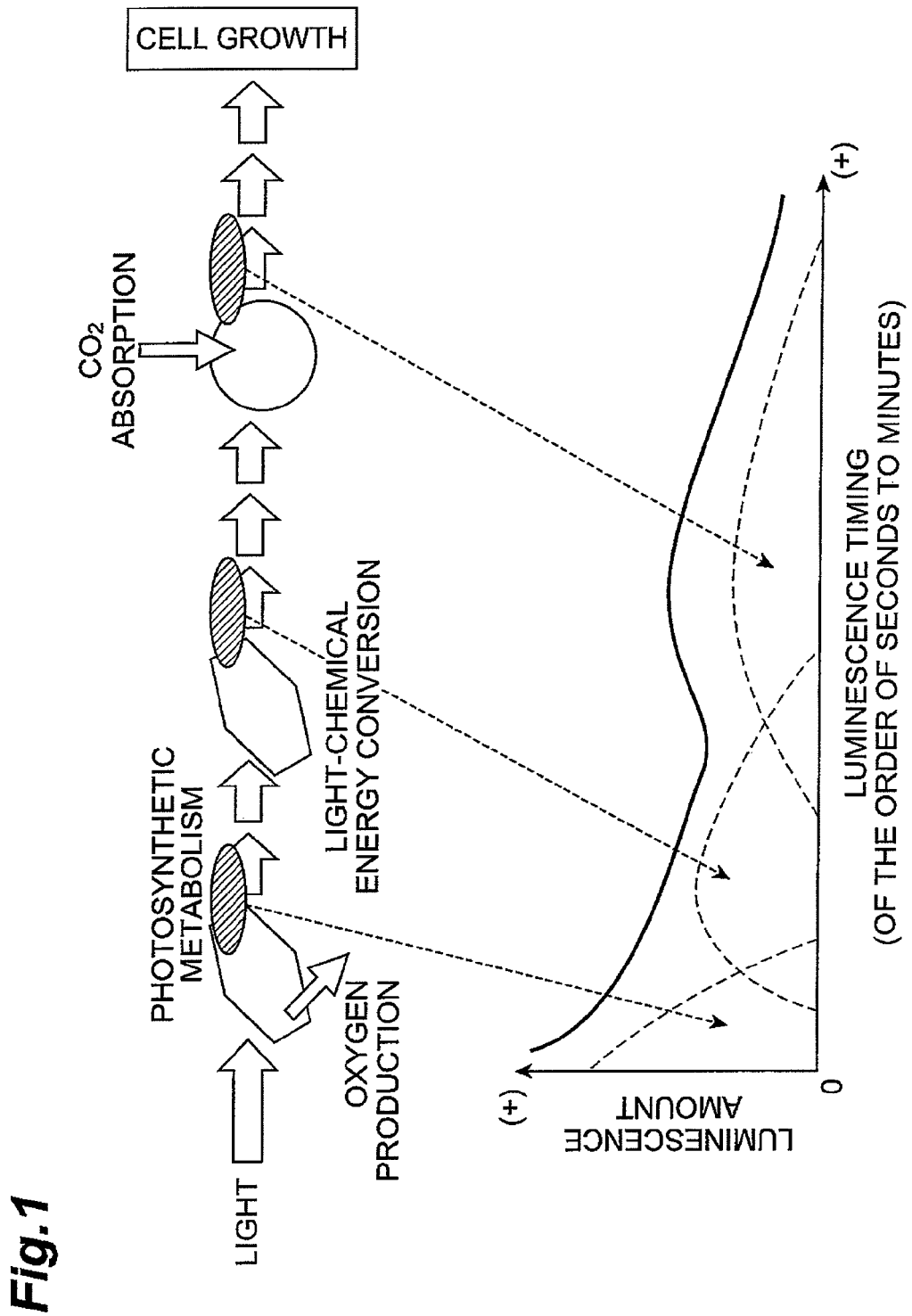
FIG. 1 is a diagram of a mechanism of delayed luminescence.

In FIGS. 1 to 18: 1 . . . environmental factor evaluation system, 10 . . . measuring device, 12 . . . evaluation device, 14 . . . controller, 16 . . . setting unit, 18 . . . light source, 20 . . . light detector, 20a . . . photosensor, 20b . . . delayed luminescence amount computing unit, 22 . . . filter, 24 . . . focusing optical system, 26 . . . shutter, 28 . . . casing, 30 . . . entrance, 32 . . . main unit, 34 . . . lid, 36 . . . receiving unit, 38 . . . fitting unit, 40 . . . evaluating unit, 42 . . . output unit, 44 . . . evaluation value computing unit, 46 . . . comparing unit, 50 . . . recording medium, 50a . . . program storage area, 52 . . . evaluation program, 52a . . . main module, 52b . . . receiving module, 52c . . . fitting module, 52d . . . evaluating module, 52e . . . output module.

In FIGS. 19 to 44: 1 . . . delayed luminescence measuring device, 10 . . . measuring unit, 11 . . . sample setting unit, 12 . . . light source, 13 . . . filter, 14 . . . focusing optical system, 15 . . . shutter, 16 . . . detecting unit, 16a . . . photosensor, 16b . . . light amount computing unit, 17 . . . casing, 17a . . . main unit, 17b . . . lid, 20 . . . analyzing unit, 21 . . . recording unit, 22 . . . computing unit, 23 . . . display unit, 24 . . . input unit, 30 . . . control unit, 31 . . . light source controller, 32 . . . detection controller, 41 . . . first cable, 42 . . . second cable, 50 . . . evaluation program, 51 . . . light source control module, 52 . . . detection control module, 53 . . . computing module, 60 . . . recording medium, 70 . . . computer

BEST MODES FOR CARRYING OUT THE INVENTION

First Embodiment

A first embodiment of the present invention shall now be described in detail along with the drawings. With the present embodiment, an evaluation method, an evaluation system, and an evaluation program for environmental factor shall be described as an embodiment of an evaluation method, an evaluation system, and an evaluation program for photosynthetic sample according to the present invention. In the description of the drawings, elements that are the same shall be provided with the same symbols and redundant description shall be omitted.

With the present invention, an environmental impact of an environmental factor is evaluated based on temporal data of a luminescence amount of delayed luminescence emitted from a plant sample having a photosynthetic function that has been exposed to the environmental factor to be evaluated. As the environmental factor, mainly, a substance that may have an impact on a growth of a living organism is subject to evaluation. River water, well water, factory emission, etc., that are assumed to contain a substance to be evaluated can be cited as examples. Delayed luminescence occurs as follows. That is, in reactions that occur when light is illuminated onto a living organism with a photosynthetic function, light energy, absorbed by an assimilatory pigment (photosynthetic pigment), is transported within the living organism's reaction system as chemical energy via an electron transport pathway. In this transport process, a portion of the chemical energy undergoes a reverse reaction and the photosynthetic pigment is re-excited by the chemical energy. Fluorescence emission arises from the photosynthetic pigment that is thus re-excited. This fluorescence emission is deemed to be the delayed luminescence. Delayed luminescence is also called delayed fluorescence at times and in the following, these shall be referred to collectively as delayed luminescence.

First, a theoretical background of the evaluation method for environmental factor according to the present invention shall be described. The theoretical background described below has been obtained by diligent research by the present inventor and is disclosed for the first time in the present application.

Upon analyzing a temporal variation of a luminescence amount of delayed luminescence of an algae exposed to a chemical substance, which is one type of environmental factor, it was found that photons resulting from different energies are emitted overlappingly at different timings. It was furthermore found that the different energy sources change in their relationships due to influences of chemical reactions in algae metabolism. The different energy sources are assumed to be centers of chemical reactions (photosystems, plastoquinone pool, and other electron storage portions) in algae metabolism.

This shall now be described using FIG. 1, which shows a mechanism of delayed luminescence. Upon receiving light, the algae performs photosynthetic metabolism and this causes cells to grow. In a photosynthetic reaction, light energy, absorbed by a photosynthetic pigment, is transported by a plurality of chemical reactions and converted into energy necessary for cell growth. In this process, oxygen production, light-chemical energy conversion, $CO_2$ absorption, and other reactions that become energy sources of delayed luminescence take place sequentially. Emissions of photons by these reactions occur at different timings, and a sum of these emissions is measured as the delayed luminescence of the algae as a whole.

It was found that each photon emission can be expressed as a function and that the temporal variation of the luminescence amount of delayed luminescence (as a whole) can be fitted as a sum of these functions. The fitting is performed by preparing functions, having coefficient values as variables, in advance and then determining the coefficient values. A measurement result of delayed luminescence, which appears to be complex at first, can thereby be simplified and expressed in a form of coefficient values of the fitted functions. A sum of a plurality of functions is used in the fitting. Fitting can be performed more accurately the larger the number of functions.

Preferably, hill-shaped functions are used as the functions for performing fitting. A hill-shaped function is a function with a hill-like shape that takes on a maximum function value at a specific variable value and is monotonously non-decreasing at variable values no more than the specific variable value and monotonously non-increasing at variable values no less than the specific variable value. Specifically, a hill-shaped function can be constructed from a Lorentz function (Cauchy distribution), a quadratic function, a normal distribution function, etc. As shown in FIG. 1, the time variation of the luminescence amount of delayed luminescence corresponding to each energy source is hill-shaped and accordingly, more accurate fitting is possible. More accurate fitting enables more accurate evaluation. In a case where a hill-shaped function has a peak at 0 or less along the time axis, the function may be substituted by a monotonously non-increasing function such as an exponential function, logarithmic function, etc. In the present embodiment, such functions are included among hill-shaped functions (such functions can be interpreted as hill-type functions, with which the function value takes on the maximum value at a variable value of $-\infty$).

The functions necessary for fitting the temporal variation of the luminescence amount of delayed luminescence can be identified as first, second, and so forth in an order of appearance of the maximum value from a left side. As shown in FIG. 1, a maximum value of later order of appearance (of greater value along the time axis) indicates a corresponding photon that is later in a timing of emission from a cell and considered to be derived from a metabolic reaction that is further proceeded in the cell.

Figure 2:
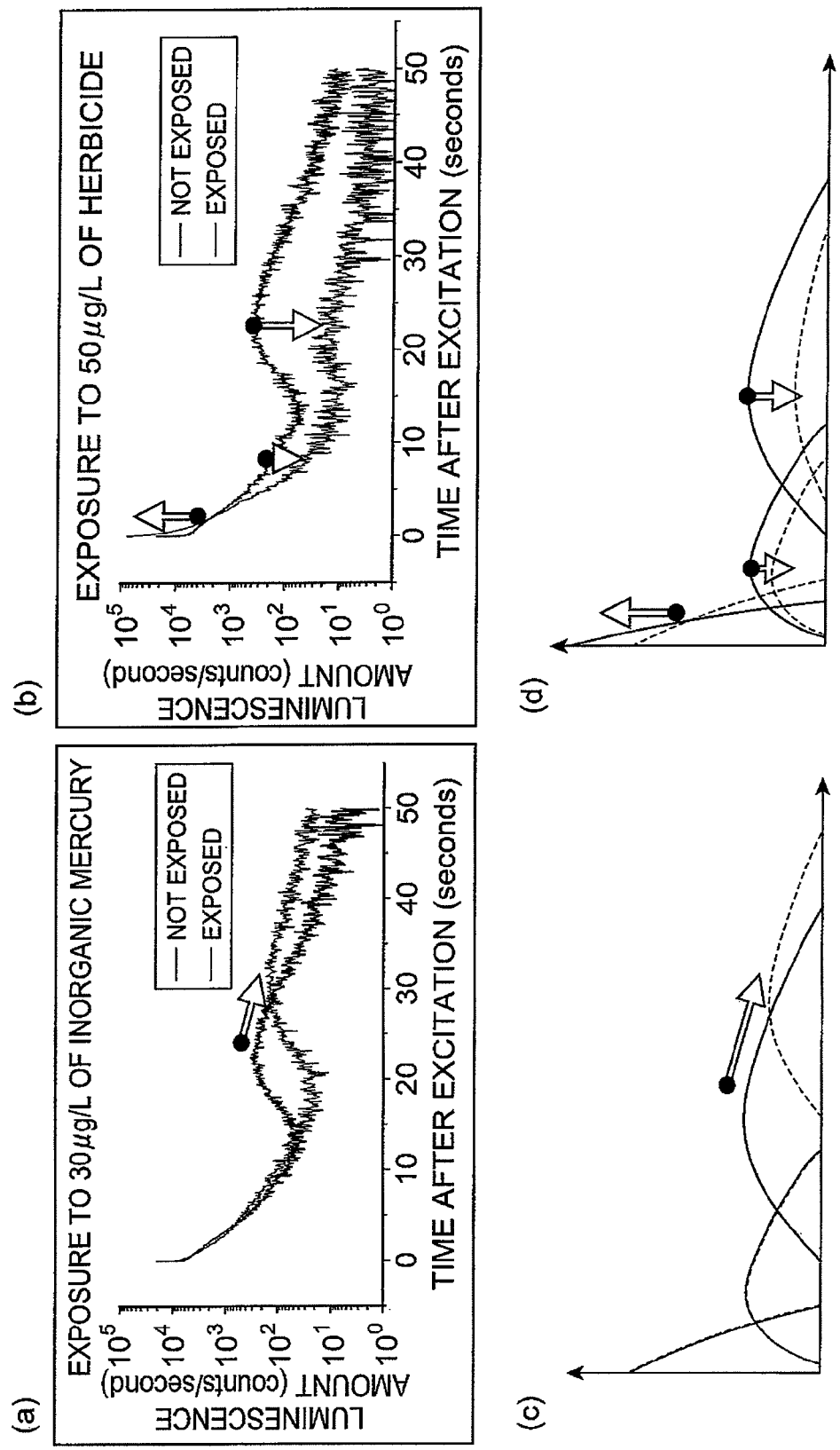
FIG. 2 shows graphs of influences of environmental factors on a luminescence amount of delayed luminescence.

When a harmful environmental factor acts on algae, the intracellular metabolism changes and the temporal variation of the luminescence amount of delayed luminescence becomes different from that in the case where the environmental factor is not acting. Variations of the luminescence amount of delayed luminescence in a case where a plant sample is exposed to a harmful environmental factor and a case where the sample is not exposed are shown in FIG. 2. FIGS. 2A and 2B are graphs of temporal variations of delayed luminescence in respective cases of using inorganic mercury and a herbicide as the environmental factors. As shown in these figures, an environmental factor has an influence on delayed luminescence and the influence on delayed luminescence differs according to the environmental factor.

FIGS. 2C and 2D are schematic graphs respectively corresponding to FIGS. 2A and 2B. In the graphs of FIGS. 2C and 2D, the luminescence amounts are expressed according to energy source (a single hill in a graph corresponds to a single energy source). As shown in these figures, an environmental factor influences each energy source differently. The coefficient values of the respective functions fitted to the variation of the luminescence amount change accordingly. In a case where the growth of algae is inhibited by an environmental factor, changes mainly appear in the coefficient values of the second function onward. It is thus considered that because cell growth is related to reactions that are more proceeded in the metabolism, an evaluation can be made by noting functions that are late in the order of appearance of the maximum value.

Because there are interactions among the generation sources of photons included in the delayed luminescence as shown in FIG. 1, by evaluating the relationships of the different functions, the state of metabolism can be known more accurately. Use of computed values resulting from computation using the coefficient values of the different functions is thus helpful in evaluating intracellular information. Details shall be described below.

A method of fitting the luminescence amount of delayed luminescence to a function is also described, for example, in "Journal of Photochemistry and Photobiology B: Biology 78 (2005) 235-244 Further analysis of delayed luminescence of plants." However, with this method, fitting to a single function is performed instead of fitting to a plurality of functions as in the present invention. With a single function, the temporal variation of the luminescence amount of delayed luminescence, with which a plurality of energy sources are involved as shown in FIG. 1, cannot be fitted accurately. That is, it is difficult to make an accurate evaluation with the above-mentioned conventional art. The above is the theoretical background of the present invention.

Figure 3:
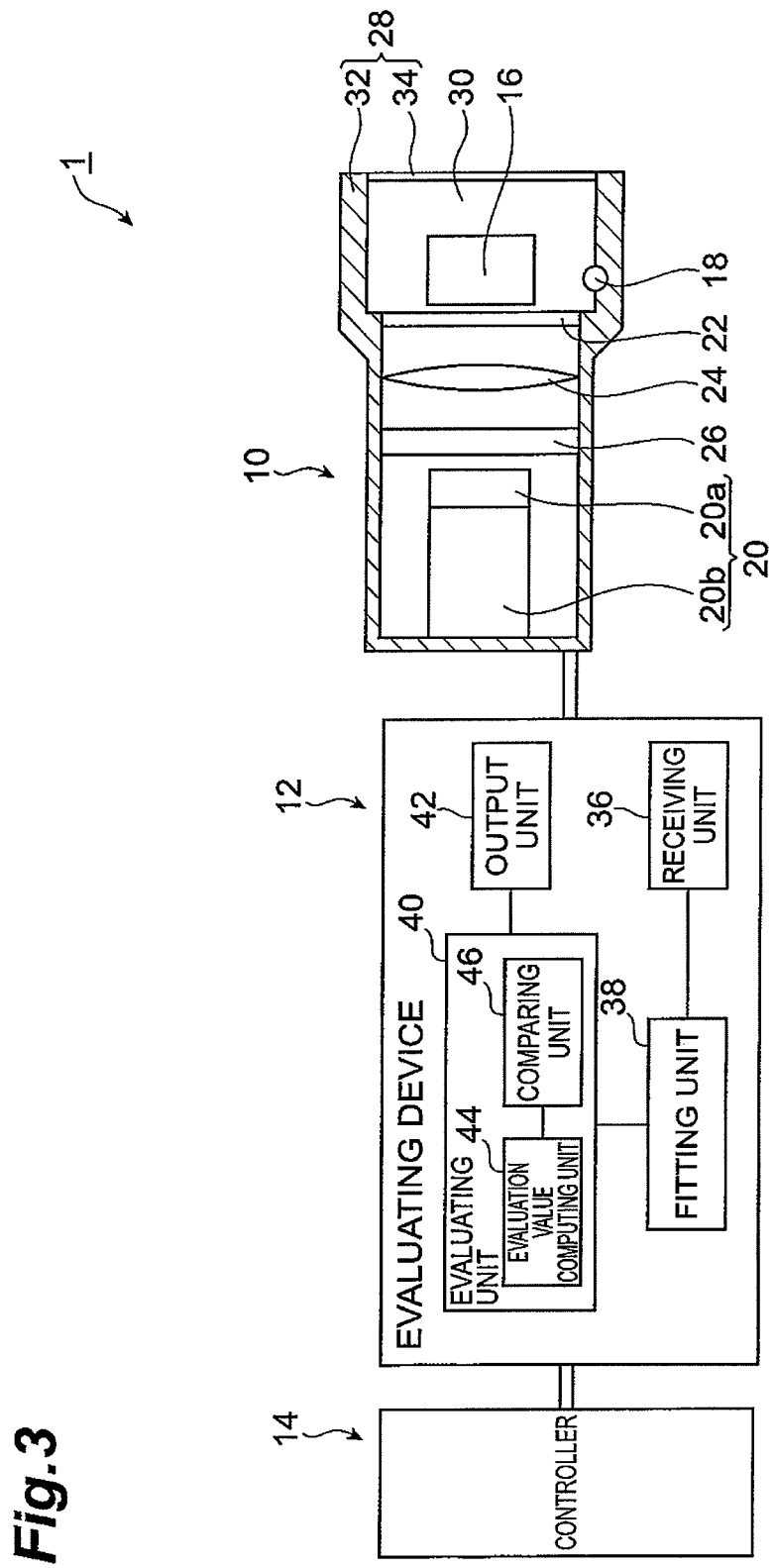
FIG. 3 is a diagram of a configuration of an evaluation system for environmental factor according to an embodiment.

The evaluation method and evaluation system for environmental factor according to the present embodiment shall now be described further. FIG. 3 shows a configuration of the evaluation system 1 according to the present embodiment. As shown in FIG. 3, the environmental factor evaluation system 1 according to the present embodiment is constituted of a measuring device 10, an evaluating device 12, and a controller 14. The measuring device 10 and the evaluating device 12 are connected by a cable and thereby enabled to perform sending and receiving of information with respect to each other. The evaluating device 12 and the controller 14 are connected by a cable and thereby enabled to perform sending and receiving of information with respect to each other. The measuring device 10 and the controller 14 are enabled to perform sending and receiving of information with respect to each other via the evaluating device 12.

The measuring device 10 is a device that measures a luminescence amount with time of a delayed luminescence from a plant sample having a photosynthetic function. Here, the plant sample includes that which is exposed to an environmental factor to be evaluated. The measuring device 10 inputs the measured temporal data of the luminescence amount of delayed fluorescence into the evaluating device 12. In FIG. 3, a cross section of the measuring device 10 is shown. A specific configuration of the measuring device 10 shall be described later.

The evaluating device 12 receives input of the temporal data of the luminescence amount of delayed luminescence from the measuring device 10 and evaluates an environmental impact of the environmental factor based on the temporal data. Here, the environmental impact is specifically, for example, an influence that inhibits algae growth, etc. Specifically, a PC (personal computer), etc., corresponds to being the evaluating device 12, and the device is constituted of a CPU (central processing unit), memory, and other hardware. With the evaluating device 12, various functions, to be described below, are exhibited by the hardware components operating according to a program, etc. In FIG. 3, the functions of the evaluating device 12 are shown.

The controller 14 includes a CPU (central processing unit), memory, and other hardware and sends a control signal to the measuring device 10 to control operations of the measuring device 10. The measuring device 10 and the evaluating device 12 shall now be described in more detail.

As shown in FIG. 3, the measuring device 10 includes a setting unit 16, a light source 18, a light detector 20, a filter 22, a focusing optical system 24, and a shutter 26. The measuring device 10 also has a casing 28 and the various components mentioned above are disposed inside the casing 28. To prevent light from entering inside, the casing 28 is formed of a light blocking member that blocks light in itself or is formed of a material that is coated with a coating, etc., that blocks light. The casing 28 is constituted of a main unit 32 having an entrance 30 formed at one end, and a lid 34 that can close the entrance 30. The opening and closing of the lid 34 is monitored and controlled by the controller 14, and in a state where the shutter 26 is opened, the lid 34 is locked so as to disable opening/closing and thereby prevent entry of light from an exterior of the casing 28 into the light sensor 20.

The setting unit 16 is for setting a container that contains an environmental factor and a plant sample to be measured (for example, a solution containing a chemical substance and the plant sample). The setting unit 16 is disposed at a position enabling the container to be set from the entrance 30. The setting unit 16 has, for example, a fixing claw for fixing the container and the container is fixed by the fixing claw.

The light source 18 is for illuminating light of a predetermined wavelength onto the plant sample in the container set in the setting unit 16 to cause delayed luminescence to be emitted and is disposed at a position and a direction enabling illumination of the light onto the plant sample. The wavelength of the light illuminated from the light source 18 is in a range of 280 nm to 800 nm. Here, the light source may be a monochromatic light source or a combination of a plurality of light sources. The illumination of the light from the light source 18 may be sustained for any predetermined amount of time or may be pulsed according to any pattern. A plurality of light sources with the same or different wavelength characteristics may be made to emit light according to a sequence or a plurality of light sources may be made to emit light simultaneously. The illumination of light by the light source 18 is controlled by the controller 14.

The light detector 20 measures the luminescence amount of delayed luminescence emitted from the plant sample due to illumination of the light from the light source 18. The light detector 20 includes a photosensor 20a detecting the delayed luminescence, and a delayed luminescence amount computing unit 20b, computing and outputting the luminescence amount of delayed luminescence based on a signal output upon detection by the photosensor 20a. The light detector 20 is disposed at a position and a direction enabling detection of the delayed luminescence. The light detector 20 is specifically constituted of a photomultiplier tube, a photon counter, etc. The luminescence amount information output successively from the delayed luminescence amount computing unit 20b is input as temporal data into the evaluation device 12.

The filter 22, the focusing optical system 24, and the shutter 26 are disposed in that order from the setting unit 16 side between the setting unit 16 and the light detector 20. The filter 22 is disposed so as to contact an inner wall surface of the casing 28 and transmits the delayed luminescence. The focusing optical system 24 focuses, reflects and transmits the weak delayed luminescence and thereby inputs the delayed luminescence into the light detector 20. The shutter 26 is enabled to be opened and closed and blocks the delayed luminescence when closed. This is done so that the delayed luminescence is detected by the light detector 20 only when necessary. The opening and closing of the shutter 26 are controlled by the controller 14. Thus, the measuring device 10 is configured.

As shown in FIG. 3, the evaluating device 12 includes a receiving unit 36, a fitting unit 38, an evaluating unit 40, and an output unit 42. The receiving unit 36 is a receiving means that receives input of the temporal data of the luminescence amount of delayed luminescence emitted from the plant sample. This input is the input from (the delayed luminescence amount computing unit 20b of) the measuring device 10. Here, as the temporal data of the luminescence amount, both the data for the case where the plant sample is exposed to the environmental factor to be evaluated (the chemical substance to be evaluated is contained in the solution) and the case where the sample is not exposed to the environmental factor (the chemical substance to be evaluated is not contained in the solution) are input. The received data are sent to the fitting unit 38.

The fitting unit 38 is a fitting means that determines coefficient values of a plurality of priorly set functions, so that the temporal data, the input of which is received by the receiving unit 36, are fitted to a sum of the functions. Information on the functions is stored in the fitting unit 38 in advance. As the functions, hill-shaped functions are preferably used as mentioned above. Specifically, Lorentz functions (Cauchy distributions), each having the following form:

[Mathematical Formula 4]

$$\frac{c_1}{10^{1+a_1(t-b_1)^2}},$$

$$\frac{c_2}{10^{1+a_2(t-b_2)^2}},$$

$$\frac{c_3}{10^{1+a_3(t-b_3)^2}}$$

with $a_i$, $b_i$, and $c_i$ (i=1, 2, 3) being the coefficient values of the plurality of functions and t being a variable indicating an elapsed time from a base time (time after excitation), are preferably used. The sum of the plurality of functions used for fitting is expressed as follows:

[Mathematical Formula 5]

$$fm(t) = 10^{\frac{c_1}{1+a_1(t-b_1)^2}} + 10^{\frac{c_2}{1+a_2(t-b_2)^2}} + 10^{\frac{c_3}{1+a_3(t-b_3)^2}} \quad (1)$$

Figure 4:
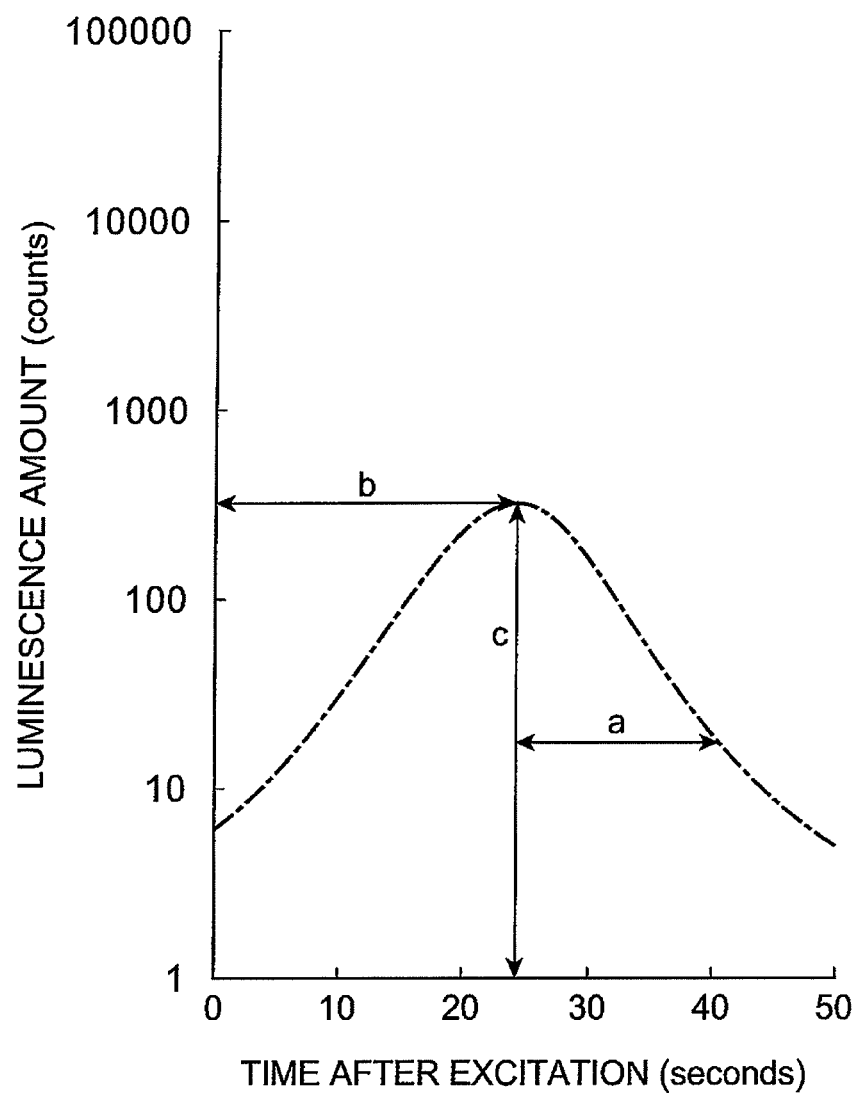
FIG. 4 is a graph of a function for performing fitting and shows influences of coefficient values of the function.

Here, the base time t is, for example, set to a time after elapse of a specific, priorly set duration from a time at which the illumination of light from the light source 18 is ended. As shown in FIG. 4, in each function, ai influences a spread in a direction of time, bi influences t (time after excitation) at which the luminescence amount takes on a maximum value, and ci influences a peak value of the maximum value. In Formula (1), a first term, a second term, and a third term at the right hand side are respectively orders of appearance of the maximum value along the time axis and are expressed as a first function, a second function, and a third function. That is, with the coefficients of the functions, a relationship: $b1<b2<b3$ holds. A sum of three functions is used as described because it is considered that three different reactions that serve as energy sources for photons are present as shown in FIG. 1, etc. In a case where the number of reactions that serve as photon energy sources is a number than three, the number of functions is preferably set accordingly. As the functions used for fitting, quadratic functions, normal distribution functions, and other hill-shaped functions besides the above may be used.

Functions other than hill-shaped functions may be used as long as the functions fit well. For example, the following functions, with which coefficients di (i=1, 2, 3) are added to the functions of Formula (1), may be used instead.

[Mathematical Formula 6]
$$fm(t) = \frac{c_1}{10^{1+a_1(t-b_1)^{d_1}}} + \frac{c_2}{10^{1+a_2(t-b_2)^{d_2}}} + \frac{c_3}{10^{1+a_3(t-b_3)^{d_3}}}$$

By thus increasing the number of coefficients, the degree of freedom of fitting can be increased.

An algorithm for performing fitting is also stored in advance in the fitting unit 38. As the fitting algorithm, specifically, a nonlinear analysis method, such as a simplex method, Gauss-Newton method, Davidon Fletcher Powell method, Brent's method, etc., or a Monte Carlo method, simulated annealing method, etc., may be used. Fitting conditions may be set in accordance with the type of the plant sample and the measurement conditions. The coefficient values determined at the fitting unit 38 are sent to the evaluating unit 40.

The evaluating unit 40 is an evaluating means that evaluates the environmental impact of the environmental factor based on the coefficient values determined by the fitting unit 38. Here, evaluation specifically refers to numerically expressing a degree of impact (harmfulness) and making a judgment between harmful and non-harmful using the numerically expressed value.

As shown in FIG. 3, the evaluating unit 40 includes an evaluation value computing unit 44 and a comparing unit 46 for performing the evaluation. The evaluation value computing unit 44 is an evaluation value computing means that computes an evaluation value for evaluating the impact from the coefficient values determined by the fitting unit 38. The computation of the evaluation value is, for example, performed based on an evaluation value computing formula stored in advance by the evaluation value computing unit 44.

As mentioned above, because there are a plurality of generation sources of the photons that cause the delayed luminescence and there are interactions among the sources, by evaluating a relationship of different functions, the state of metabolism can be known more accurately. Use of the evaluation value computed from the coefficient values of different functions is thus helpful in evaluating intracellular information. Preferably, the evaluation value is specifically derived using the following computation formula:

[Mathematical Formula 7]

Evaluation value=$((m_1 \cdot a_3 \times m_2 \cdot b_3 \times m_3 \cdot c_3)/(m_4 \cdot a_2 \times a_2 \times m_5 \cdot b_2 \times m_6 \cdot c_2))/(m_7 \cdot a_1 \times m_8 \cdot b_1 \times m_9 \cdot c_1)$ (2)

Figure 5:
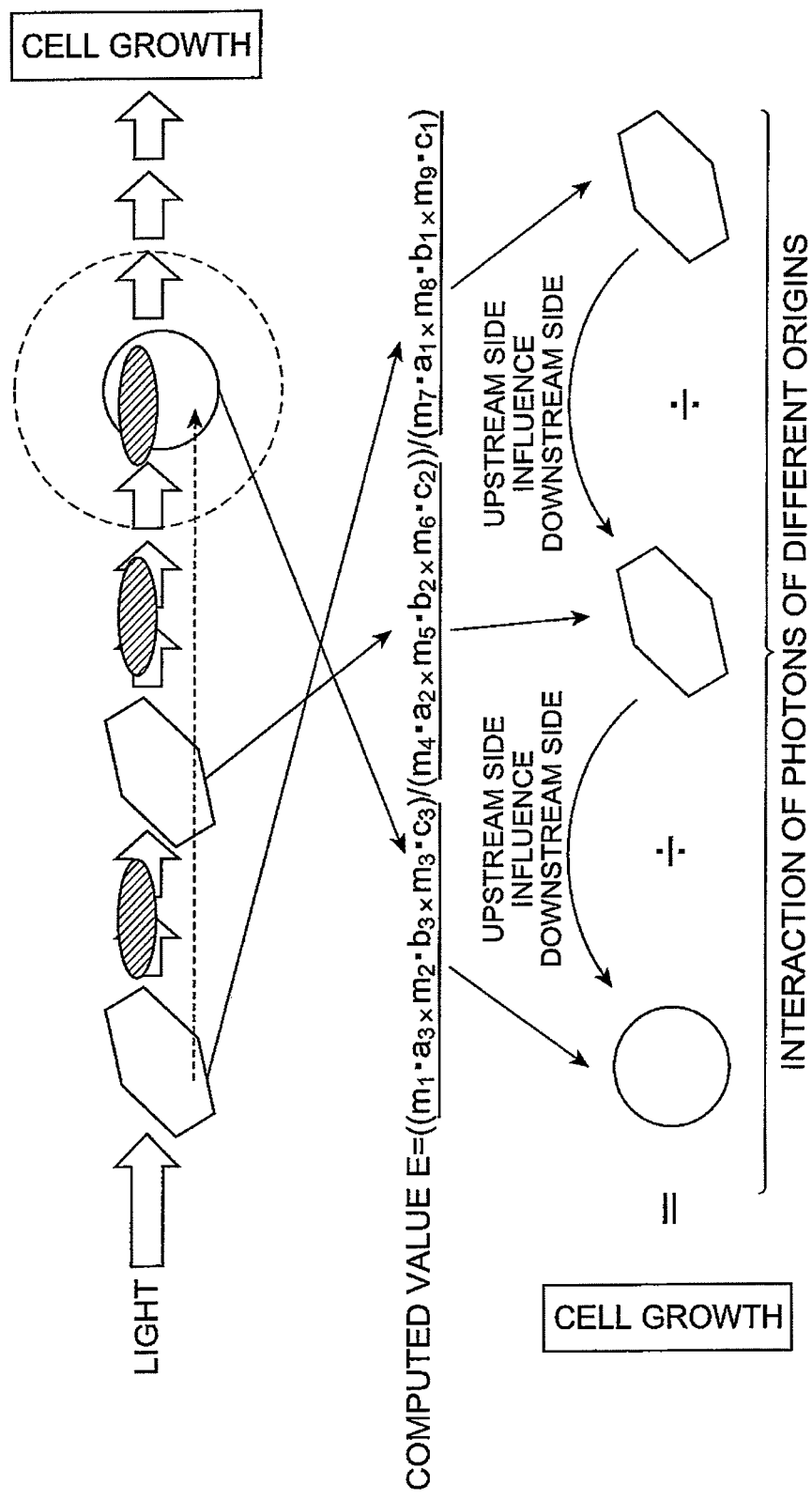
FIG. 5 is a diagram of a relationship of an evaluation formula for determining an evaluation value and a delayed luminescence process.

Here, mj (j=1 to 9) are constants that are set appropriately in advance or in the evaluating process. The above formula is preferable because, as shown in FIG. 5, it expresses the interactions among the photon energy sources. The computed evaluation value is thus preferably computed based on a computation formula that includes the coefficients of at least two or more functions among the plurality of functions. This is because evaluation, which takes into consideration the interactions among the photon energy sources expressed by the functions, is thereby enabled. The evaluation value does not have to be computed based on a computation formula, and a coefficient value itself may be used as the evaluation value.

The comparing unit 46 is a comparing means that compares the evaluation value, computed by the evaluation value computing unit 44, with reference data on the evaluation value. Here, the reference data are data derived by the above-described respective processes based on delayed luminescence from a plant sample that is not exposed to the environmental factor to be evaluated. The evaluating unit 40 performs evaluation based on the result of comparison by the comparing unit 46. Details shall be described later. The evaluation result information is sent to the output unit 42.

The output unit 42 is an output means that outputs information on the evaluation by the evaluating unit 40. Specifically, for example, output to a display provided in the evaluating device 12 is performed. By the output by the output unit 42, a user can check evaluation details. Output by the output unit 42 is not restricted to such a screen output and may, for example, be an output to another device.

Figure 6:
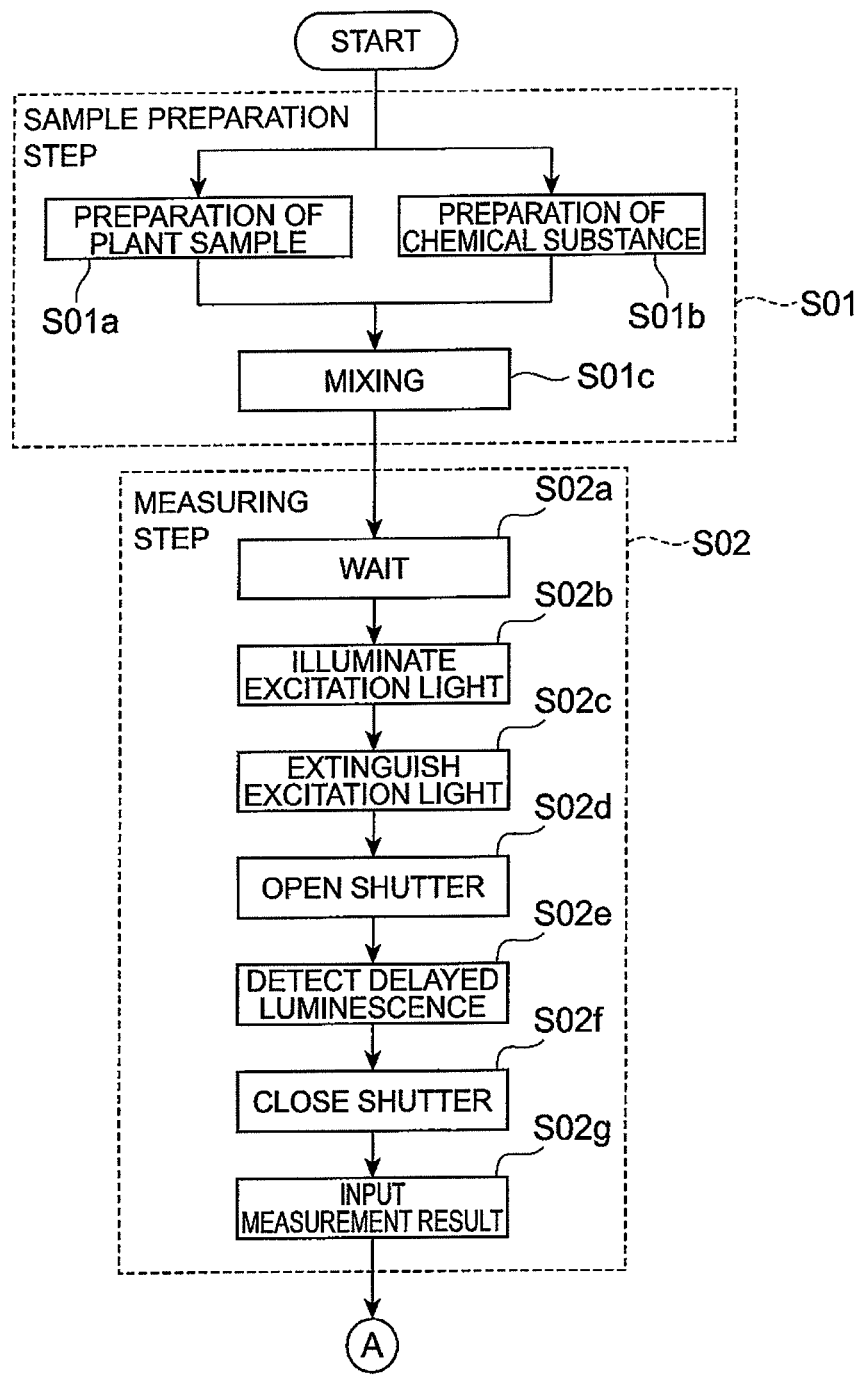
FIG. 6 is a flowchart of an evaluation method for environmental factor according to an embodiment of the present invention.
Figure 7:
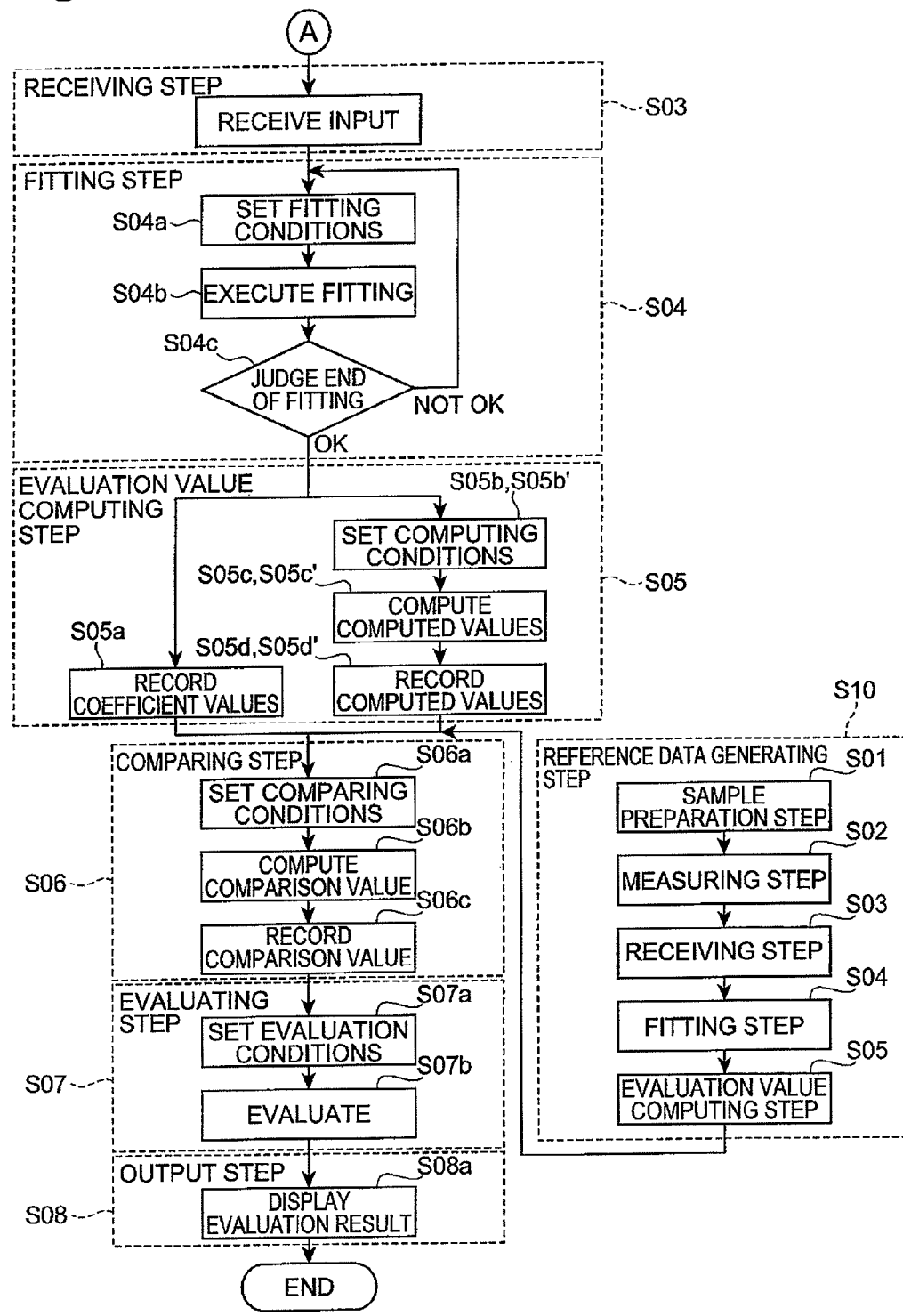
FIG. 7 is a flowchart of the evaluation method for environmental factor according to the embodiment of the present invention.

An evaluation method for environmental factor according to the embodiment (processes executed in the environmental factor evaluation system 1) shall now be described with a chemical substance as an example of an environmental factor and using flowcharts of FIGS. 6 and 7.

First, a sample (hereinafter referred to as the "exposed sample"), which is a solution containing the chemical substance to be evaluated and a plant sample for generating delayed luminescence, is prepared (S01; sample preparation step). The preparation is specifically carried out as follows.

The plant sample is prepared (S01a). As the plant sample, an algae, such as *Spirulina platensis*, which is a blue-green algae, or *Pseudokircheneriella subcapitata*, which is a green algae, etc., is preferably used. For absorbance adjustment, the plant sample is prepared as a suspension with a predetermined absorbance, such as an absorbance of 1 for light with a wavelength of 685 nm (OD685). The chemical substance is also prepared (S01b). As the chemical substance to be evaluated, for example, the herbicide, simazine (CAT), inorganic mercury, or other plant cell growth inhibition substance is used. To facilitate sample preparation, the chemical substance is contained in a liquid algae culture medium (C medium). The prepared plant sample and the chemical substance are then mixed to prepare the sample (S01c). For example, by mixing 2 ml of the liquid algae culture medium, containing the chemical substance, with 0.5 ml of the above-mentioned suspension, an exposed sample of OD685-0.2 can be obtained. Although for sample preparation, the evaluation system 1 for chemical substance by the present embodiment does not necessarily have to be used, the evaluation system 1 may be provided with a mechanism for performing the above process automatically.

The exposed sample thus prepared is then made to emit delayed luminescence and the luminescence amount with time of the delayed luminescence is measured using the measuring device 10 of the chemical substance evaluation system 1 (S02; measuring step). The measurement is specifically performed as follows.

The prepared exposed sample is made to wait for a fixed duration in an environment, inside or outside the measuring device 10 and in which light conditions and temperature are controlled at predetermined conditions (S02a). This waiting is for making the chemical substance act on the plant sample or to make the plant sample adapt to a change of conditions, such as a change of light environment, cell density, etc., due to mixing of the plant sample and the chemical substance. As a specific waiting condition, for example, 15 minutes under a white fluorescent lamp of a light amount of 5 µmol·m−2·s−1, etc., is preferable.

The exposed sample that had been made to wait is then set in the setting unit 16 inside the measuring device 10 and illuminated with light from the light source 18 (S02b). As mentioned above, in regard to the illumination of light, the light is for making the plant sample perform photosynthesis and must contain a spectrum that enables the plant sample to perform photosynthesis. Specifically for example, red light (wavelength: 660 nm) of approximately 300 µmol·m−2·s−1 is illuminated for 10 seconds. The duration of the light illumination is set in advance. Also, during the light illumination, the lid 34 and the shutter 26 of the measuring device 10 are closed to prevent entry of light from the exterior.

When the priorly set illumination duration has elapsed, the light emission by the light source 18 is stopped (S02c) and the shutter 26 is opened (S02d). Delayed luminescence is emitted from the exposed sample illuminated by the light. The focusing optical system 24 focuses, reflects, and transmits the delayed luminescence, emitted in various directions, to guide and make the delayed luminescence from the exposed sample become incident on the light detector 20. The light detector 20 measures the luminescence amount of the delayed luminescence made incident by the focusing optical system 24 (S02e). The measurement is performed continuously for a priorly set duration to measure the luminescence amount with time. Specifically for example, the luminescence amount is measured for 50 seconds at 0.1 second intervals. During the illumination of light from the light source 18, the light detector 20 is protected by the shutter 26 and the casing 28 against incidence of light from the exterior.

Figure 10:
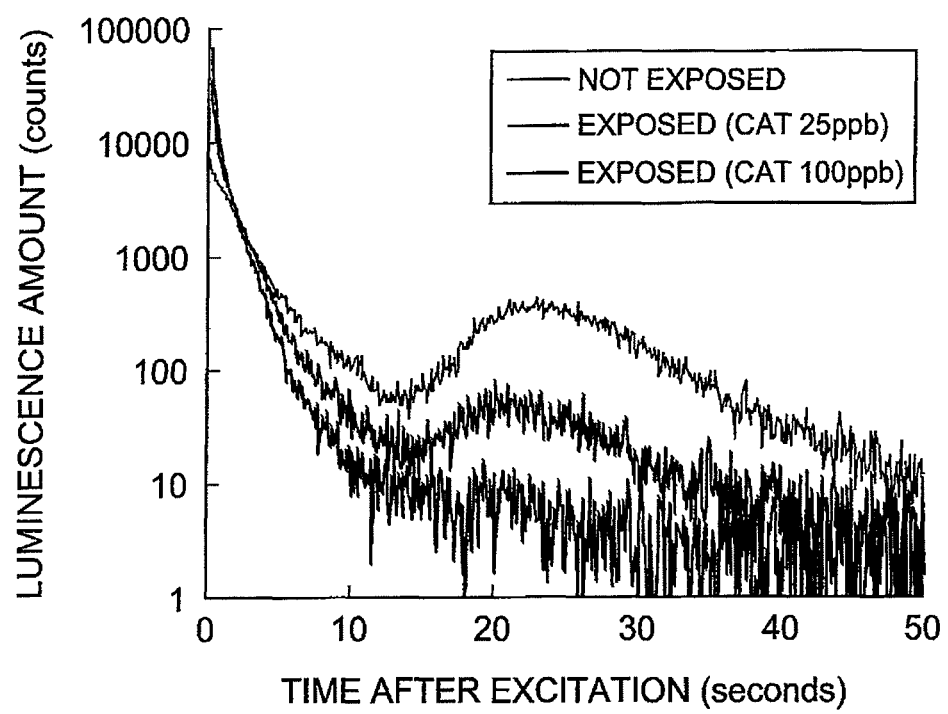
FIG. 10 is a graph of luminescence amounts of delayed luminescence emitted from *S. platensis* (plant sample) in Example 1.

When the priorly set measurement duration has elapsed, the shutter 26 is closed (S02f) and the measurement by the light detector 20 ends. Measurement data of the delayed luminescence are input from (the delayed luminescence amount computing unit 20b of the light detector 20 provided in) the measuring device 10 into the evaluating device 12 (S02g). With the input evaluation data, for example, information on the time after excitation is associated with information on the luminescence amount. Examples of the information expressed in graph form are shown in FIG. 10.

In the evaluating device 12, into which are input the measurement data that are the temporal data of the luminescence amount of delayed luminescence, the receiving unit 36 receives the input (S03 (S03a); receiving step). The temporal data of the luminescence amount of delayed luminescence that have been input are sent to the fitting unit 38.

Then in the evaluating device 12, the fitting unit 38 determines coefficient values of a plurality of functions to fit the input temporal data of the luminescence amount of delayed luminescence as a sum of the functions (S04; fitting step). The fitting is specifically carried out as follows.

First, the fitting unit 38 sets fitting conditions (S04a). The setting of the fitting conditions specifically refers, for example, to determining the type of functions used in the fitting, setting a portion of the coefficients of the functions to fixed values set in advance (the coefficient values that are not fixed are determined in the fitting step), setting an allowable range of error used as a fitting ending condition to be described later, etc. The setting is preferably performed in accordance with the type of the plant sample and the measurement conditions used in the measurement. The setting of the conditions may be performed based on information input in advance by the user or based on a rule held in advance by the fitting unit 38.

The fitting unit 38 then performs the fitting (S04b). The fitting is performed with the function variable value being associated with the time after excitation and the function value being associated with the luminescence amount. The fitting is performed based on the algorithm stored in advance in the fitting unit 38. The coefficient values of the respective functions are determined by the fitting. For example, in a case where the functions expressed by Formula (1) given above are used, the respective values of $a_i$, $b_i$, and $c_i$ ($i=1$, 2, and 3) are determined.

The fitting unit 38 then judges whether the fitting result satisfies a fitting ending condition (S04c). Examples of the fitting ending condition include the error between the fitting result and the measurement result falling within the predetermined allowable range, the coefficient values and a mutual relationship between the coefficient values falling within predetermined allowable ranges, etc. If the fitting ending condition is satisfied, the fitting is ended and the information concerning the fitting, including the determined function values, are sent to the evaluating unit 40. If the fitting ending condition is not satisfied, the fitting conditions are set anew (S04a) and fitting is executed again (S04b).

Next, in the evaluating device 12, the evaluating value computing unit 44, included in the evaluating unit 40, computes an evaluation value for evaluating the environmental impact of the chemical substance from the coefficient values determined by the fitting unit 38 (S05; evaluation value computing step, evaluating step). In regard to the evaluation value, at least one of using all or a portion of the coefficient values as evaluation values; obtaining the evaluation value by computation based on a predetermined computation formula using the coefficient values; and using a function area value, computed based on the coefficient values; is performed. Here, the function area value is an area value of a region surrounded by the function value and, for example, a variable axis (the time axis in the present embodiment) (a range of the variable may be set) in a function graph, etc. In the present embodiment, the function value is the luminescence amount and the variable axis is the time axis. The type of value to be used as the function value is set in advance.

If a coefficient value is to be used as the evaluation value, the coefficient value is recorded as the evaluation value (S05a). On the other hand, if a computed value is to be used as the evaluation value, the evaluation value computing unit 44 first performs setting of a computing condition (S05b). The computing condition is, for example, the computation formula used in the computation. The computing condition is preferably set based on the type of the plant sample and the measurement conditions used in the measurement. The evaluation value computing unit 44 then performs computation based on the set computation conditions to compute a computed value (S05c). The computed value is recorded as the evaluation value by the evaluation value computing unit 44.

If an area value is to be used as the evaluation value, first, a function for computing the area value and a range of the time (t) for computing the area value are set (S05b'). Here, area values may be computed for all of the functions used in the fitting or may be computed upon selecting at least one function. Preferably, the selection of function is performed based on the type of the plant sample and the measurement conditions used in the measurement. More specifically, the function for computing the area value may be selected based on the order of appearance of the maximum value along the time axis or the function may be selected based on the luminescence amount. For example, in the case where the function is selected based on the order of appearance of the maximum value along the time axis, the function that is latest in order is preferably used. As another selection method, a function, with which an amount of change of a coefficient value, evaluation value, etc., with respect to the below-described reference data is largest, may be selected. The time (t) range for computing the area is preferably set based on the type of the plant sample and the measurement conditions used in the measurement. More specifically, the time (t) range is preferably an entire range of the delayed luminescence measurement time. In a case where a partial time range is to be selected from the entire range of the measurement time, a time range corresponding to a half-value width with respect to the maximum value of the function may be selected. Furthermore, in a case where the time range corresponding to the half-value width with respect to the maximum value of the function is not included within the measurement time range, that is, when a range exceeding the measurement time is to be selected, the time range corresponding to the half-value width may be estimated from the fitted function and this time range may be selected. Then based on the coefficient values associated with the selected function and the selected time (t) range, the evaluation value computing unit 44 computes the area value by quadrature by parts, etc., (S05c'). Specifically, values of the coefficient values a3, b3, and c3 are substituted into the third function in Formula (1) and quadrature by parts is performed on the selected time (t) range. The area value is recorded as the evaluation value by the evaluation value computing unit 44 (S05d'). Because with the evaluation by area value, just the area value related to the function is computed, a more simplified evaluation is enabled.

Next, in the evaluating device 12, the comparing unit 46, included in the evaluating unit 40, compares the evaluation value, computed in the evaluation value computing unit 44, and the reference data of the evaluation value to evaluate the environmental impact of the chemical substance (S06; comparing step, evaluating step). The reference data are data that can be an object of comparison with the evaluation value, computed as described above, to evaluate the environmental impact of the chemical substance. Specifically, the reference data are data derived from measurement data obtained by measuring the luminescence amount with time of the delayed luminescence emitted from a photosynthetic sample mixed in a solution that does not contain the chemical substance.

The reference data are derived separately and in advance before the present step (S10; reference data generating step). The reference data are generated in the same manner as in steps S01 to S05, described above. However, the sample preparation in S01 is performed without making the evaluated chemical substance be contained in the sample. As the conditions set in the respective steps, the same conditions as those derived in the case where the evaluated chemical substance is contained are used.

The comparison of the evaluation value is carried out as follows. The comparing unit 46 sets a computation condition of a comparison value (S06a). The comparison value is a value that is computed as a comparison result and is used to evaluate the environmental impact of the chemical substance. The computation condition of the comparison value is, for example, a computation formula, etc., used in the computation. As the computation formula, for example, a formula that determines a ratio or difference of the evaluation value, computed from the measurement data of the exposed sample, with respect to the evaluation value of the reference data, etc., may be used. The comparison value computation condition is preferably set based on the type of the plant sample and the measurement conditions used in the measurement.

The comparing unit 46 then reads each evaluation value recorded by the evaluation value computing unit 44 and computes the comparison value based on the set condition (S06b). The computed comparison value is then recorded by the comparing unit 46 (S06c).

Next in the evaluating device 12, the evaluating unit 40 evaluates the environmental impact of the chemical substance based on the comparison value (S07; evaluating step). The evaluation is specifically carried out as follows. The evaluating unit 40 sets an evaluating condition (S07a). Specifically, the evaluating condition is a rule, etc., used for evaluation and is preferably determined based on the type of the plant sample and the measurement conditions used in the measurement. The rule used for evaluation is stored in advance by the evaluating unit 40.

The evaluating unit 40 then reads the comparison value recorded by the comparing unit 46 and performs evaluation according to the set condition (S07b). Specifically, the evaluation is performed, for example, by collating the comparison value using a priorly prepared evaluation table, in which comparison values are associated with environmental impact, and thereby computing the environmental impact as a numerical value, such as a growth inhibition degree, etc. Or, a threshold value may be set in advance, and a dichotomous evaluation of judging the harmfulness of the chemical substance as harmful or non-harmful according to whether or not the comparison value exceeds the threshold value may be performed. The information obtained by the evaluation is sent to the output unit 42.

The output unit 42 outputs information on the evaluation by the evaluating unit 40 (S08 (S08a); output step). As mentioned above, the output is performed by screen display by a display device, etc. As the output, numerical values relevant to the evaluation may be output in the form of a table and a ○ (circle) may be displayed in the harmful case or a x (cross) may be displayed in the non-harmful case. The numerical values may also be displayed in the form of a graph. The evaluation information that is output is referenced as necessary by the user.

As described above, with the present embodiment, an objective and mechanical evaluation can be made in accordance with the functions. Also, because the temporal data of the luminescence amount of delayed luminescence are fitted to the sum of the functions, evaluation based on the mechanism of the delayed luminescence is enabled. Thus by the evaluation method for environmental factor according to the present embodiment, an environmental impact of an environmental factor can be evaluated appropriately and easily:

Also because by measuring the delayed luminescence as in the present embodiment, evaluation based on actual measurement data can be performed, a more appropriate evaluation can be made. However, in a case where actual measurement data are made available in advance, etc., the delayed luminescence does not necessarily have to be measured and the evaluation can be started from the input of the temporal data of the luminescence amount of delayed luminescence.

Also, by setting the evaluation value and evaluating it by comparison with the reference data as in the present embodiment, evaluation can be made more clearly by setting an evaluation value suited for evaluation.

Although not mentioned with the present embodiment, an absorbance of the solution may be measured and an evaluation can be made in consideration of the absorbance as described in Patent Document 1.

Although with the present embodiment, a case where a chemical substance in solution is the object of measurement was described as an example, the measurement object may be river water, well water, factory emission (wastewater, soil, gas), etc. With the present invention, light factors, temperature factors, oxygen factors, carbon dioxide factors, salt content factors, and various other environmental factors can be cited as other environmental factors that can be evaluated. For example, in a case where an environmental impact of a factory emission gas is to be evaluated, the factory emission gas is introduced by a pipe, etc., into a space in which a plant sample is housed. Or, to evaluate an impact of a temperature factor on a plant sample, a temperature controller is disposed in a space in which the plant sample is housed.

Figure 8:
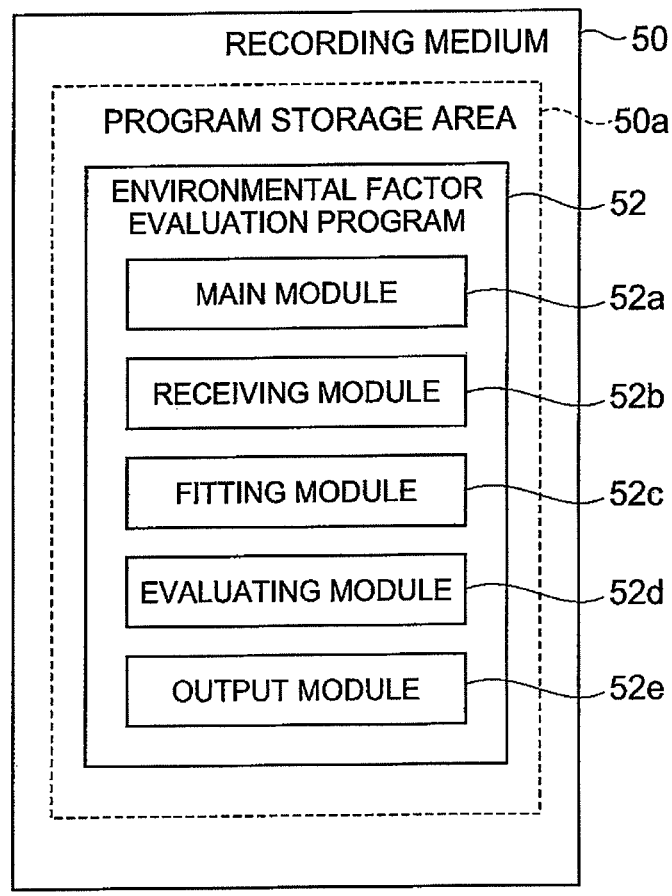
FIG. 8 is a diagram of a configuration of an evaluation program for environmental factor according to the present invention.

An evaluation program for environmental factor that makes a computer execute the above-described series of processes for evaluating an environmental factor shall now be described. As shown in FIG. 8, the environmental factor evaluation program 52 is stored in a program storage area 50*a*, formed inside a storage medium 50 provided in the computer.

The environmental factor evaluation program 52 is constituted of a main module 52*a*, performing overall control of the environmental factor evaluating processes, a receiving module 52*b*, receiving input of temporal data of a luminescence amount of delayed luminescence emitted by a plant sample having a photosynthetic function that has been exposed to an environmental factor, a fitting module 52*c*, determining coefficient values of a plurality of priorly set functions, so that the temporal data, the input of which is received, are fitted to a sum of the functions, an evaluating module 52*d*, evaluating the environmental impact of the environmental factor based on the determined coefficient values, and an output module 52*e*, outputting information on the evaluation. Functions that are realized by execution of the receiving module 52*b*, the fitting module 52*c*, the evaluating module 52*d*, and the output module 52*e* are respectively the same as the functions of the receiving unit 36, the fitting unit 38, the evaluating unit 40, and the output unit 42 of the evaluating device 12 described above.

A portion or entirety of the environmental factor evaluation program 52 may be configured to be transmitted via a communication line or other transmission medium and received and recorded (including installation) in another equipment.

Examples of the above-described embodiment shall now be described. However, the present invention is not restricted to the following examples.

Although in the following examples, an algae is used as the plant sample, the present invention is not restricted thereto, and it suffices that the plant sample has a photosynthetic function and emits delayed luminescence, and phytoplankton, cyanobacteria, photosynthetic bacteria, plant bodies, leaves, or fragments thereof, calluses and other cultured plant cells, photosynthetic organelles and thylakoid membranes extracted from plants, and artificially synthesized membranes and protein complexes with photosynthetic functions, etc., can be cited as examples. For example, *Spirulina*, which is a blue-green algae, *Selenastrum*, which is a green algae, *Isochrysis*, which is a golden algae, and a thylakoid membrane, extracted from spinach, etc., can be used favorably.

Example 1

Figure 9:
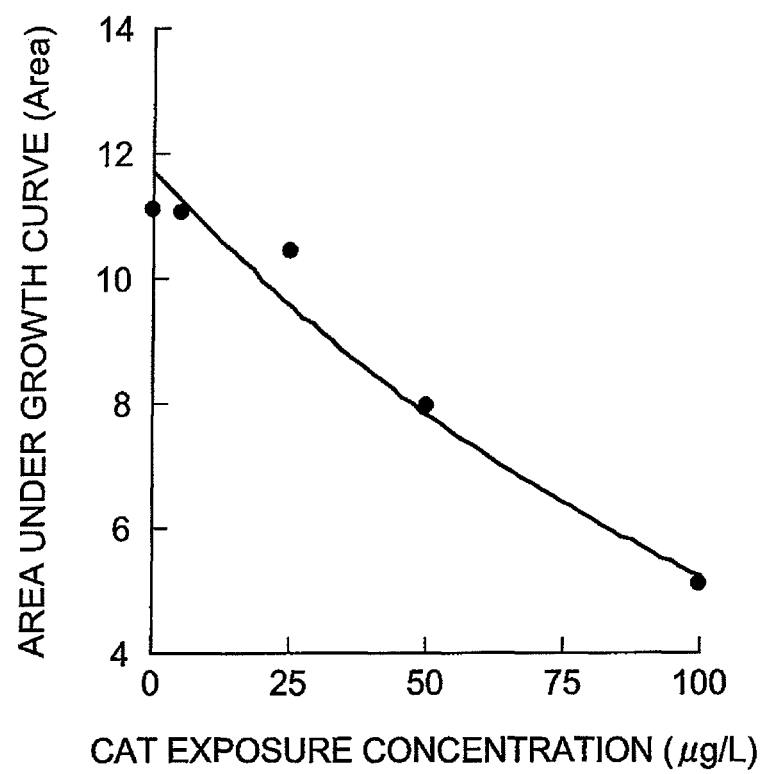
FIG. 9 is a graph of an area under a growth curve of *S. platensis* in a case of exposure to simazine of different concentrations.

In Example 1, the herbicide, simazine (CAT), was used as the environmental factor to be evaluated. The algae, *Spirulina platensis* (blue-green algae), was used as the plant sample that emits delayed luminescence. Simazine is an environmental factor that is a harmful substance for *S. platensis*. FIG. 9 shows a variation of an area under a growth curve of *S. platensis* when exposed to various concentrations of simazine. In the graph of FIG. 9, an abscissa indicates the simazine concentration and an ordinate indicates the area under the growth curve.

The area under the growth curve indicates cell growth, which is a conventional evaluation index of chemical substance impact on algae and is computed in compliance to a method for evaluating the impact of a chemical substance on a general algae (OECD Test Guideline 201). That is, the area under the growth curve is the area under the growth curve obtained by culturing 6 mL of an *S. platensis* cell suspension, adjusted to have an absorbance at 750 nm of 0.03, under a white fluorescent lamp (50 $\mu$mol·m−2·s−1) for 72 hours after chemical substance exposure and measuring, every 24 hours, a cell density as the absorbance at 750 nm. As shown in FIG. 9, it can be understood that cell growth of *S. platensis* 72 hours after exposure is inhibited according to the exposure concentration of simazine.

In the present example, the measurement of delayed luminescence was carried out as follows. 2.5 mL of an *S. platensis* cell suspension, adjusted to have an absorbance at 660 nm of 0.05 in a general, 10×10 mm spectrometric cell, was exposed to simazine of any of various concentrations and left to stand for 15 minutes under a white fluorescent lamp of a light amount of 50 $\mu$mol·m−2·s−1. Thereafter, inside the measuring device 10, a red light (660 nm) of approximately 300 $\mu$mol·m−2·s−1 was illuminated for 10 seconds from the light source 18 as the excitation light for making delayed luminescence be emitted and then the delayed luminescence emitted after extinguishing of the excitation light was recorded for 50 seconds at 0.1 second intervals.

FIG. 10 shows a result of measuring, for 50 seconds, the variation of the luminescence amount of delayed luminescence emitted from *S. platensis* 15 minutes after exposure to simazine. In the graph of FIG. 10, the abscissa indicates the time from the start of measurement (time after exposure) and the ordinate indicates the luminescence amount (counted number of photons). In the figure, "Not exposed" indicates the variation of the delayed luminescence obtained from algae in a state of not being exposed to simazine, and "Exposed" indicates the variation of the delayed luminescence obtained from algae in a state of being exposed to simazine. The "Not exposed" measurement results are for generating the reference data in the above-described embodiment. Presence/non-presence of influence due to simazine is the only difference between the "Exposed" and "Not exposed" cases. It can be understood that in each "Exposed" case, due to the influence of simazine, the luminescence amount increases at an early time period (near 0 seconds) of time after excitation and the luminescence amount decreases at a later time period (5 seconds onward).

The luminescence amount of delayed luminescence of *S. platensis* decreases until around 15 seconds after excitation, and then re-increases around 20 seconds, and then decreases further thereafter. The increase of the luminescence amount around 20 seconds is due to storage and re-emission of energy by chemical reactions inside *S. platensis* cells under the measurement conditions of the present example. It is thus shown that under the measurement conditions of the present example, *S. platensis* stores a large amount of energy in a late stage of photosynthesis that influences the delayed luminescence at a late time period of time elapsed after excitation.

Figure 11:
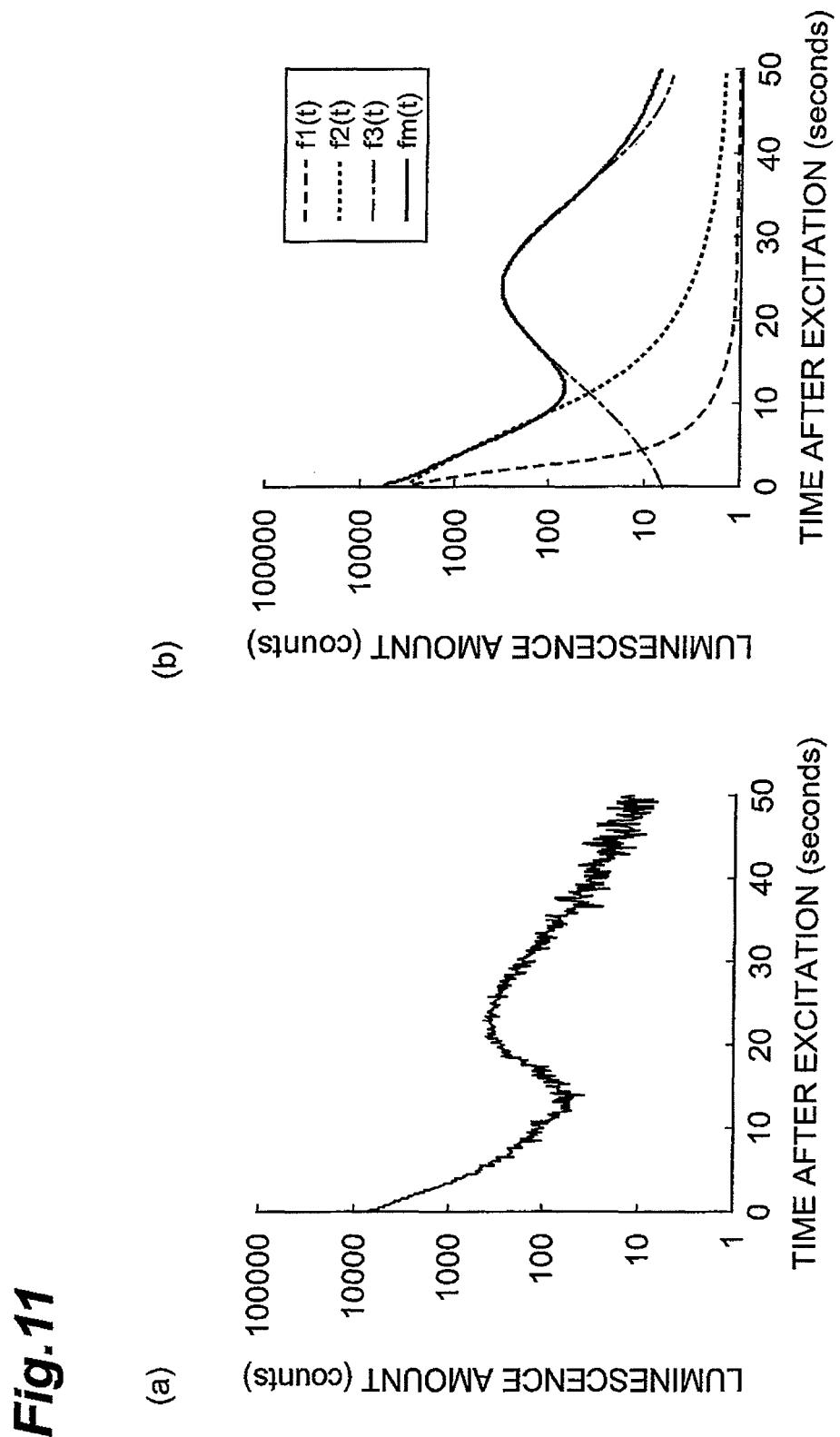
FIG. 11 shows graphs of an example of a fitting result in Example 1.

In the present example, the above-described Formula (1) was used for fitting. As examples for description of the fitting results, the measurement result for the "Not exposed" case is shown in FIG. 11A and a graph of the results of fitting to the measurement data are shown in FIG. 11B. In FIG. 11B, $f1(t)$, $f2(t)$, and $f3(t)$ are respectively the first function, the second function, and the third function in Formula (1). From FIG. 11, it can be understood that the delayed luminescence measurement data can be fitted by a plurality of hill-shaped functions.

By the fitting, the function coefficients, $a_i$, $b_i$, and $c_i$ ($i=1, 2, 3$) are determined. The results are shown in the table below.

TABLE 1

|  | Simazine exposure concentration μg/L | $a_1$ | $b_1$ | $c_1$ | $a_2$ | $b_2$ | $c_2$ | $a_3$ | $b_3$ | $c_3$ |
|---|---|---|---|---|---|---|---|---|---|---|
| Not exposed | 0 | 0.1 | −0.5 | 3.6 | 0.009 | −0.5 | 3.45 | 0.0038 | 24 | 2.5 |
| Exposed | 5 | 0.2 | −0.5 | 4.5 | 0.01 | −0.5 | 3.5 | 0.006 | 22 | 2.2 |
|  | 25 | 0.2 | −0.5 | 4.8 | 0.018 | −0.5 | 3.8 | 0.005 | 22 | 1.6 |
|  | 50 | 0.3 | −0.5 | 5 | 0.02 | −0.5 | 3.8 | 0.01 | 21 | 1.2 |
|  | 100 | 0.4 | −0.5 | 5.5 | 0.024 | −0.5 | 3.8 | 0.02 | 20 | 0.7 |

In Example 1, a coefficient value is used as the evaluation value.

As an example of the evaluating step, a case of using c3, which, among the coefficients shown in the above table, is a coefficient of the third function $f3(t)$, shall now be described. In Formula (1), the third function is the function with which the time of maximum value of the luminescence amount is the largest and, among the first to third functions in the present example, is considered to reflect energy stored for the longest duration inside the cells. In this function, the coefficient value c3 is a value related to the height of the hill-shaped function and is most deeply related to the luminescence amount of the photon component expressed by the third function.

Figure 12:
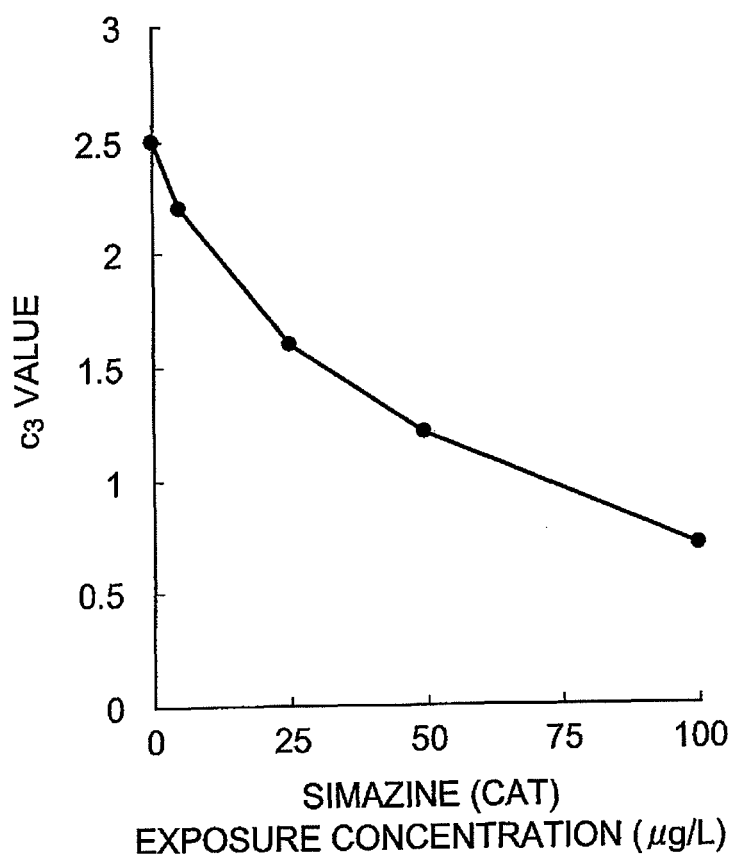
FIG. 12 is a graph of a relationship of the simazine exposure concentration and a value of c3, which is a coefficient value determined by fitting in Example 1.

A variation of the value of c3 with the simazine exposure concentration is shown in FIG. 12. In the graph of FIG. 12, the abscissa indicates the simazine exposure concentration and the ordinate indicates the value of c3. As shown in FIG. 12, the evaluation value with respect to the temporal data of the luminescence amount of delayed luminescence of *S. platensis* decreases in accordance with the simazine exposure concentration and the decrease is correlated with the cell growth after 72 hours shown in FIG. 9. This comparison result can thus be used as the evaluation result.

Thus in the case of using *S. platensis* as the plant sample, the environmental impact of the environmental factor can be evaluated by using the coefficient value obtained as a result of fitting. The environmental impact of the environmental factor is the inhibition of algae growth that is brought about by the influence of simazine.

Example 2

Figure 13:
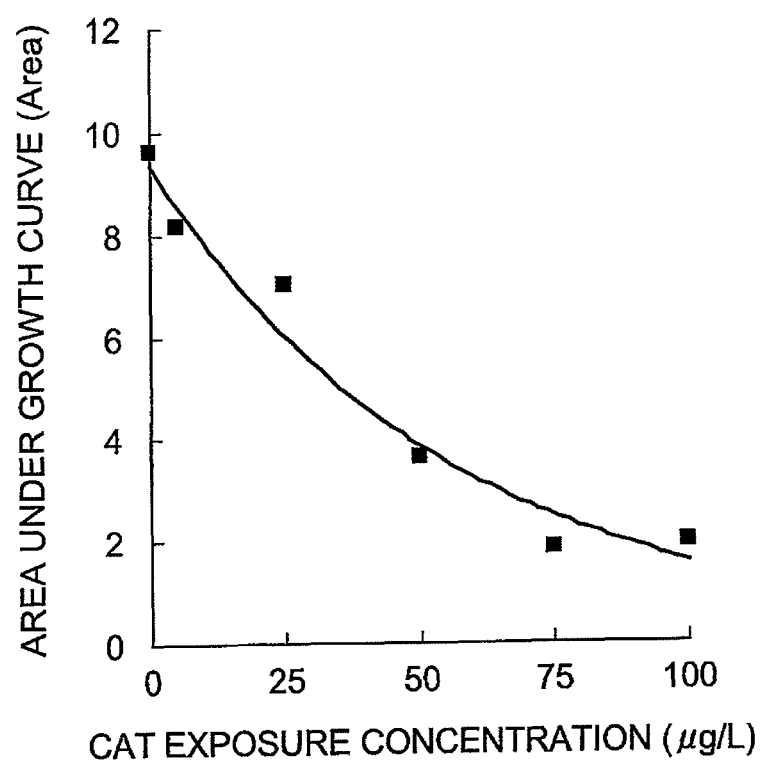
FIG. 13 is a graph of an area under a growth curve of *P. subcapitata* in a case of exposure to simazine of different concentrations.

The herbicide, simazine (CAT), was used as the environmental factor to be evaluated in Example 2 as well. The algae, *Pseudokircheneriella subcapitata* (green algae), was used as the plant sample that emits delayed luminescence. Simazine is an environmental factor that is a harmful substance for *P. subcapitata*. FIG. 13 shows the variation of the area under the growth curve of *P. subcapitata* when exposed to various concentrations of simazine. In the graph of FIG. 13, the abscissa indicates the simazine concentration and the ordinate indicates the area under the growth curve.

In the present embodiment, the area under the growth curve is the area under the growth curve obtained by culturing 6 mL of an *P. subcapitata* cell suspension, adjusted to have an absorbance at 750 nm of 0.01, under a white fluorescent lamp (50 μmol·m−2·s−1) for 72 hours after chemical substance exposure and measuring, every 24 hours, the cell density as the absorbance at 750 nm. As shown in FIG. 13, it can be understood that cell growth of *P. subcapitata* 72 hours after exposure is inhibited according to the exposure concentration of simazine.

In the present example, the measurement of delayed luminescence was carried out as follows. 2.5 mL of a *P. subcapitata* cell suspension, adjusted to have an absorbance at 660 nm of 0.2 in a general, 10×10 mm spectrometric cell, was exposed to simazine of any of various concentrations and left to stand for 15 minutes under a white fluorescent lamp of a light amount of 50 μmol·m−2·s−1. Thereafter, inside the measuring device 10, a red light (660 nm) of approximately 300 μmol·m−2·s−1 was illuminated for 10 seconds from the light source 18 as the excitation light for making delayed luminescence be emitted and then the delayed luminescence emitted after extinguishing of the excitation light was recorded for 50 seconds at 0.1 second intervals.

Figure 14:
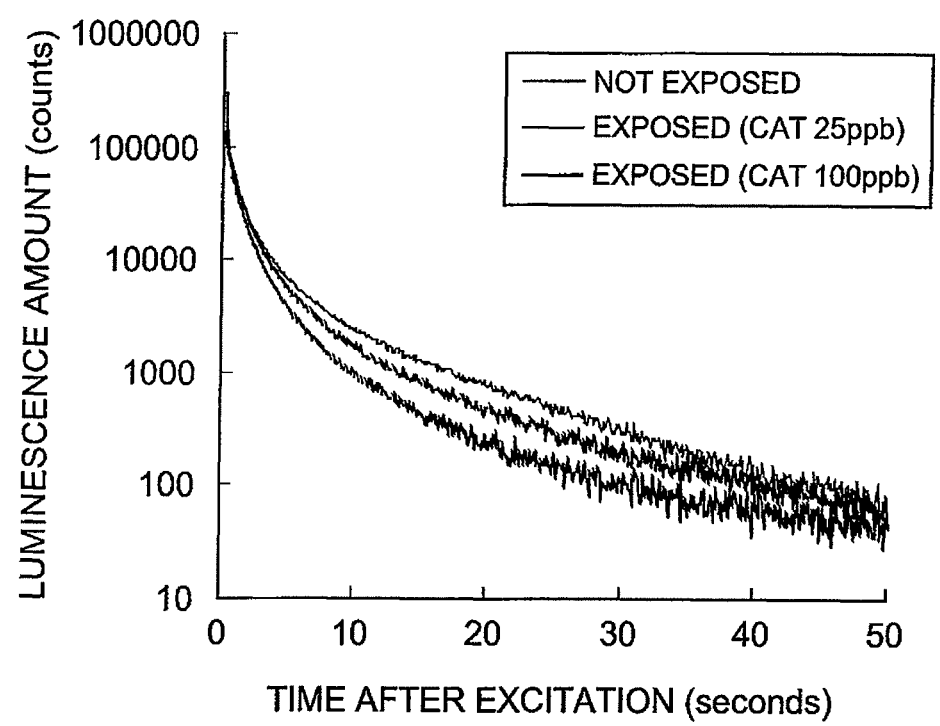
FIG. 14 is a graph of luminescence amounts of delayed luminescence emitted from *P. subcapitata* (plant sample) in Example 2.

FIG. 14 shows a result of measuring, for 50 seconds, the variation of the luminescence amount of delayed luminescence emitted from *P. subcapitata* 15 minutes after exposure to simazine. In the graph of FIG. 14, the abscissa indicates the time from the start of measurement (time after exposure) and the ordinate indicates the luminescence amount (counted number of photons). It can be understood that in each "Exposed" case, due to the influence of simazine, the luminescence amount increases at an early time period (near 0 seconds) of time after excitation and the luminescence amount decreases at a later time period (5 seconds onward).

In the present example, the above-described Formula (1) was used for fitting. As examples for description of the fitting results, the measurement result for the "Not exposed" case is shown in FIG. 15A and a graph of the results of fitting to the measurement data are shown in FIG. 15B. In FIG. 15B, $f1(t)$, $f2(t)$, and $f3(t)$ are respectively the first function, the second function, and the third function in Formula (1). From FIG. 15, it can be understood that the delayed luminescence measurement data can be fitted by a plurality of hill-shaped function.

By the fitting, the function coefficients, $a_i$, $b_i$, and $c_i$ ($i=1, 2, 3$) are determined. The results are shown in the table below.

TABLE 2

| | Simazine exposure concentration μg/L | Fitting formula values | | | | | | | | |
|---|---|---|---|---|---|---|---|---|---|---|
| | | $a_1$ | $b_1$ | $c_1$ | $a_2$ | $b_2$ | $c_2$ | $a_3$ | $b_3$ | $c_3$ |
| Not exposed | 0 | 0.045 | −0.5 | 5.1 | 0.003 | −0.5 | 4.1 | 0.0005 | 8 | 3.1 |
| Exposed | 5 | 0.05 | −0.5 | 5.2 | 0.0037 | −0.5 | 4.15 | 0.0005 | 6 | 3 |
| | 25 | 0.05 | −0.5 | 5.2 | 0.0035 | −0.5 | 4.1 | 0.0004 | 5 | 2.9 |
| | 50 | 0.08 | −0.5 | 5.4 | 0.0044 | −0.5 | 4.1 | 0.0005 | 3 | 2.9 |
| | 100 | 0.1 | −0.5 | 5.6 | 0.005 | −0.5 | 4.1 | 0.005 | 3 | 2.7 |

In Example 1, a coefficient value and computed values, computed from the coefficient values, are used as the evaluation values.

As an example of the evaluating step, a case of using $c_3$, which, among the coefficients shown in the above table, is a coefficient of the third function $f3(t)$, shall now be described. In Formula (1), the third function is the function with which the time of maximum value of the luminescence amount is the largest and, among the first to third functions in the present example, is considered to reflect energy stored for the longest duration inside the cells. In this function, the coefficient value $c_3$ is the value related to the height of the hill-shaped function and is most deeply related to the luminescence amount of the photon component expressed by the third function.

Figure 16:
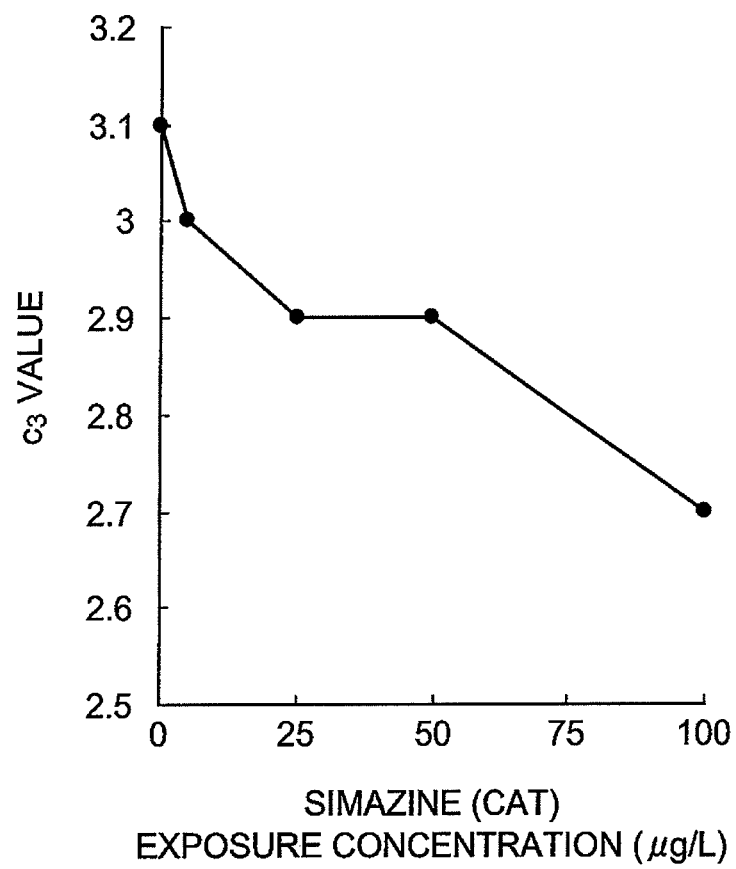
FIG. 16 is a graph of a relationship of the simazine exposure concentration and the value of c3, which is the coefficient value determined by fitting in Example 2.

A variation of the value of $c_3$ with the simazine exposure concentration is shown in FIG. 16. In the graph of FIG. 16, the abscissa indicates the simazine exposure concentration and the ordinate indicates the value of $c_3$. As shown in FIG. 16, the evaluation value with respect to the temporal data of the luminescence amount of delayed luminescence of *P. subcapitata* decreases in accordance with the simazine exposure concentration and the decrease is correlated with the cell growth after 72 hours shown in FIG. 13. This comparison result can thus be used as the evaluation result.

Thus even in the case of using *P. subcapitata* as the plant sample, the environmental impact of the environmental factor can be evaluated by using the coefficient value obtained as a result of fitting. In this example, the environmental impact of the environmental factor is the inhibition of algae growth that is brought about by the influence of simazine.

As another example of the evaluating step, a case of evaluating by an evaluation value computed based on a computation formula shall be described. As the evaluation value, an evaluation value E is computed from the determined coefficient values $a_i$, $b_i$, and $c_i$ ($i=1, 2, 3$) and based on Formula (2) described above. Here, the constants $m_j$ ($j=1$ to 9) are set, for example, so that $m_1=1/a_3$, $m_2=1$, $m_3=1$, $m_4=1/a_2$, $m_5=1/b_2$, $m_6=1/c_2$, $m_7=1$, $m_8=1/a_1$, $m_9=1/c_1$. As the constants $m_j$, those that are appropriate according to the measurement conditions and algae species can be set. If instead of using all of the coefficient values, only a portion is to be used as described above, a reciprocal of a coefficient value, such as $1/a_3$, is set to the corresponding $m_j$ ($j=1$ to 9) for each coefficient value to be ignored.

The evaluation values determined by the above computation formula are shown in the following table and in FIG. 17.

TABLE 3

| | Simazine exposure concentration μg/L | Computed value E |
|---|---|---|
| Not exposed | 0 | 551.11 |
| Exposed | 5 | 360 |
| | 25 | 290 |

TABLE 3-continued

| | Simazine exposure concentration μg/L | Computed value E |
|---|---|---|
| | 50 | 108.75 |
| | 100 | 81 |

Figure 17:
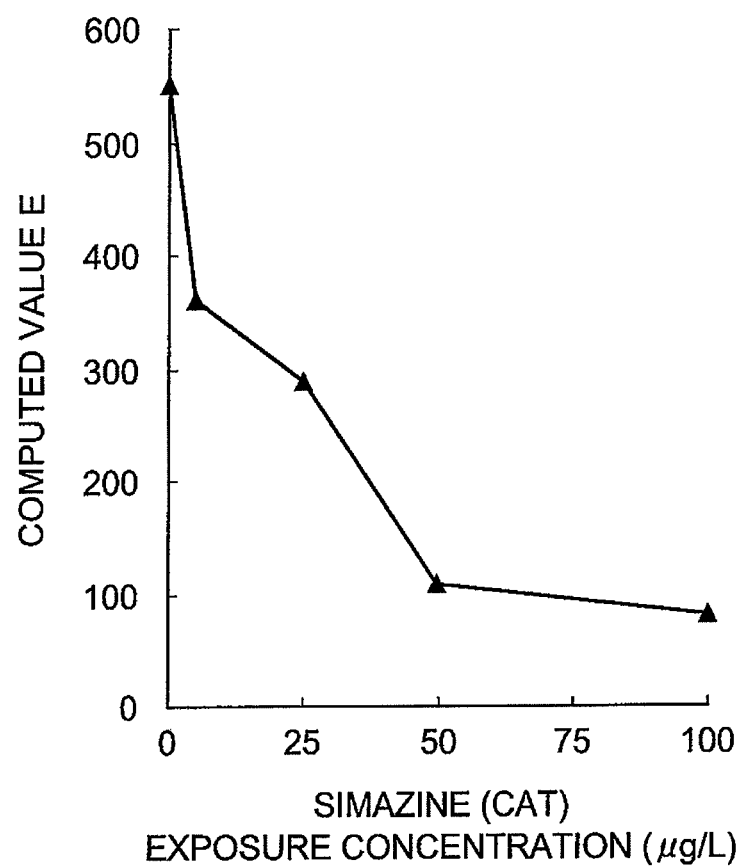
FIG. 17 is a graph of a relationship of the simazine exposure concentration and a value of an evaluation value E in Example 2.

In the graph of FIG. 17, the abscissa indicates the simazine exposure concentration and the ordinate indicates the value of the computed value E. As shown in FIG. 17, the evaluation value for the temporal data of the luminescence amount of delayed luminescence of *P. subcapitata* decreases in accordance with the simazine exposure concentration and the decrease is correlated with the cell growth after 72 hours shown in FIG. 12. This comparison result can thus be used as the evaluation result.

As another example of the evaluating step, a case of evaluating by an area value computed based on the coefficient values of a function shall be described. As mentioned above, the area value is the value of the area of a region surrounded by the curve indicating the function value in the function graph and the time axis line positioned below the curve indicating the function value. The area value of a function is deeply related to the luminescence amount of the photon component expressed by the function. In the present example, based on the coefficient values obtained from the results of exposing simazine to *P. subcapitata* shown in Table 2, area values were determined for the third function $f3(t)$ in Formula (1) in a range of $t=0$ to 90 by quadrature by parts with at interval $\Delta t$ being set equal to 0.1.

The area values thus determined are shown in the following table and in FIG. 18.

TABLE 4

| | Simazine exposure concentration μg/L | Area value (quadrature by parts) |
|---|---|---|
| Not exposed | 0 | 29226.4 |
| Exposed | 5 | 24112.1 |
| | 25 | 19665.7 |
| | 50 | 16520.1 |
| | 100 | 4435.7 |

Figure 18:
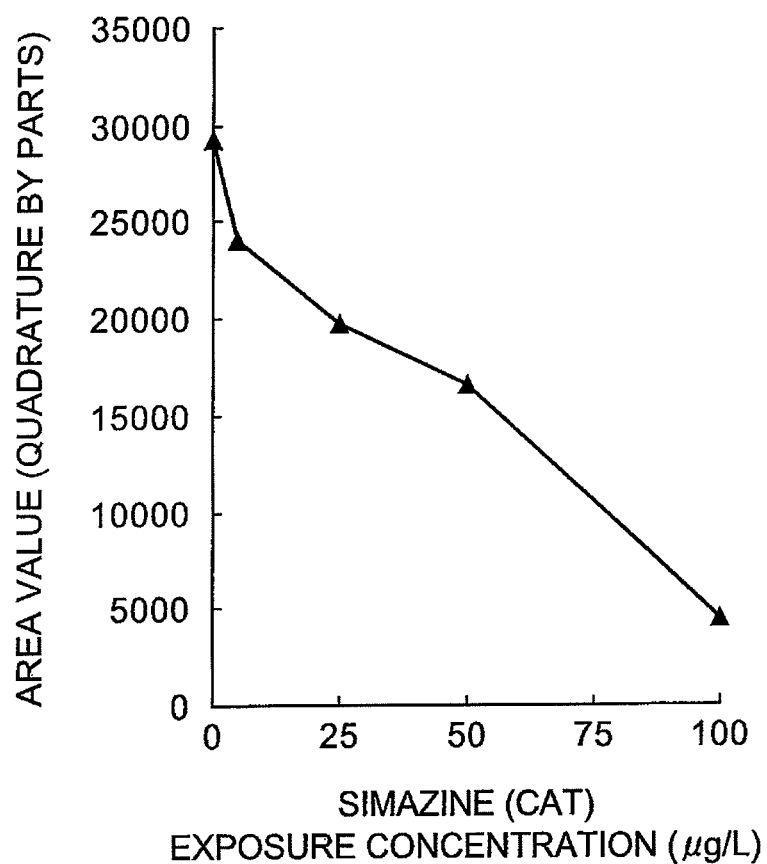
FIG. 18 is a graph of a relationship of the simazine exposure concentration and an area in Example 2.

In the graph of FIG. 18, the abscissa indicates the simazine exposure concentration and the ordinate indicates the area value. As shown in FIG. 18, the area value with respect to the temporal data of the luminescence amount of delayed luminescence of *P. subcapitata* decreases in accordance with the simazine exposure concentration and the decrease is correlated with the cell growth after 72 hours shown in FIG. 12. This comparison result can thus be used as the evaluation result.

Besides the above computation methods, the coefficient values of the respective functions of Formula (1) may be weighted so that the coefficient values of the second function f2(t) and the coefficient values of the third function f3(t) of Formula (1) are more greatly reflected in the evaluation value than the coefficient values of the first function f1(t) of the same formula. For example, the coefficient values of the respective functions can be weighted so that the evaluation value is computed just by the coefficient values of the second function f2(t) and the coefficient values of the third function f3(t). That is, the evaluation sample may be, evaluated by weighting so that, among the characteristic values respectively corresponding to the plurality of time periods in the temporal data, the characteristic values corresponding to time periods other than a time period that includes a time immediately after excitation (for example, in a range of t=0 to 0.5) are more greatly reflected in the evaluation value than the characteristic values of the time period including the time immediately after excitation.

Here, the characteristic values refers to values that indicate the characteristics of the respective time periods in the temporal data. In a case where the temporal data of delayed luminescence are to be fitted as a sum of a plurality of functions, the coefficient values of each function express characteristics of a time period of the temporal data.

When the temporal data of delayed luminescence are fitted as the sum of functions, there appears a time period, with which a specific function has a large influence on the temporal data. In such a time period, the coefficient values of the function of large influence on the temporal data are considered to express the characteristics of the time period. For example, with the fitting example for *P. subcapitata* shown in FIG. 15, the first function f1(t) has a large influence on the temporal data in a time period immediately after excitation (around 0 to 1 second), the second function f2(t) has a large influence on the temporal data around 1 to 15 seconds after excitation, and the third function f3(t) has a large influence on the temporal data around 15 to 50 seconds after excitation. The coefficient values of the respective functions can thus be deemed to be the characteristic values of the respective time periods. The method for computing the characteristic values by fitting is not restricted to the present method and various methods can be considered according to a shape of the temporal data and the type of functions used in fitting.

The present inventors found that by weighting so that, among the plurality of characteristic values of the temporal data, the characteristic values, corresponding to the time period other than the time period including the time immediately after excitation, are more greatly reflected in the evaluation value, a difference between the evaluation value and the basic data for evaluating the evaluation sample appears more clearly. The present inventors also found that the environmental impact, for example, of a chemical substance can thereby be ascertained more clearly. That is, by performing such weighting, a photosynthetic sample can be evaluated more appropriately. This weighting method is one example and the characteristic values of any time period may be made to be greatly reflected in the evaluation value according to the state of the photosynthetic sample.

Second Embodiment

A second embodiment of the present invention shall now be described with reference to the attached drawings.

Theoretical Background

Figure 19:
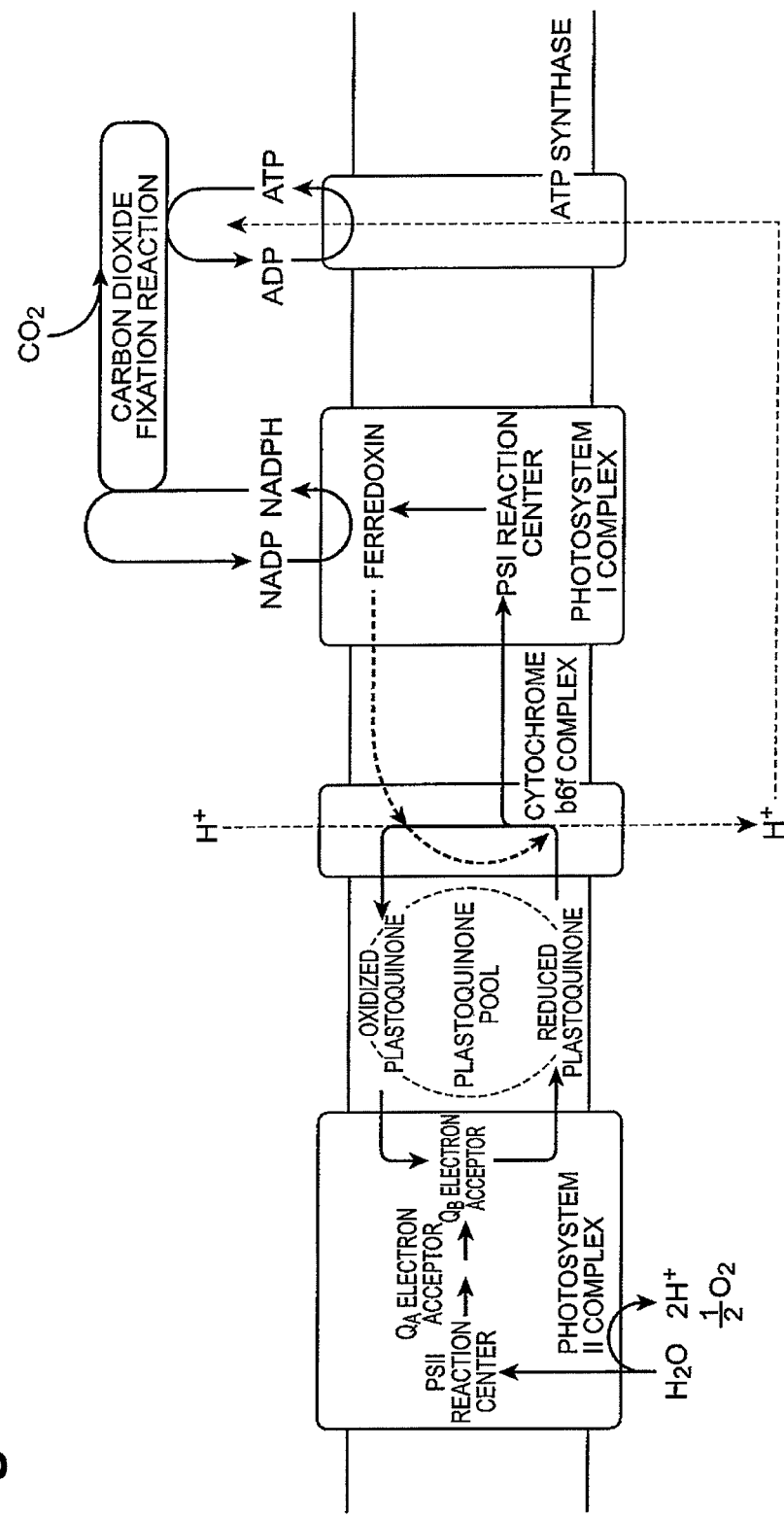
FIG. 19 is a schematic view of photosynthetic electron transport.

First, photosynthetic electron transport, which is a theoretical background of an evaluation method for photosynthetic sample according to the present invention, shall be described using FIG. 19. FIG. 19 is a schematic view of photosynthetic electron transport.

In general, when a photosynthetic sample with a photosynthetic function absorbs a large amount of light energy, because rate limitation occurs in each individual reaction in the photosynthetic electron transport system, the photosynthetic electron transport does not proceed smoothly. In other words, a redox state of the photosynthetic sample becomes a state that differs from a normal state. Such a state can be obtained by changing light conditions provided to the photosynthetic sample. Here, the light conditions refer to a light amount, wavelength, pulse width, and illumination duration of light provided to the photosynthetic sample. In the present specification, the state where the photosynthetic electron transport does not proceed smoothly (the state where the redox state of the photosynthetic sample becomes a state that differs from normal) shall be referred to as "saturation." Meanwhile, the state where the photosynthetic electron transport proceeds smoothly (the state where the redox state of the photosynthetic sample is normal) shall be referred to as "non-saturation."

As shown in FIG. 19, a photosynthetic reaction of a photosynthetic sample is carried out as a carbon dioxide fixation reaction (Calvin-Benson cycle) that mainly uses a reduced substance (NADPH), produced by a photosystem II complex (PSII), a cytochrome b6f complex (cytb6f), a photosystem I complex (PSI), and ATP synthase, which are present in a chloroplast thylakoid membrane, and the ATP synthase.

First, the PSII and the PSI absorb light and perform electron transport reactions. Specifically, when light is illuminated, a water molecule ($H_2O$) is broken down in the PSII and an electron (e-) is taken out. This electron is transported from a PSII reaction center (P680) via a QA electron acceptor (QA) to an oxidized plastoquinone (pQOX) bonded to a QB electron acceptor (QB). A reduced plastoquinone (pQred) is thereby formed.

The reduced plastoquinone disengages from the QB site, moves to a plastoquinone pool (pQ pool), and is thereafter re-oxidized back to the oxidized plastoquinone by the cytb6f. In this process, a hydrogen ion ($H+$) flows into the thylakoid membrane via the cytb6f and forms a proton gradient. The hydrogen ion that forms the proton gradient is used in ATP synthesis by the ATP synthase. Meanwhile, the electron extracted in the process of reoxidation of the reduced plastoquinone is transported to a PSI reaction center (P700). In the PSI, this electron is transported from the P700 to the ferredoxin (Fd) and contributes to NADPH production. Excess electrons (reducing force) at the PSI onward are transported by cyclic electron transport via the Fd to the cytb6f and reduce the oxidized plastoquinone. Consequently, the reduced plastoquinone is formed (cyclic electron transport).

Although delayed luminescence is deemed to be luminescence that is mainly emitted by a reaction center chlorophyll of the PSII becoming re-excited chemically as a result of reverse reactions of the above photosynthetic electron transport reactions, it has also been reported that the PSI is also likewise involved in luminescence. It is understood that the electrons distributed inside the PSII, in the pQ pool, and the PSI onward are the principal components that contribute to the re-excitation of chlorophyll. Thus when a change occurs in the photosynthetic electron transport reactions due to an influence of an environmental factor (such as a harmful substance), a change appears in the delayed luminescence.

In general, electron transport capacities of the pQ pool, cyt6bf, and PSI are low compared to the electron transport capacity of the PSII. It is thus known that when the PSII becomes excessively reduced by light illumination, because the pQ pool then becomes excessively reduced due to electron transport from the PSII, the amount of the oxidized plastoquinone that receives electrons from the PSII decreases and the photosynthetic electron transport from the PSII lowers in efficiency. This phenomenon is one form of saturation of photosynthetic electron transport. More specifically, when the PSII absorbs light excessively, first, the reoxidation of the reduced plastoquinone by the cytb6f becomes rate limiting and the oxidized plastoquinone that can receive electrons from the PSII falls into shortage. Electron transport from the PSII to the cyt6bf thus stagnates. Consequently, electrons accumulate excessively inside the PSII and incur various influences on the photosynthesis reactions, such as destruction of the reaction center of the PSII. Such an influence is called photoinhibition.

It is known that various changes in metabolism, such as moving of a light-harvesting protein complex (LHC2), which inherently is for supplying electrons to the PSII, to the PSI (state transition), etc., occur to avoid such photoinhibition. Such changes in metabolism caused by the photoinhibition recover gradually when the excessive light illumination is stopped.

With the present invention, such changes in the redox state of photosynthetic electron transport are noted and an environmental factor applied to a photosynthetic sample is evaluated by measuring the delayed luminescence upon controlling illumination of excitation light.

Delayed Luminescence Measuring Device

Figure 20:
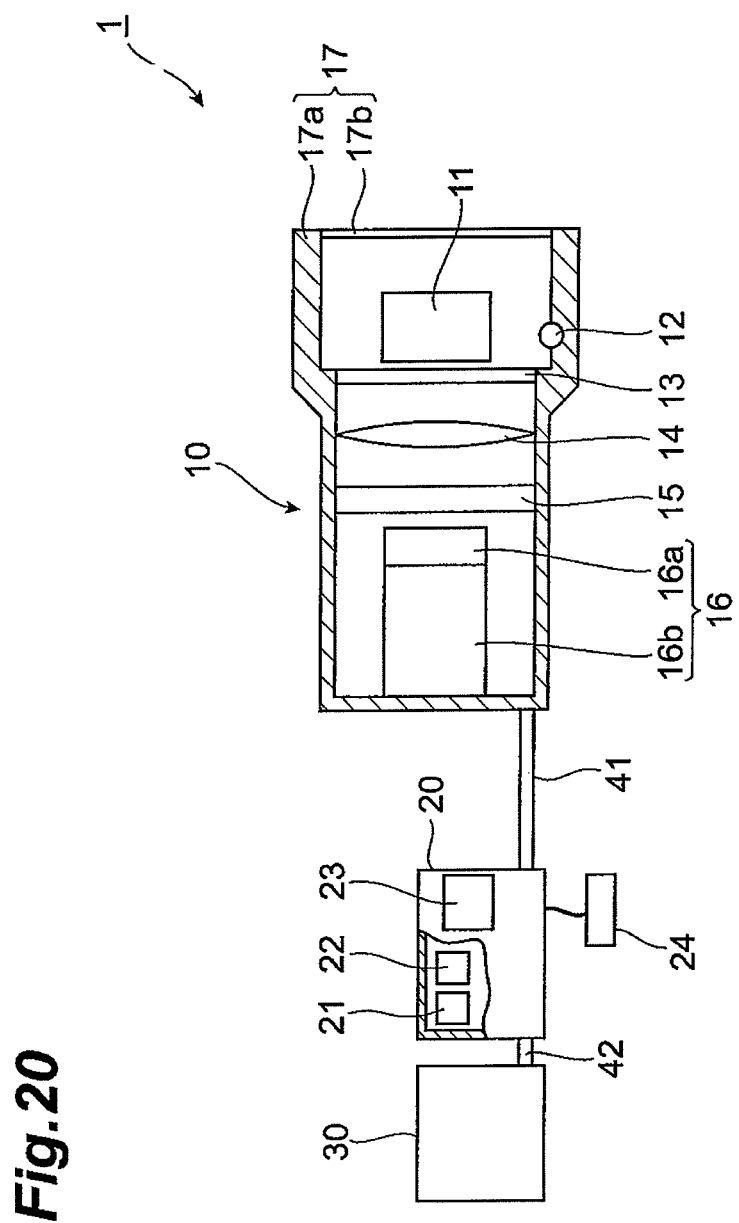
FIG. 20 is a schematic diagram of a delayed luminescence measuring device according to an embodiment.
Figure 21:
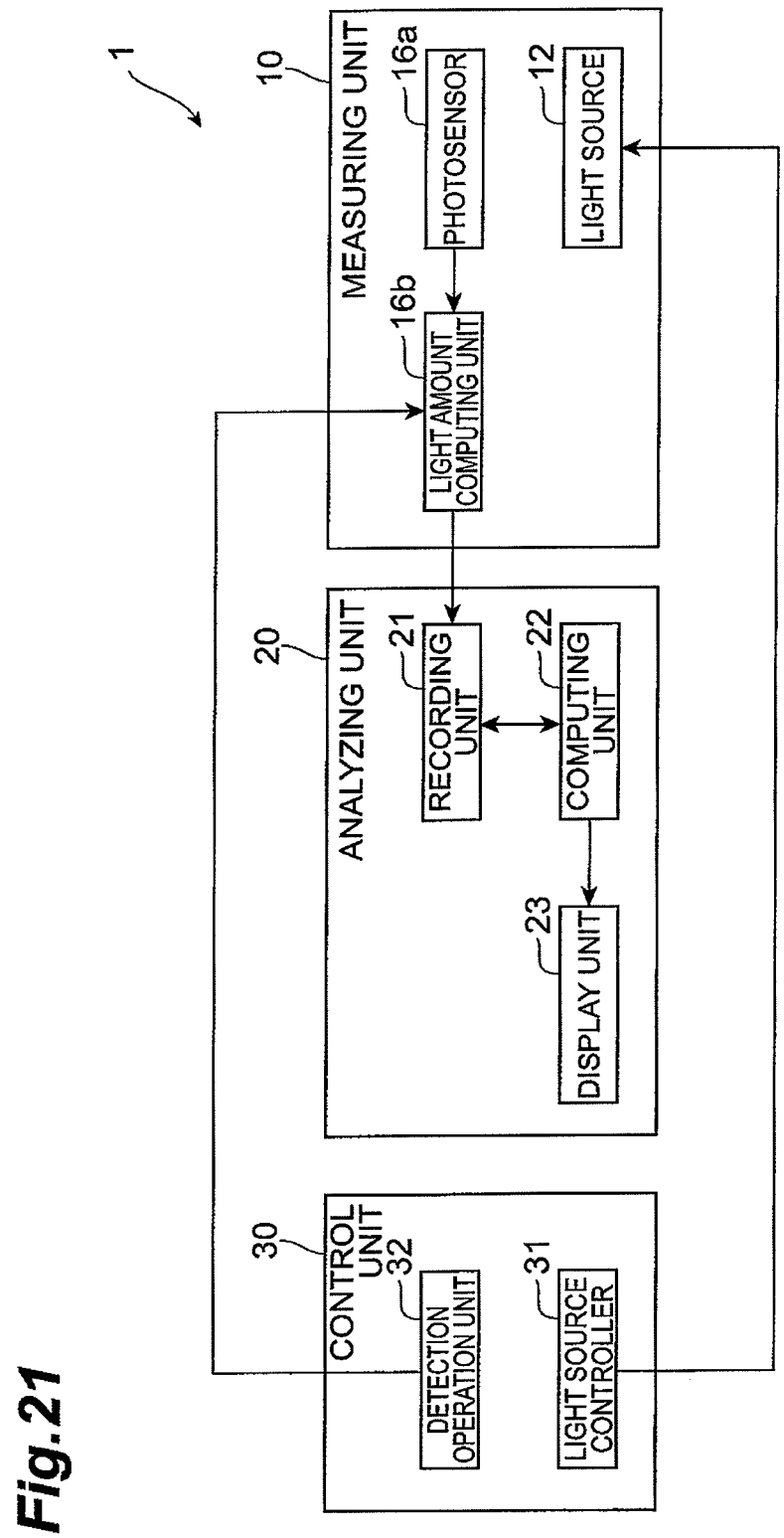
FIG. 21 is a partial block diagram of the delayed luminescence measuring device shown in FIG. 20.

First, a delayed luminescence measuring device for carrying out the evaluation method for photosynthesis sample according to the present invention shall be described using FIGS. 20 and 21. FIG. 20 is a schematic diagram of the delayed luminescence measuring device 1 according to the embodiment. FIG. 21 is a partial block diagram of the delayed luminescence measuring device 1 shown in FIG. 20.

The delayed luminescence measuring device 1 includes a measuring unit 10, an analyzing unit 20, and a control unit 30. The measuring unit 10 and the analyzing unit 20 are connected by a first cable 41, and the analyzing unit 20 and the control unit 30 are connected by a second cable 42.

The measuring unit 10 includes a sample setting unit 11, a light source 12, a filter 13, a focusing optical system 14, a shutter 15, and a detecting unit 16, and these components are housed in a casing 17. The casing 17 has a main unit 17a and a lid 17b.

The sample setting unit 11 is a portion for setting a sample to be measured. The sample setting unit 11 is configured to enable setting of a container containing the sample, and the sample can be exchanged by opening the lid 17b. The sample setting unit 11 may be configured to enable introduction of the sample from outside the casing 17 by means of a liquid delivery pump, etc.

The light source 12 illuminates light (excitation light) onto the sample set in the sample setting unit 11. It suffices that the light source 12 can emit light of wavelengths (280 to 800 nm) effective for photosynthesis by plants and, for example, a light emitting diode, a semiconductor laser device, or a light bulb is used. The light source 12 may be a monochromatic light source or a light source combining a plurality of light sources. The light source 12 is not restricted in light emission method, and for example, a method of emitting light continuously for a predetermined duration, a method of pulse lighting according to any pattern, a method of making a plurality of light sources with the same or different wavelength characteristics emit light sequentially, a method of making a plurality of light sources emit light simultaneously, etc., can be considered.

The filter 13 transmits the delayed luminescence and is disposed so as to contact an inner wall surface of the casing 17.

The focusing optical system 14 focuses the weak delayed luminescence that has been transmitted through the filter 13. The focusing optical system 14 is disposed so that the delayed luminescence focused thereby propagates to the detecting unit 16.

The shutter 15 is disposed in a manner enabling opening and closing. When the shutter 15 is closed, the delayed luminescence propagating from the focusing optical system 14 to the detecting unit 16 is blocked. The shutter 15 may be disposed at a position closer to the light source 12 than the filter 13 and the focusing optical system 14. In this case, light emission (afterglow) from components of the focusing optical system, etc., due to the light from the light source 12 being made directly incident on the filter 13 and the focusing optical system 14, can be prevented.

The detecting unit 16 measures a light amount of delayed luminescence emitted from a photosynthetic sample in a sample due to the light illuminated from the light source 12 and sends the measurement result to the analyzing unit 20. The detecting unit 16 includes a photosensor 16a, detecting the delayed luminescence, and a light amount computing unit 16b, computing the light amount of delayed luminescence based on a signal output upon detection by the photosensor 16a. The detecting unit 16 is constituted, for example, of a photon counter, using a photomultiplier tube, or a weak light measuring device, using an avalanche photodiode, etc.

The analyzing unit 20 includes a recording unit 21, a computing unit 22, a display unit 23, and an input unit 24. The recording unit 21 records measurement results sent from the detecting unit 16 and data necessary for analysis or evaluation. The computing unit 22 performs computational analysis and evaluation based on the measurement results and data recorded in the recording unit 21. The display unit 23 performs display of the results of analysis and evaluation by the computing unit 22. The input unit 24 is an interface enabling input of data necessary for analysis.

The control unit 30 is enabled to control operations of the measuring unit 10 and the analyzing unit 20 and is configured by combining, for example, a computer, a timer, and a relay. In particular, the control unit 30 includes a light source controller 31 and a detection controller 32. The light source controller 31 is enabled to control light conditions (for example, an illumination timing, light amount, wavelength, pulse width, and illumination duration) of the excitation light illuminated from the light source 12. The detection controller 32 is enabled to control detection (measurement) of the luminescence amount of the delayed luminescence in a predetermined duration and controls, for example, a detection timing, detection duration, etc.

The configurations of the analyzing unit 20 and the control unit 30 are not restricted to the above, and for example, a single computer may have functions of both the analyzing unit 20 and the control unit 30.

Evaluation Method for Photosynthetic Sample

Figure 22:
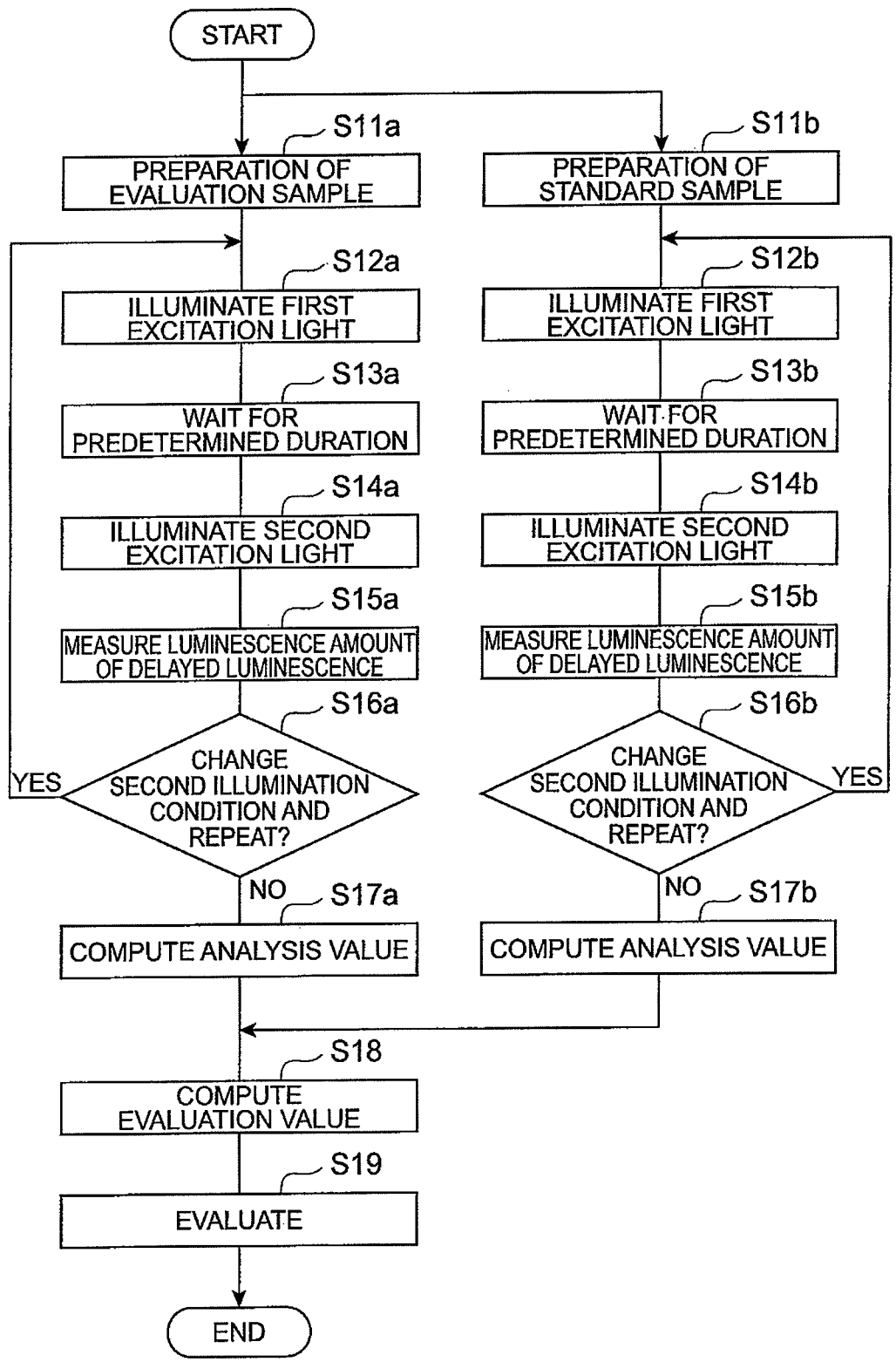
FIG. 22 is a flowchart of procedures of an evaluation method for photosynthetic sample.

Procedures of an evaluation method for photosynthetic sample using the delayed luminescence measuring device 1 shall now be described using FIG. 22. FIG. 22 is a flowchart of the procedures for the evaluation method for photosynthetic sample.

First, two types of sample containing a photosynthetic sample are prepared. Of these, one is a standard sample, with which an amount of photosynthetic sample, a light amount or wavelength of light illuminated onto the photosynthetic sample, temperature, composition of a buffer solution, exposure to a chemical substance, and other environmental conditions are set to predetermined conditions (step S11b). The other sample is an evaluation sample, with which at least one condition among the environmental conditions (addition of a harmful substance or temperature, etc.,) or conditions (growth conditions, etc.,) of the photosynthetic sample itself is differed from that of the standard sample (step S11a). Each of the prepared standard sample and the evaluation sample is contained in a cuvette or other container and left to stand or cultured as necessary under conditions of controlled temperature, light, etc., until an influence of a comparison condition for the photosynthetic sample becomes adequately apparent.

A first excitation light is then illuminated under a predetermined first illumination condition onto the evaluation sample, with which the influence of the comparison condition for the photosynthetic sample has become adequately apparent (step S12a, first excitation step). The light source controller 31 outputs a control signal to the light source 12 so that the excitation light illuminated from the light source 12 satisfies the first illumination condition. The first illumination condition refers to illuminating light of a predetermined light amount and a predetermined wavelength for just a predetermined duration so that the photosynthetic electron transport carried out in the photosynthetic sample becomes saturated. The excitation light illuminated from the light source 12 reaches the container set on the sample setting unit 11. The illumination, of the first excitation light is performed in likewise manner on the standard sample as well (step S12b; first excitation step).

The evaluation sample, illuminated by the first excitation light, is then made to wait for just a predetermined duration (no less than 0 seconds) under a predetermined light condition (step S13a; second excitation step). Specifically, the evaluation sample is made to wait under an environment where the light energy of light illuminated onto the evaluation sample is less than that of a second excitation light to be described below. For example, light is prevented from leaking from an exterior into an interior of the measuring unit 10, and the evaluation sample, set in the sample setting unit 11, is made to wait in darkness. Such waiting is carried out in likewise mariner with the standard sample as well (step S13b, second excitation step).

Next, using the light source 12, the second excitation light is illuminated under a second illumination condition onto the evaluation sample that was made to wait under the predetermined light condition (step S14a; second excitation step). The second illumination condition includes a condition such that a light energy integration value is less in comparison to the first illumination condition. Here, the energy integration value is the light energy integration value for the photosynthetic sample and is expressed as a product of a photon flux density ($\mu mol \cdot m-2 \cdot s-1$), an effective photosynthetic radiative absorption rate (%) of the photosynthetic sample, and the illumination duration (seconds). Such illumination of the second excitation light is performed likewise on the standard sample as well (step S14b; second excitation step).

A luminescence amount of delayed luminescence emitted from the evaluation sample illuminated with the second excitation light is then measured (step S15a; measuring step). The delayed luminescence emitted from the evaluation sample is transmitted through the filter 13 and is focused by the focusing optical system 14. The focused delayed luminescence is then sent to the detecting unit 16 and the luminescence amount of delayed luminescence is measured by the detecting unit 16. This measurement is performed at every predetermined time (for example, every 0.1 seconds) based on a control signal output from the detection controller 32 to the light amount computing unit 16b. Upon being associated with a measurement time and a measurement duration, the measured luminescence amount of delayed luminescence is output from the detecting unit 16 to the analyzing unit 20 and recorded in the recording unit 21. Such measurement is likewise made on the standard sample as well (step S15b; measuring step).

The above-described processes from the illumination of the first excitation light to the measurement of the luminescence amount of delayed luminescence are repeated a plurality of times with the second illumination condition being changed (step S16A:YES; step S16b:YES). Here, the second illumination condition includes, for example, an illumination starting timing of the second excitation light, in other words, a duration from a time of end of illumination of the first excitation light to a time of start of illumination of the second excitation light (hereinafter referred to as a "waiting time"). Such a second illumination condition is set by the light source controller 31. Because the redox state changes when the second illumination condition is changed, by applying the present measurement method, the luminescence amount of delayed luminescence under conditions that differ in redox state can be measured.

The number of times the processes from the illumination of the first excitation light to the measurement of the luminescence amount of delayed luminescence are repeated is not limited and any number of times may be set. Also, a plurality of comparison samples of the same conditions may be prepared and the delayed luminescence may be measured with the second illumination condition being changed for each sample. In this case, an influence of a previous measurement does not appear in the sample and a more accurate measurement can be made. Furthermore, the temporal data of the luminescence amount of delayed luminescence measured with the second illumination condition being changed or evaluation values based on the temporal data may be stored in advance in a storage unit. In this case, the measurement of delayed luminescence does not necessarily have to be repeated.

After the processes from the illumination of the first excitation light to the measurement of the luminescence amount of delayed luminescence have been repeated the plurality of times (step S16a: NO; step S16b: NO), analysis values that reflect the photosynthetic electron transport and other metabolism of the photosynthetic sample are computed from the measurement results obtained (step S17a and step S17b; evaluating step). This computation is performed on each of the evaluation sample and the standard sample. Specifically, the computing unit 22 computes the analysis values by applying the measurement results read from the recording unit 21 to a predetermined computing program. Examples of the analysis values include: integration values of the luminescence amount of delayed luminescence determined by integration according to one or more measurement time periods; a measurement duration (measurement time) at which a specific change appears in a process of decay of the luminescence amount of delayed luminescence; and coefficients obtained by fitting the temporal variation of the luminescence amount of delayed luminescence as a sum of functions.

Preferably, the sample is illuminated with just the second illumination light to measure the luminescence amount of delayed luminescence and the luminescence amount is used to compute the analysis values. In this case, because the luminescence amount of delayed luminescence for the case where the sample is not saturated is reflected in the analysis values, the photosynthetic function of the photosynthetic sample contained in the evaluation sample can be evaluated more appropriately. To compute the analysis value, all of the measurement results may be used or just a portion of the measurement results may be used.

It is especially preferable to use integration values, determined by integrating the measured luminescence amount of delayed luminescence according to each of one or more measurement time periods, as the analysis values. It thereby becomes possible to easily and appropriately extract a redox state of the photosynthetic sample at a certain measurement time period that appears in the temporal variation of the luminescence amount of delayed luminescence. Also, by setting up a plurality of measurement time periods and computing the integration value of each time period, it becomes possible to ascertain the temporal variation of the luminescence amount of delayed luminescence more appropriately and the redox state of the photosynthetic sample can thus be evaluated more appropriately.

Also preferably, the coefficient values of a plurality of priorly set functions derived so as to fit the measured temporal variation of the luminescence amount of delayed luminescence as a sum of the functions are used as the analysis values. By using such a mathematical method, an evaluation value can be derived objectively. Also, because the temporal variation of the luminescence amount of delayed luminescence is fitted to the sum of the functions, an evaluation based on the mechanism of delayed luminescence is enabled.

The above-described processes from preparation to analysis may be carried out simultaneously or at separate timings for the evaluation sample and the standard sample. Also in a case where standard data, described below, have been obtained, measurement of the standard sample does not performed necessarily.

Next, an evaluation value is computed (derived) based on the analysis values of the evaluation sample and the analysis values of the standard sample (step S18; evaluating step). As with the computation of the analysis values, the computation of the evaluation value is executed in the computing unit 22. The method for computing the evaluation value is not restricted to a single method. As an example, computing of the evaluation value by comparison of the analysis values for conditions of different redox states for the evaluation sample and standard sample respectively or by comparison of the analysis values of the evaluation sample and the analysis values of the standard sample, etc., can be cited. The evaluation values thus computed may be compared mutually to compute a further evaluation value. Furthermore, a method of using an analysis value as it is as the evaluation value, a method of using a result of adding, subtracting, multiplying, or dividing the analysis values as the evaluation value, or a method of substituting the analysis values in a predetermined function and using a computed result as the evaluation value may be employed. The computed evaluation value is not restricted in type and number.

Lastly, the state of the photosynthetic sample is evaluated based on the evaluation value obtained by computation (step S19; evaluating step). Specifically, the evaluation value obtained by computation is collated with the standard data to make an evaluation. As the standard data, an evaluation value obtained based on measurement data of the standard sample can be cited. A base value computed from an evaluation value of the standard sample may be used to evaluate the evaluation sample. As the base value, a threshold value, a range, etc., can be cited. The evaluation result concerning the state of the photosynthetic sample obtained here is indicated to an evaluator by being displayed on the display unit 23, etc. A method for indication to the evaluator is not restricted to this, and for example, the evaluation value may be indicated to the evaluator at a point at which the evaluation value is computed.

Background of the Present Embodiment

As a method for evaluating impacts on living organisms of unknown chemical substances present in the environment, biological toxicity inspection or "bioassay," by which growth inhibition of bacteria, algae, or other individual organisms is inspected, has been employed conventionally. As one type of bioassay, methods that make use of delayed fluorescence are known. For example, it is disclosed in Non-Patent Document 3 (Schmidt et. al.) that a luminescence pattern of delayed luminescence changes between a sample that has been left to stand in darkness before delayed luminescence measurement for two hours and a sample that has not been left to stand in darkness and that the luminescence pattern of delayed luminescence changes when a wavelength of light illuminated before the delayed luminescence measurement is changed.

An evaluation method for harmful substance that makes use of delayed fluorescence is also disclosed in Patent Document 1 (International Patent Publication No. 2005/062027 Pamphlet). With this evaluation method for harmful substance, first, a light amount of delayed fluorescence (delayed luminescence) from an aqueous solution sample containing a harmful substance and a light amount of delayed fluorescence from a comparison sample are measured respectively. Then based on each light amount of delayed fluorescence measured, an elapsed time at a characteristic point in a temporal variation of the light amount of delayed fluorescence is computed and by determining a comparison value of the elapsed time, the harmful substance present in the aqueous solution sample is evaluated. That the pattern of delayed luminescence changes when the light intensity or light wavelength of the light illuminated onto an object is changed is disclosed in this patent document as well.

However, with the above-described conventional evaluation methods, influences on reaction processes of a photosynthetic function of a photosynthetic sample are not evaluated appropriately. That is, even though influences on the overall photosynthetic function of a photosynthetic sample can be understood, it is difficult to evaluate influences on the respective reaction processes.

The present invention has been made to resolve the above issue and an object thereof is to provide an evaluation method for photosynthetic sample and an evaluation program for photosynthetic sample by which a photosynthetic function of a photosynthetic sample contained in an evaluation sample can be evaluated appropriately.

With this evaluation method for photosynthetic sample, because a luminescence amount of delayed luminescence can be measured according to different waiting times, more detailed evaluation values can be derived and consequently, a redox state of a photosynthetic sample contained in an evaluation sample can be evaluated appropriately.

(Measurement Example of Delayed Luminescence) A measurement of delayed luminescence performed with a redox state being changed shall now be described by way of a measurement example.

Here, a green algae (*Pseudokircheneriella subcapitata*) is used as the photosynthetic sample. The green algae was grown by rotation culture (120 rpm) using a standard C (75) medium (pH 7.5) under an environment of 25° C.±1° C. air temperature and illuminating white light of 50 µmol·m−2·s−1. The measurement sample is 2.5 mL of a cell suspension prepared by adjusting to a 685 nm absorbance OD685 of 0.05 using the C (75) medium as a diluent and thereafter culturing for 1 hour under an environment of 25° C.±1° C. air temperature while illuminating white light of 50 µmol·m−2·s−1. The measurement sample is then set still for 60 seconds in darkness before illuminating an excitation light and measuring a delayed luminescence. This is done to put the photosynthesis sample in a state in which photosynthetic electron transport proceeds smoothly (to maintain a redox state of the photosynthetic sample at a fixed state). Normally by setting still the measurement sample in darkness for 60 seconds, a state where the PSII, the pQ pool, and the PSI are adequately oxidized is attained.

For measurement of the delayed luminescence, the delayed luminescence, emitted from the measurement sample after excitation light illumination by light source 12, is detected by the detecting unit 16, and a detection signal is integrated each 0.1 seconds and output as a value (counts) correlated to the luminescence amount of delayed luminescence. This measurement is continued, for example, for 50 seconds after the excitation light is tuned off. In general, the luminescence amount of delayed luminescence after turning off of the excitation light decays with elapse of an elapsed time (time after excitation) from a point of time of ending of illumination of the excitation light.

Figure 23:
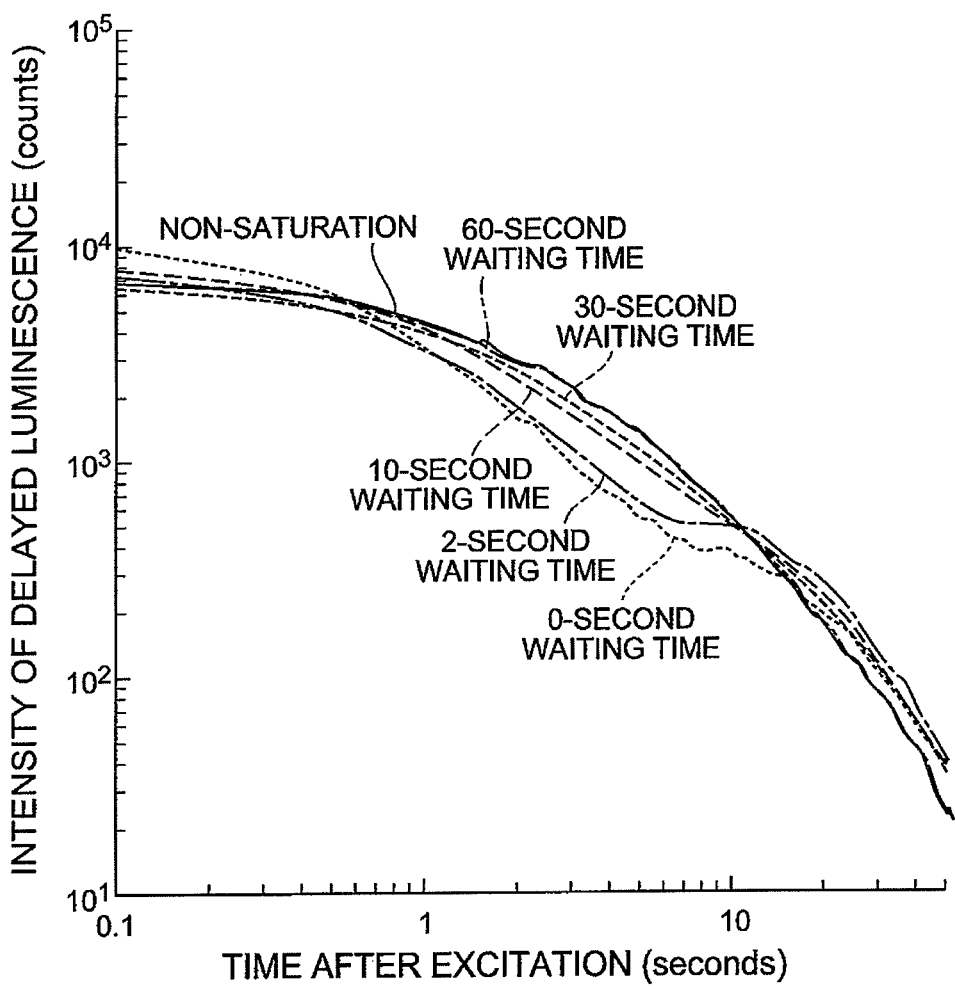
FIG. 23 is a graph of a relationship between a waiting time and a temporal variation of delayed luminescence.

First, a relationship between the waiting time and the temporal variation of delayed luminescence shall be described using FIG. 23. FIG. 23 is a graph of the relationship between the waiting time and the temporal variation of delayed luminescence. An abscissa of this graph expresses a time after excitation (elapsed time from the point of ending of illumination of the second excitation light) (seconds) and an ordinate expresses an intensity (counts) of the delayed luminescence. Because the delayed luminescence intensity is correlated to the luminescence amount of delayed luminescence, making an evaluation based on the delayed luminescence intensity in the following description is equivalent to making an evaluation based on the luminescence amount of delayed luminescence. In the following description, the graph plot of the relationship between the time after excitation and the intensity of delayed luminescence shall be referred to as the "decay curve."

In determining the relationship between the waiting time and the temporal variation of delayed luminescence, first, white light of 500 µmol·m−2·s−1 was illuminated for 10 seconds onto the measurement sample as the first excitation light for saturating photosynthetic electron transport (first illumination condition). Thereafter, a step of not illuminating light onto the measurement sample (referred to hereinafter as "waiting") was provided and then red light of 50 µmol·m−2·s−1 was illuminated for 2 seconds as the second excitation light. The second excitation light can make delayed luminescence be emitted while hardly changing the redox state of the photosynthetic sample. Such a process is performed repeatedly with the waiting being changed to 0, 2, 10, 30, and 60 seconds. In addition, measurement is also made for a case where the illumination of the first excitation light and waiting are not executed and just the illumination of the second excitation light is performed, that is, for the case where the photosynthetic electron transport is not saturated.

The graph of FIG. 23 shows the relationship between the waiting time and the temporal variation of delayed luminescence in each of the above cases. As shown in this graph, by combining the first excitation light illumination, the waiting, and the second excitation light illumination, states differing in the redox state of the photosynthetic sample can be realized in a stepwise manner to enable measurements of delayed luminescence that reflects the redox states. In the "Non-saturation" case where the first excitation light is not illuminated, the photosynthetic electron transport proceeds most smoothly. On the other hand, in the case where the second excitation light is illuminated immediately after illumination of the first excitation light (case where the waiting time is 0 seconds), the photosynthetic electron transport is most close to being saturated. As the waiting time becomes longer, the saturation of the photosynthetic electron transport becomes resolved (the photosynthetic electron transport system of the photosynthetic sample recovers).

The decay curve for the case of the waiting time of 0 seconds in FIG. 23 shows that the luminescence amount from 0.1 seconds to around 0.5 seconds after excitation is increased with respect to that of the non-saturation case, and oppositely, from around 0.5 seconds to around 10 seconds after excitation, the luminescence amount is decreased with respect to the non-saturation case. Also from around 10 seconds to 50 seconds after excitation, the luminescence amount is somewhat increased with respect to the non-saturation case. The decrease of the luminescence amount from around 10 seconds to 50 seconds after excitation with respect to the non-saturation case is slightly lessened in the case of the waiting time of 2 seconds. Such a change of the decay curve with respect to the non-saturation case lessens as the waiting time becomes longer, and hardly any difference can be seen between the decay curve for the case of the waiting time of 60 seconds and the decay curve for the non-saturation case. From this, it is considered that the saturation of the photosynthetic electron transport system is resolved within a waiting time of 60 seconds.

Grounds as to why the above measurement results are considered to express changes of the redox state of a photosynthetic sample shall now be described. As mentioned above, the redox state of a photosynthetic sample is determined by the light conditions of the illuminated excitation light, or more specifically, the light energy amount of the excitation light. Elements that determine the light energy amount include, for example, the illumination light amount and the illumination duration. Thus for description, first, relationships between the illumination light amount and the illumination duration and the temporal variation of delayed luminescence shall be described.

Figure 24:
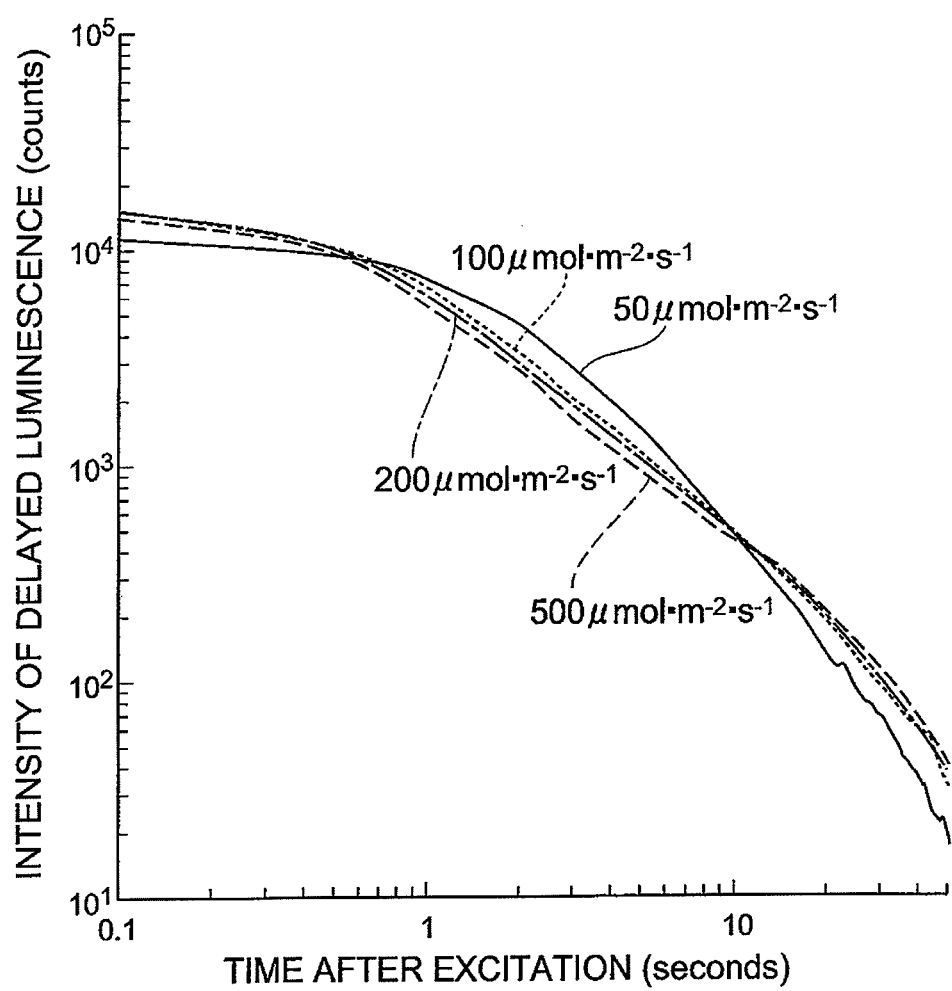
FIG. 24 is a graph of a relationship between an illumination light amount of an excitation light and the temporal variation of delayed luminescence.

FIG. 24 is a graph of a relationship between the illumination light amount of the excitation light and the temporal variation of delayed luminescence. The abscissa and ordinate of this graph express the same items as those of FIG. 23. To determine the relationship between the illumination light amount of the excitation light and the temporal variation of delayed luminescence, the above-described measurement was repeated with the illumination light amount of the first excitation light being changed to 50, 100, 200, and 500 µmol·m−2·s−1 (the waiting time was set to 0 seconds). In the case where the illumination light amount of the first excitation light is 50 µmol·m−2·s−1, saturation of the photosynthetic electron transport system does not occur. FIG. 24 shows that as the illumination light amount of the first excitation light lessens, the decay curve approaches that of the case of non-saturation (the case where the illumination light amount of the first excitation light is 50 µmol·m−2·s−1).

Figure 25:
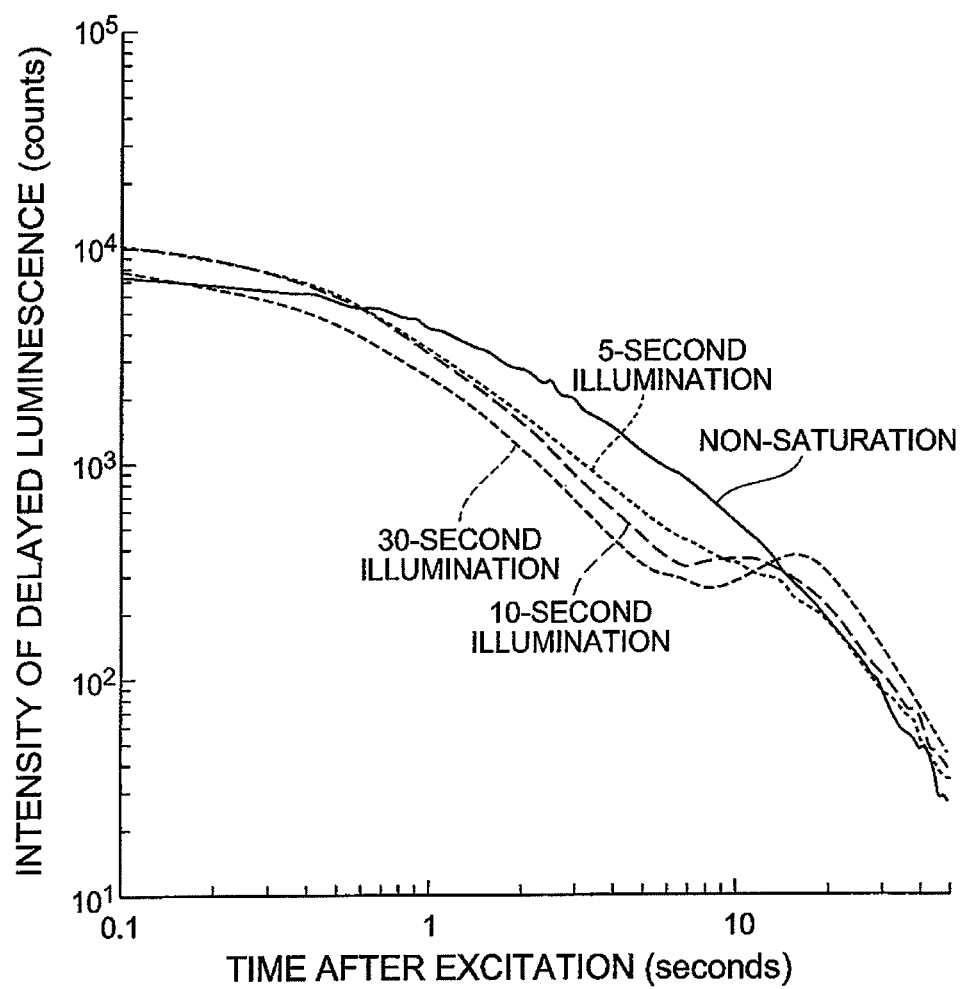
FIG. 25 is a graph of a relationship between an illumination duration of the excitation light and the temporal variation of delayed luminescence.

FIG. 25 is a graph of the relationship between the illumination duration of the excitation light and the temporal variation of delayed luminescence. The abscissa and ordinate of this graph express the same items as those of FIG. 23. To determine the relationship between the illumination duration of the excitation light and the temporal variation of delayed luminescence, the above-described measurement was repeated with the illumination duration of the first excitation light being changed to 5, 10, and 30 seconds (the waiting time was set to 0 seconds). FIG. 25 shows that as the illumination duration of the first excitation light decreases, the decay curve approaches that of the non-saturation case (the case where the excitation light is not illuminated).

As shown in FIGS. 24 and 25, the change of the decay curve depends on the illumination light amount and the illumination duration of the first excitation light. That is, an increase or decrease of the luminescence amount at a specific measurement time period that occurs according to the length of the waiting time as shown in FIG. 23 is considered to directly or indirectly reflect the saturation and recovery of the photosynthetic electron transport system according to light illumination.

Figure 26:
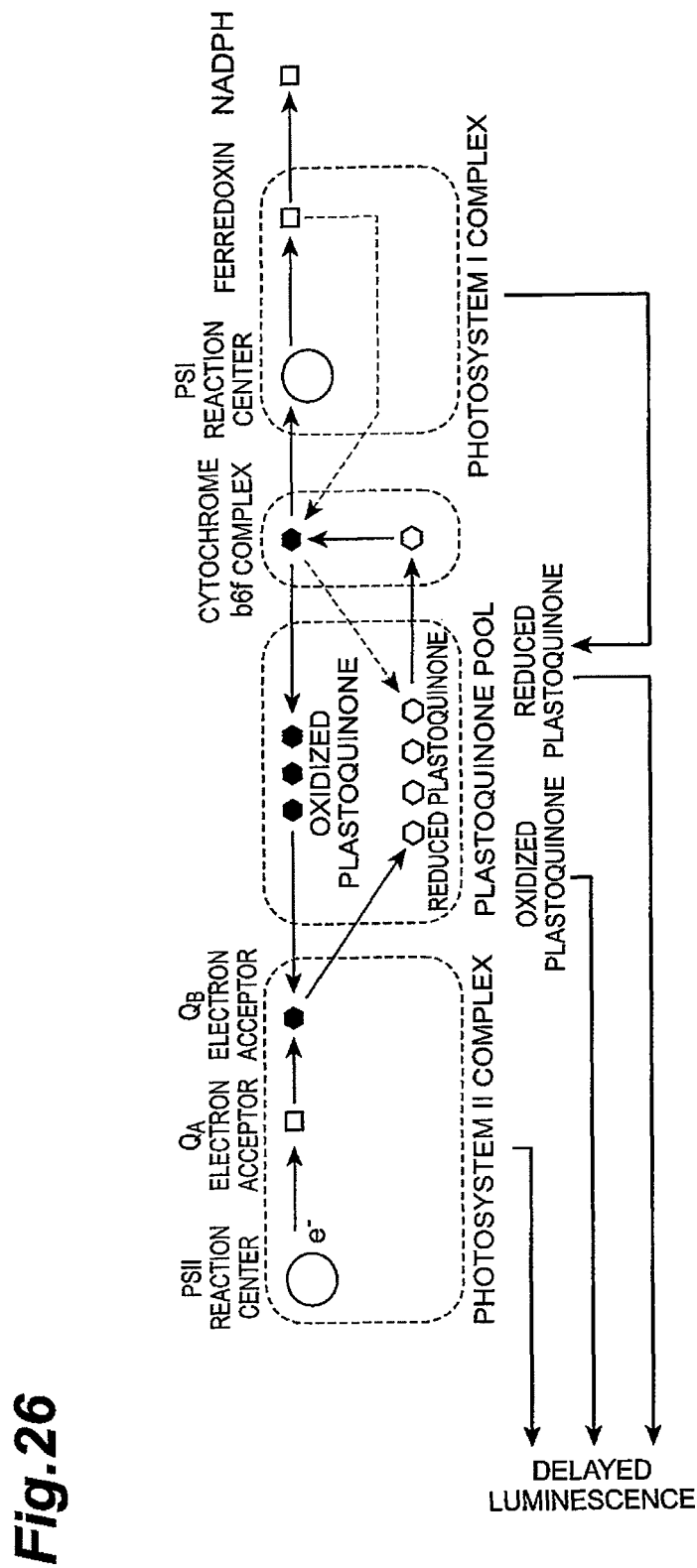
FIG. 26 is a schematic view of a relationship of redox states and emission of delayed luminescence in a non-saturation state.
Figure 27:
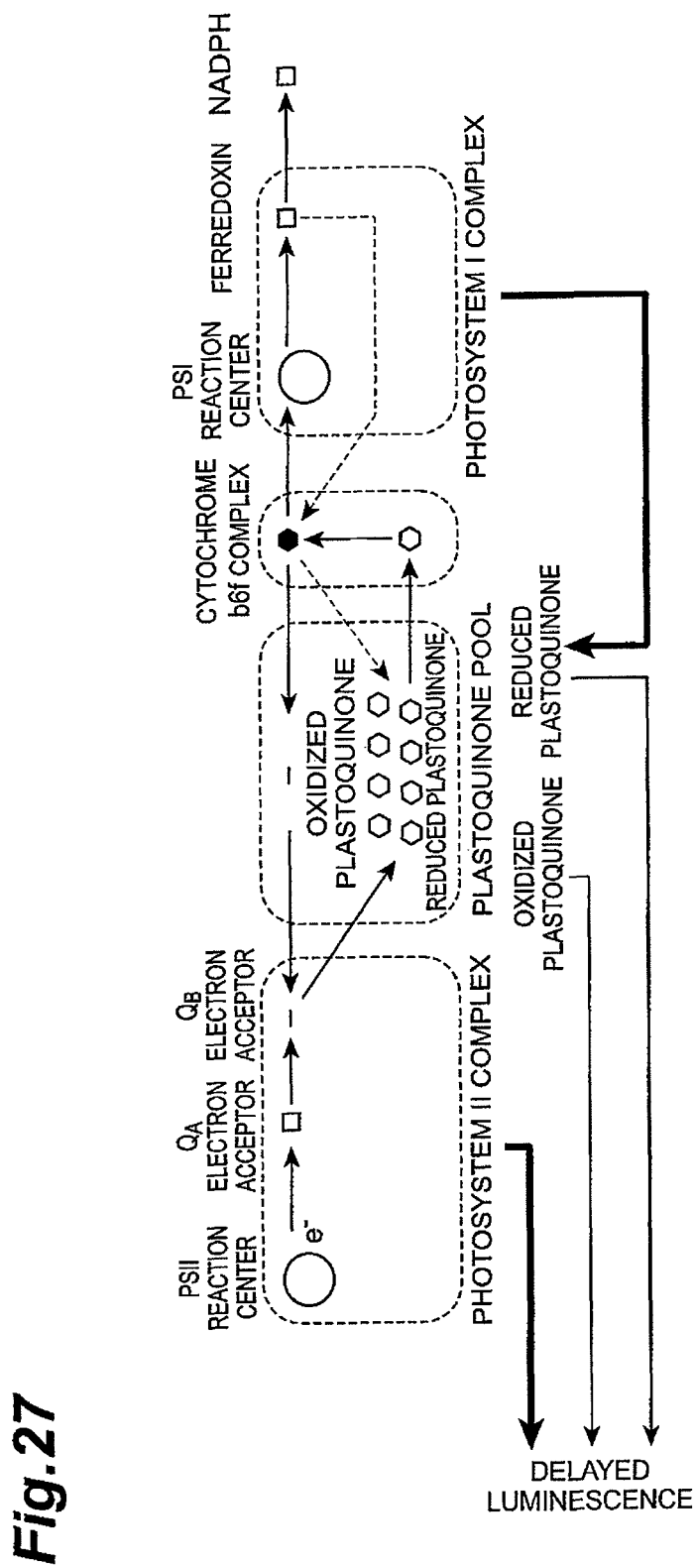
FIG. 27 is a schematic view of a relationship of the redox states and the emission of delayed luminescence in a case where a waiting time is not provided after illumination of a first excitation light.
Figure 28:
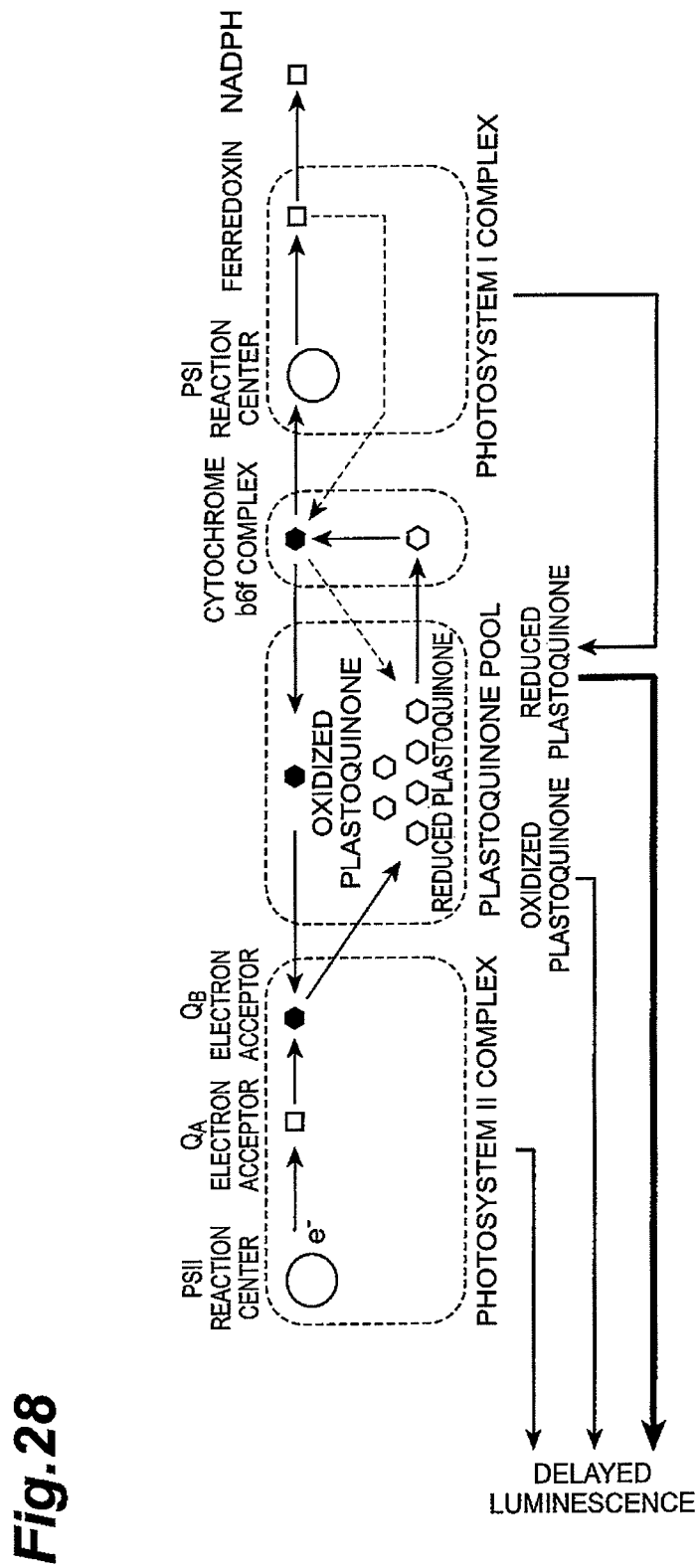
FIG. 28 is a schematic view of a relationship of the redox states and the emission of delayed luminescence in a case where a waiting time of 2 seconds is provided after illumination of the first excitation light.

This point shall now be described in detail by describing the redox states and the emission of delayed luminescence in parallel in consideration of actions of molecules involved in photosynthetic electron transport and using FIGS. 26 to 28. FIG. 26 is a schematic view of a relationship of the redox states and the emission of delayed luminescence in the non-saturated state. FIG. 27 is a schematic view of a relationship of the redox states and the emission of delayed luminescence in the case where a waiting time is not provided after illumination of the first excitation light (the 0-second waiting time case). FIG. 28 is a schematic view of a relationship of the redox states and the emission of delayed luminescence in the case where a waiting time of 2 seconds is provided after illumination of the first excitation light.

When there is no saturation, because excitation light of the same light intensity as that during culturing of the photosynthetic sample (green algae) is illuminated onto the measurement sample, it is considered that there is hardly any influence on the photosynthetic electron transport. In this case, as shown in FIG. 26, saturation does not occur in the process of an electron being transported from the PSII to the PSI via the pQ pool, and the oxidized plastoquinone and the reduced plastoquinone are present in the pQ pool in a well balanced manner. Because electrons of the three principal electron accumulating portions (PSII, pQ pool, and PSI), which influence the delayed luminescence, chemically re-excite the P680 in a final stage due to reverse reactions, delayed luminescence occurs. The delayed luminescence that is measured is a total of the delayed luminescence emitted from each of the three electron accumulating portions.

In the 0-second waiting time case, the delayed luminescence is measured upon illuminating the second excitation light immediately after illuminating the first excitation light. It can thus be said that the photosynthetic electron transport system is in the most saturated state. In this case, as shown in FIG. 27, in the pQ pool, whereas the amount of the reduced plastoquinone, produced as a result of illumination of strong light, is high, the amount of the oxidized plastoquinone is low. In such a circumstance, reoxidation of the reduced plastoquinone by the cytb6f becomes rate-limiting and the amount of the oxidized plastoquinone that can receive electrons from the PSII becomes inadequate. The takeout of electrons from the interior of the PSII thus drops and the accumulation of electrons inside the PSII increases. Consequently, the delayed luminescence that reflects the electron accumulation inside the PSII increases. Such increase of the delayed luminescence that reflects the electron accumulation inside the PSII appears as an increase of the luminescence amount from 0.1 seconds to around 0.5 seconds after excitation in the decay curve for 0-second waiting time case as shown in FIG. 23.

That the delayed luminescence at a point at which not much time has elapsed after excitation reflects the electrons of the PSII is described in: Kretsch, G. and Gerhardt, V., "Numerical analysis of delayed fluorescence kinetics of algae," Archiv fur Hydrobiologie—Beiheft Ergebrisse der Limnologie, 1987, 29 pp. 47-54 (referred to hereinafter as "Reference Document 1") and Schmidt, W. and Senger, H., "Long-term delayed luminescence in Scenesdesmus obliquus 1. Spectral and kinetic properties," Biochemica et Biophysica Acta, 1987, 890, pp. 15-22 (referred to hereinafter as "Reference Document 2").

As pathways of reverse flow of electrons from the pQ pool to the P680 of the PSII, the two pathways of a pathway via the oxidized plastoquinone bonded to the QB site of the PSII and a pathway reflecting an equilibrium state of the reduced plastoquinone that has become dissociated from the QB site and has moved to the pQ pool may be considered. Although these two predicted pathways are reactions that take place via the QB site inside the PSII, because the delayed luminescence reflects the redox state of the pQ pool, the delayed luminescence shall be handled as reflecting the electron accumulation in the pQ pool. Under circumstances where the photosynthetic electron transport is saturated and a large amount of the reduced plastoquinone is present, whereas the delayed luminescence that reflects the oxidized plastoquinone decreases, the delayed luminescence that reflects the reduced plastoquinone increases.

As indicated by the decay curve for the 0-second waiting time in FIG. 23, it is considered that the decrease of the delayed luminescence that reflects the decrease of the oxidized plastoquinone appears as the decrease of the luminescence amount from around 0.5 seconds to around 10 seconds after excitation. Also, the increase of the luminescence amount that accompanies the increase of the reduced plastoquinone is considered to appear as the increase of the luminescence amount from around 10 seconds to around 50 seconds after excitation. It is considered that the decrease of the luminescence amount that reflects the reduced plastoquinone appears earlier in time than the increase of the luminescence amount that reflects the reduced plastoquinone because the reaction of the oxidized plastoquinone, bonded to the QB site inside the PSII, proceeds in a shorter time than that of the reduced plastoquinone that moves inside the PSII and the thylakoid membrane and forms the equilibrium state. That the delayed luminescence that reflects the pQ pool is emitted later than the delayed luminescence that reflects the PSII is described in Reference Document 1.

Furthermore, as pathways of the reverse flow of electrons, accumulated in the PSI onward, the two pathways of a pathway from the P700 to the cytb6f reflecting a reverse reaction of an equilibrium state that is intermediated by an oxidation reaction of the reduced plastoquinone, and a pathway by cyclic electron transport, with which an electron is transported to the oxidized plastoquinone inside the cytb6f via the ferredoxin (Fd) of the PSI to give rise to reduced plastoquinone, may be considered. In this case, in either pathway, an electron of the PSI flows in reverse to the P680 via the reduced plastoquinone. As indicated by the decay curve for the 0-second waiting time in FIG. 23, the increase of the delayed luminescence from the PSI via the reduced plastoquinone is considered to appear as the increase of the luminescence amount from around 10 seconds to 50 seconds after excitation. That the delayed luminescence reflecting the PSI is emitted in a range of several dozen seconds after excitation is described in Reference Document 1 and Reference Document 2.

That is, the increase of the luminescence amount from around 10 seconds to 50 seconds after excitation reflects the reduced plastoquinone resulting from both the reduction of the pQ pool in accordance with light illumination and the reduction of the pQ pool that reflects the equilibrium state of the P700 and the cyclic electron transport from the PSI. In the present specification, the delayed luminescence measured in an interval from 10 seconds to 50 seconds after excitation shall mainly be handled as reflecting the equilibrium state of the P700 and the cyclic electron transport from the PSI.

In the case of the 2-second waiting time, the delayed luminescence is measured upon illuminating the second excitation light upon providing the waiting time of 2 seconds after illuminating the first excitation light. The measurement result can thus be said to be that of a point at which the photosynthetic electron transport system has recovered somewhat from saturation in comparison to the 0-second waiting time case. In this case, because, as shown in FIG. 28, the oxidized plastoquinone is formed during the waiting time, electrons can be taken out from the PSII and the increase of the luminescence amount from 0.1 seconds to around 0.5 seconds after excitation, which was observed with the 0-second waiting time, cannot be seen. Because movement of the oxidized plastoquinone to the QB site is also enabled, the degree of decrease of the luminescence amount from around 0.5 seconds to around 10 seconds after excitation is somewhat lessened.

From this, the degree of increase of the delayed luminescence from around 10 seconds to 50 seconds after excitation that reflects the reduced plastoquinone should also lessen in likewise manner. However, when the 2-second waiting time is provided, the delayed luminescence from around 10 seconds to 50 seconds after excitation is increased in comparison to that of the 0-second waiting time. This is considered to be due to the reverse flow of electrons at the PSI onward. It can thus be said that the delayed luminescence from around 10 seconds to 50 seconds after excitation that is increased by making the waiting time long mainly reflects the electrons at the PSI onward.

Thus based on the decay curves of delayed luminescence obtained from the respective measurement samples that mutually differ in redox state as shown in FIG. 23, the electron accumulation in the PSII, the pQ pool, and the PSI in accordance with the saturation and recovery of the photosynthetic electron transport system can be evaluated. For example, by noting the variation of the luminescence amount in the respective time periods of 0.1 to 0.5 seconds after excitation, 0.6 to 10 seconds after excitation, and 0.1 to 50 seconds after excitation as the time periods at which increase/decrease of the luminescence amount appears characteristically among the time after excitation, the electron accumulation can be evaluated clearly.

By thus deriving the evaluation values based on the respective luminescence amounts of delayed luminescence obtained by changing the illumination starting timing of the second excitation light for the evaluation sample, the redox state of the photosynthetic sample contained in the evaluation sample can be evaluated appropriately. Also, the luminescence amount of delayed luminescence is measured upon illuminating the second excitation light so that its energy integration value is less than that of the first excitation light. The change of the redox state by the illumination of the first excitation light is thus not impeded by the illumination of the second excitation light and yet the decay of the delayed luminescence can be prevented. The luminescence amount of delayed luminescence can thus be measured more precisely.

Evaluation of the Sample by Integration Values

Evaluation of the electron accumulation in the PSII, the pQ pool, and the PSI is thus useful for evaluating a sample containing a photosynthetic sample. Specifically, this is useful for evaluating an environmental factor present in an evaluation sample containing a photosynthetic sample. More specifically, this is useful for evaluation of efficiency of photosynthetic electron transport in a photosynthetic sample, evaluation of a chemical substance that inhibits a photosynthetic reaction, diagnosis of plant growth, research on an influence of a harmful substance on a plant, functional analysis of an agricultural chemical, and research on photosynthesis. A method for evaluating a sample based on an integration value of a measured luminescence amount of delayed luminescence (delayed luminescence intensity) shall now be described.

In the following, a case of computing an integration value for each of an integration range (measurement time period) of 0.1 to 0.5 seconds of time after excitation, an integration range of 0.6 to 10 seconds after excitation, and an integration range of 10.1 seconds to 50 seconds after excitation shall be described. Setting of the integration ranges is not restricted to the above. The number of integration ranges may any number as long as it is no less than 1. In a case where a plurality of integration ranges are set up, the respective integration ranges may be made equal or not equal in time width. Furthermore, the integration ranges may not only be mutually set apart by a predetermined time as in the present embodiment but integration ranges may be set so as to be adjacent each other (for example, an integration range of 0.1 to 0.5 seconds of time after excitation and an integration range of 0.5 seconds to 10 seconds of time after excitation may be set up) and integration ranges may be set so as to overlap with each other (for example, an integration range of 0.1 to 0.5 seconds of time after excitation and an integration range of 0.4 seconds to 10 seconds of time after excitation may be set up).

Figure 29:
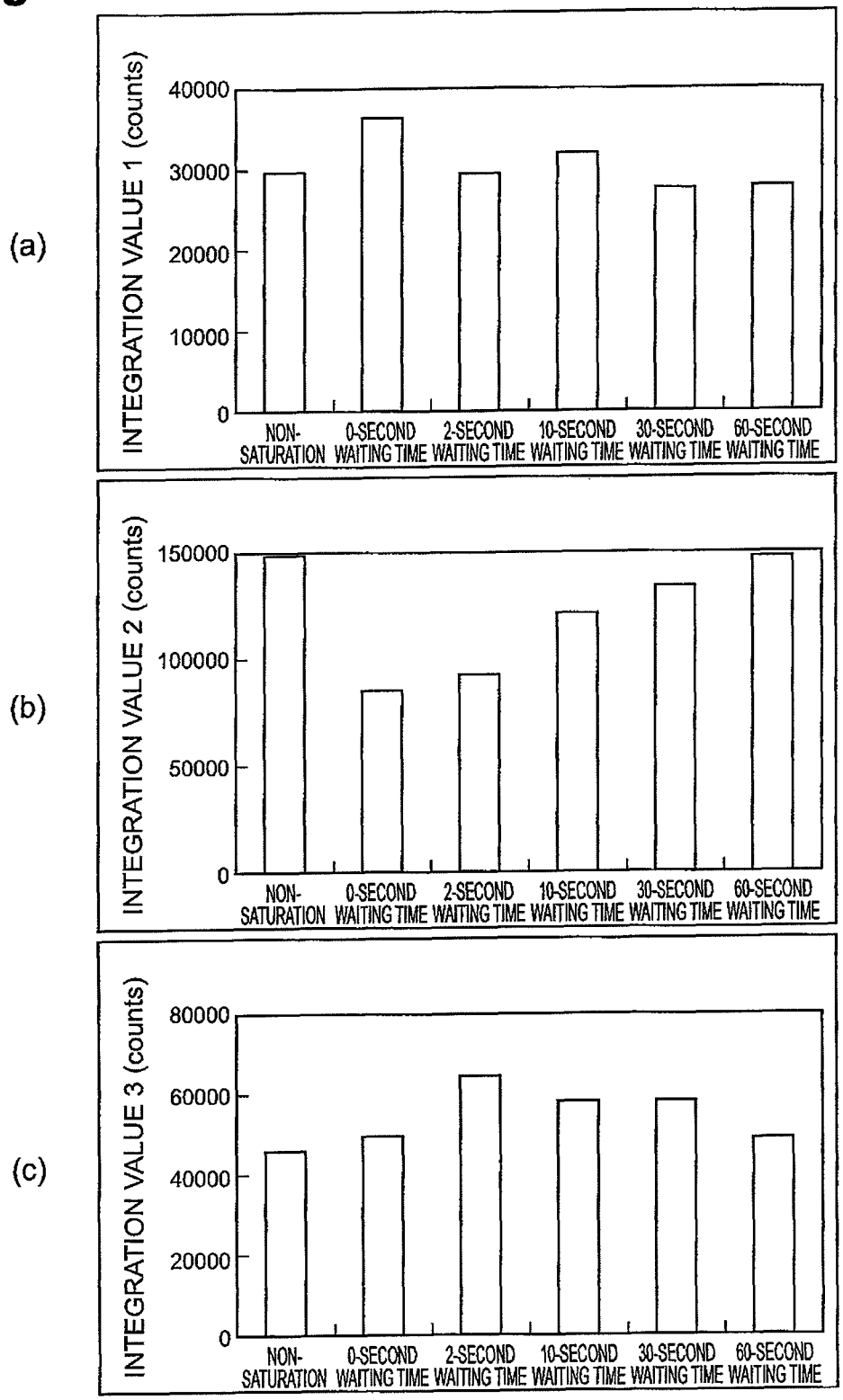
FIG. 29 shows graphs of integration values concerning the decay curves shown in FIG. 23, with FIG. 29A being a graph of an integration value 1, FIG. 29B being a graph of an integration value 2, and FIG. 29C being a graph of an integration value 3.

FIG. 29 shows graphs of results of computing integration values according to the three integration ranges for the delayed luminescence intensity decay curves shown in FIG. 23. In each graph of FIG. 29, the abscissa expresses the measurement condition and the ordinate expresses the integration value (counts) of the delayed luminescence intensity. In the following, the integration value in the integration range of 0.1 to 0.5 seconds of time after excitation, the integration value in the integration range of 0.6 to 10 seconds after excitation, and the integration value in the integration range of 10.1 seconds to 50 seconds after excitation shall be referred to respectively as integration value 1, integration value 2, and integration value 3. FIGS. 29A, 29B, and 29C are graphs respectively of the integration value 1, integration value 2, and integration value 3.

First, an examination based on the integration value 1 shall be made. As shown in FIG. 29A, the integration value 1 for the case of the 0-second waiting time is high compared to that of the non-saturation case. Meanwhile, the integration value 1 for the case of the 2-second waiting time does not differ much from that of the non-saturation case. The change in the case of the 0-second waiting time is due to the electron accumulation inside the PSII increasing due to the reduced plastoquinone being formed excessively by the illumination of the first excitation light and the oxidized plastoquinone that can bind to the QB site in the PSII and receive electrons from inside the PSII thereby falling into shortage. Meanwhile, the results for the cases where the waiting time is set to 2 seconds or more are due to the oxidized plastoquinone being formed during the waiting time and the electrons inside the PSII being taken out. The integration value 1 thus reflects the electron accumulation inside the PSII. When the integration value 1 is high, this indicates the interior of the PSII is in a reduced state in which a large amount of electrons is accumulated.

This shall now be examined from a standpoint of change due to difference in the redox state of the photosynthetic sample. In a normal state of the photosynthetic electron transport, immediately after illumination of an excitation light that saturates electron transport (for example, illumination of the first excitation light), the pQ pool is put in a reduced state and the oxidized plastoquinone that can bind to the QB site is in shortage. Although the integration value 1 thus increases transiently, this is annulled by a condition (for example, waiting for a predetermined duration) by which recovery from the saturated state is achieved. It can thus be said that an increment of the integration value 1 for the 0-second waiting time (the state closest to saturation) in comparison to the integration value 1 for non-saturation expresses the electrons accumulated in the PSII due to saturation of electron transport. That is, the process of decrease of this increment under a condition (for example, waiting for a predetermined duration) by which recovery from the saturated state is achieved reflects the taking out of electrons from the PSII by the oxidized plastoquinone. Thus by noting differences among the integration values 1 of mutually different redox states of the photosynthetic sample, actions of an environmental factor (for example, a harmful substance) on the electron accumulation in and takeout of electrons from the interior of the PSII can be evaluated.

Next, an examination based on the integration value 2 shall be made. As shown in FIG. 29B, in comparison to the non-saturation case, the integration value 2 is decreased the most when the waiting time is 0 seconds. The difference lessens as the waiting time becomes long, and for the waiting time of 60 seconds, the integration value 2 recovers to be substantially equivalent to that of the non-saturation case. The integration value 2 thus reflects the oxidized plastoquinone that can bind to the QB site inside the PSII and receive electrons. In the case of the 0-second waiting time, the reduced plastoquinone is formed excessively by the illumination of the first excitation light and the oxidized plastoquinone that can bind to the QB site inside the PSII and receive electrons from inside the PSII is in shortage. The delayed luminescence that reflects the electron accumulation in the plastoquinone bound to the QB site thus decreases. However, as the waiting time becomes long, the formation of the oxidized plastoquinone proceeds, and the amount of the delayed luminescence that occurs via the QB site recovers.

The difference of the integration value 2 for the 0-second waiting time (the state closest to saturation) with respect to the integration value 2 for the non-saturation case thus expresses the reduction of the pQ pool by the strong light illumination. The process of decrease of the difference under a condition (for example, waiting for a predetermined time) by which recovery from saturation is achieved expresses the process of reoxidation of the reduced plastoquinone by the cytb6f, etc. Thus by noting the differences among the integration values 2 of mutually different redox states, actions of an environmental factor on the reduced state of the pQ pool and the reoxidation process can be evaluated.

Next, an examination based on the integration value 3 shall be made. As shown in FIG. 29C, in comparison to the non-saturation case, the integration value 3 is increased the most when the waiting time is 2 seconds and decreases to be substantially equal to that of the non-saturation case at the waiting time of 60 seconds. The integration value 3 for the case where a waiting time of 2 seconds or more is provided can be said to correspond mainly to the reduced plastoquinone that reflects the electron accumulation at the PSI onward. That is, increments of the integration values 3 under the respective conditions of waiting time of 0 to 60 seconds with respect to the integration value 3 for the non-saturation case express the flow of electrons arriving to the PSII from the PSI onward by the reverse reactions via the cyclic electron transport and the P700. Thus by noting the differences among the integration values 3 of mutually different redox states, actions of an environmental factor on the electron accumulation at the PSI onward and the cyclic electron transport can be evaluated.

By use of such integration values, it becomes possible to more appropriately extract a redox state of a photosynthetic sample that appears in a temporal variation of a luminescence amount of delayed luminescence. Consequently, a redox state of a photosynthetic sample contained in an evaluation sample can be evaluated appropriately. In a case where a plurality of integration values are computed as described above, because a temporal variation of a luminescence amount of delayed luminescence can be grasped, a redox state can be evaluated appropriately by making use of the temporal variation.

From the above, it can be understood that as a method for evaluating saturation and recovery therefrom of a photosynthetic electron transport system, it is effective to prepare a plurality of states that mutually differ in redox state, measure the delayed luminescence for each of these states, and use indices (for example, the integration values 1, 2, and 3) that express the delayed luminescence that reflects the electron accumulation inside the PSII, in the plastoquinone pool, and at the PSI onward.

Evaluation of an Environmental Factor

A method for evaluating an impact of an environmental factor on a photosynthetic sample by evaluating the saturation and recovery therefrom of the photosynthetic electron transport system shall now be described. As the evaluation method, the evaluation method using the integration values 1, 2, and 3 is used.

Here, a standard sample (Cont) and an evaluation sample are prepared. As the photosynthetic sample contained in each sample, the same green algae as that mentioned above is used. Specifically, 2.5 mL of a cell suspension, prepared by adjusting to a 685 nm absorbance OD685 of 0.05 using the C (75) medium as a diluent and thereafter culturing for 1 hour under an environment of 25° C.±1° C. air temperature while illuminating white light of 50 μmol·m−2·s−1, is used as the standard sample. Meanwhile, the evaluation sample is prepared by performing preparation according to the same procedure as the standard sample and then applying ultraviolet rays of 365 nm at an intensity of 100 μW/cm2 (UV illumination) as an environmental factor in the process of culturing for 1 hour under an environment of 25° C.±1° C. air temperature while illuminating white light of 50 μmol·m−2·s−1. Measurement of the luminescence amount of delayed luminescence is performed after setting still the standard sample and the evaluation sample for 60 seconds in darkness in advance to eliminate influences of the environment on the photosynthetic electron transport system prior to measurement and unifying the photosynthetic electron transport system to a fixed redox state.

Figure 30:
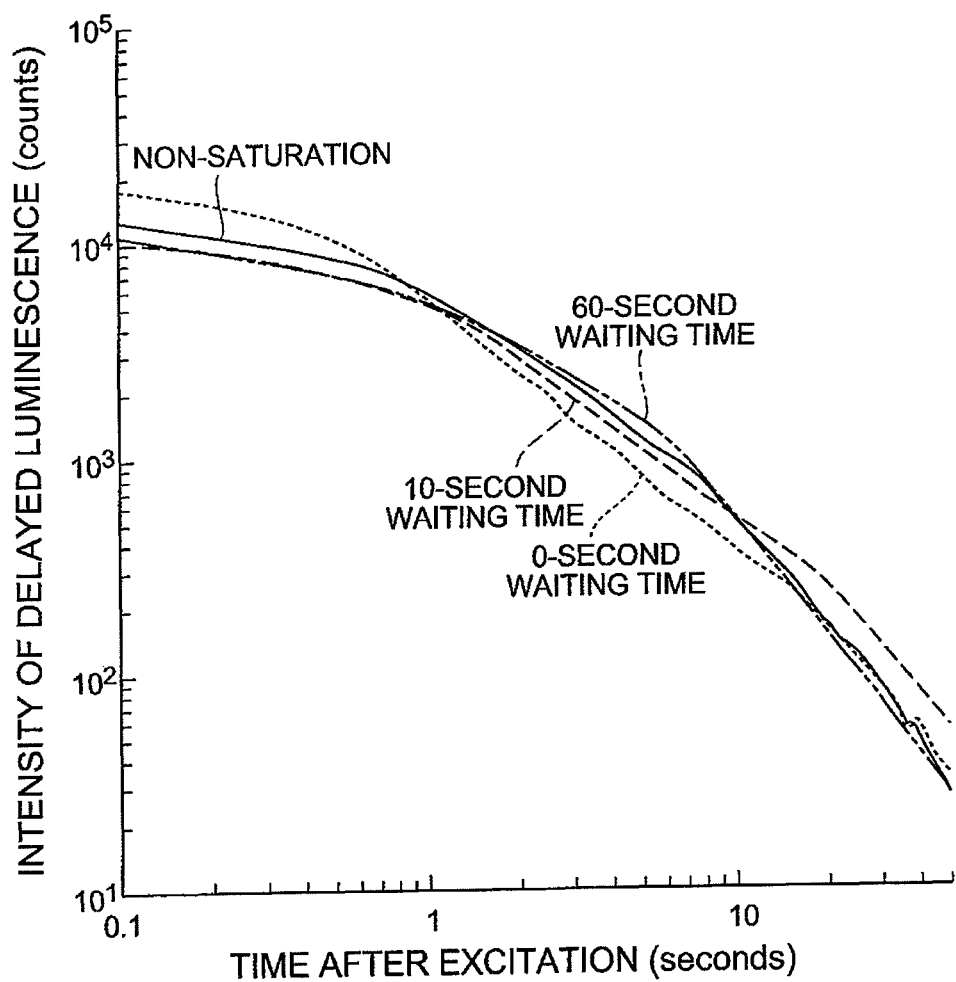
FIG. 30 is a graph of a relationship between the waiting time and the temporal variation of the luminescence amount of delayed luminescence in a standard sample.
Figure 31:
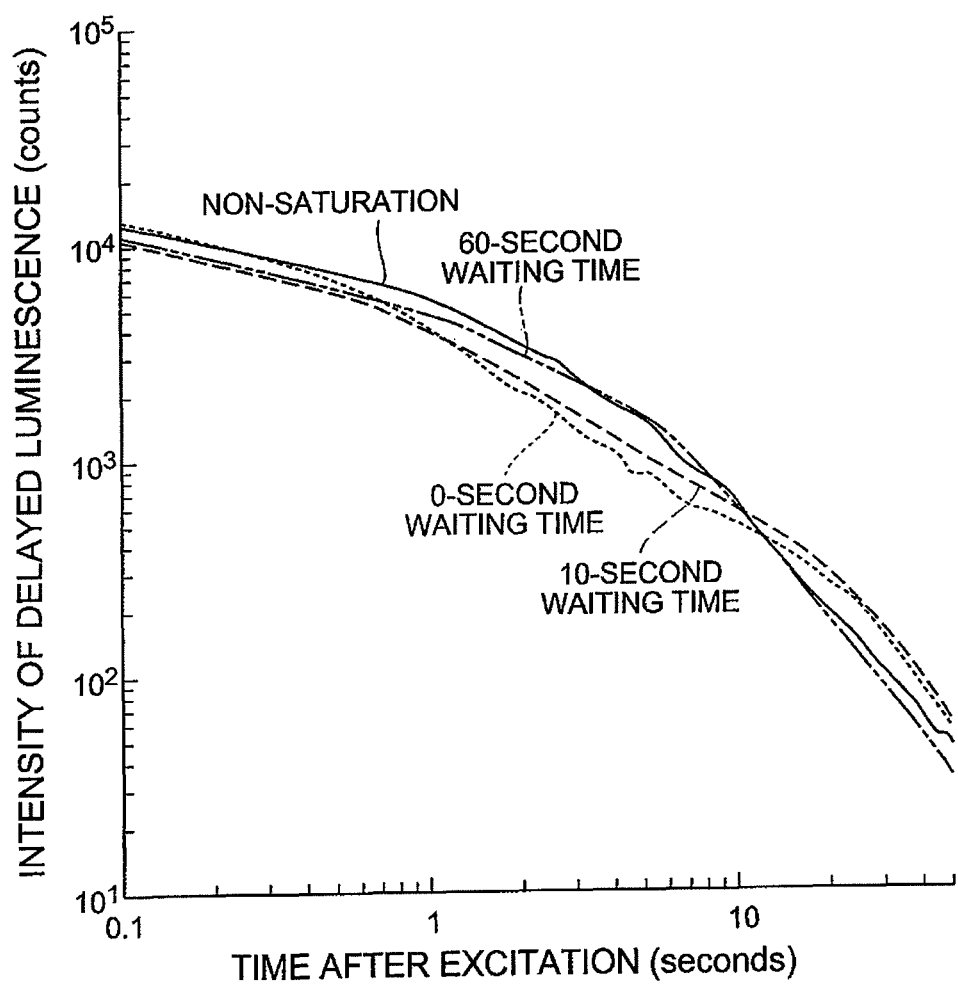
FIG. 31 is a graph of a relationship between the waiting time and the temporal variation of delayed luminescence in an evaluation sample.

FIG. 30 is a graph of a relationship between the waiting time and the temporal variation of the luminescence amount of delayed luminescence in the standard sample. FIG. 31 is a graph of a relationship between the waiting time and the temporal variation of delayed luminescence in the evaluation sample. In each graph, the temporal variations of the luminescence amount of delayed luminescence for the respective cases of non-saturation, a waiting time of 0 seconds, a waiting time of 10 seconds, and a waiting time of 60 seconds are shown. From a comparison of FIGS. 30 and 31, it can be understood that shapes of the decay curves are changed characteristically by the UV illumination.

Influences of the UV illumination shall now be described in detail. FIG. 32 shows graphs of the integration values 1, 2, and 3 computed for the respective samples based on the luminescence amounts of delayed luminescence shown in FIGS. 30 and 31, and FIGS. 32A, 32B, and 32C are graphs of the integration value 1, the integration value 2, and the integration value 3, respectively.

First, in regard to the standard sample, the integration value 1 that reflects the electrons inside the PSII exhibits a maximum value in the case of the 0-second waiting time and values that are substantially equal to the value of the non-saturation case are exhibited in the cases of the 10-second and 60-second waiting times. As mentioned above, this is because, immediately after illumination of the first excitation light (in the case of the 0-second waiting time), the electron accumulation inside the PSII increases due to there being a large amount of the reduced plastoquinone present in the pQ pool and the oxidized plastoquinone that can take out electrons from the PSII being few. On the other hand, in the cases of the 10-second and 60-second waiting times, because the oxidized plastoquinone is formed during the waiting time, the photosynthetic electron transport system recovers to a state nearly equivalent to that of the non-saturation case where the electron transport reaction of the PSII proceeds smoothly.

Meanwhile, the integration value 2 that reflects the electrons of the pQ pool exhibits a minimum value at the 0-second waiting time and gradually increases and approaches the non-saturation value as the waiting time becomes longer. As mentioned above, this is because, immediately after illumination of the first excitation light (in the case of the 0-second waiting time), a large amount of reduced plastoquinone is present in the pQ pool and the oxidized plastoquinone that can bind to the QB site, which is the plastoquinone binding site inside the PSII, is in shortage. Meanwhile, when just a predetermined amount of time is provided as the waiting time, because the oxidized plastoquinone is generated during the waiting time, the photosynthetic electron transport system recovers to a state nearly equivalent to that of the non-saturation case.

Furthermore, the integration value 3 that reflects the electrons at the PSI onward takes on substantially the same value in the non-saturation, 0-second waiting time, and 60-second waiting time cases and increases in value only in the 10-second waiting time case. This reflects the delayed luminescence due to the cyclic electron transport reaction, with which the electrons accumulated in the ferredoxin and NADPH at the PSI onward are transported via the ferredoxin to the oxidized plastoquinone to form the reduced plastoquinone, and the reverse reaction via the P700, etc. Because the delayed luminescence reflected by the integration value 3 transits through a larger number of reaction pathways in comparison to the delayed luminescence reflected by the integration value 1 or the integration value 2, a higher value is exhibited in the 10-second waiting time case than in the 0-second waiting time case. The integration value 3 recovers to a value equivalent to the non-saturation case in the 60-second waiting time case.

Next, in regard to the evaluation sample on which UV illumination was performed, the integration value 1 that reflects the electrons inside the PSII does not increase in the 0-second waiting time case and does not exhibit a large change in the 10-second and 60-second waiting time cases. This indicates that some change has occurred in the PSII due to the ultraviolet illumination.

Meanwhile, the integration value 2 that reflects the electrons in the pQ pool exhibits a minimum value at the 0-second waiting time, though somewhat decreased from that of the standard sample, and does not change in the trend of gradually approaching the non-saturation value as the waiting time becomes longer. This indicates that the ultraviolet illumination does not have much influence on the actions of the pQ pool.

Furthermore, with the integration value 3 that reflects the electrons at the PSI onward, although nearly the same value is exhibited in the non-saturation case and the 60-second waiting time case, the value is increased in the 0-second waiting time case in addition to the 10-second waiting time case. This indicates that due to the ultraviolet illumination, the cyclic electron transport reaction, with which the electrons are transported via the PSI to the oxidized plastoquinone to form the reduced plastoquinone, and the reverse reaction via the P700 have increased.

Evaluation Value Computation Method

A method for computing (deriving) the evaluation value in the evaluating step shall now be described. This description is premised on the abovementioned waiting times (0-second waiting time, 10-second waiting time, and 60-second waiting time) being the second illumination conditions and the evaluation value being based on the integration values 1, 2, and 3. It is also premised that the integration values 1, 2, and 3 are likewise computed in the non-saturation case.

First, a method for computing an evaluation value for evaluating the electron accumulation state of the PSII of the photosynthetic sample shall be described. As one such type of evaluation value, there is, for example, a PSII electron accumulation change (eI), which indicates how the electron accumulation in the PSII has changed. This value eII can be determined as: (integration value 1 of the evaluation sample)/ (integration value 1 of the standard sample)×100. The PSII electron accumulation change (eII) can be computed for the respective conditions of non-saturation, 0-second waiting time, 10-second waiting time, and 60-second waiting time.

That the PSII electron accumulation change (eII) exceeds 100 indicates that the electron accumulation in the PSII has increased. For example, by computing the eII for the non-saturation condition, the change of the electron accumulation in the PSII under a standard condition without any influence of strong light (for example, the non-saturation case) can be evaluated.

As mentioned above, the transient increase of the integration value 1 in the 0-second waiting time reflects increase of the electron accumulation in the PSII due to the takeout of electrons from the PSII becoming rate-limiting. Recovery from this transient increase of the integration value 1 to a level equivalent to the non-saturation case can be achieved by providing a waiting time in which light is not illuminated. For example, the capacity to take out electrons from the PSII at a certain waiting time enables evaluation of how much the transient increase of the integration value 1 of the 0-second waiting time is decreased by the provision of the waiting time. A PSII electron takeout capacity (tII) from the 0-second waiting time to a certain condition is thus computed as an evaluation value. This evaluation value tiI can be determined as: ((integration value 1 for the 0-second waiting time case)/

(integration value 1 for the non-saturation case)−(integration value 1 for a certain waiting time)/(integration value 1 for the non-saturation case))×100.

When the PSII electron takeout capacity (tII) from the 0-second waiting time to a certain waiting time is large, this indicates that much of the transient electron accumulation in the PSII has been resolved between the 0-second waiting time and the certain waiting time. Oppositely, if the value tII is a negative value, this indicates that the electron accumulation in the PSII has increased due to some cause between the 0-second waiting time and the certain waiting time.

Furthermore, by comparing the PSII electron takeout capacity (tII) from the 0-second waiting time to the certain waiting time of the standard sample, to which the environmental factor has not been applied, and that of the evaluation sample, to which the environmental factor has been applied, how the takeout of electrons from the PSII has changed can be made known. As a value that indicates this change, a PSII electron takeout change (vII) from the 0-second waiting time to a certain condition is computed as an evaluation value. The value vII can be determined as: (tII of the evaluation sample)/(tII of the standard sample)×100. If this value vII is 100, this indicates that the capacity to take out electrons from the PSII is not changed by the environmental factor. On the other hand, if the value vII is small, this indicates that the capacity to take out electrons from the PSII is lowered, and when the value is negative, this indicates that electrons are flowing into the PSII.

Also with the evaluation method for photosynthetic sample according to the present embodiment, the redox state of the pQ pool of the photosynthetic sample can be evaluated. For example, an evaluation value can be derived using the integration value 2 that reflects the redox state of the pQ pool.

With the present embodiment, because the photosynthetic sample is left to stand still in darkness for 60 seconds in advance, in the non-saturation case, the reduced plastoquinone, formed by light illumination, is reoxidized and a state where the pQ pool is substantially oxidized is attained. At the 0-second waiting time, which is immediately after illumination of the first excitation light, the pQ pool is in a state of being nearly entirely reduced and hardly any oxidized plastoquinone is present. Thus a difference between the integration value 2 of the non-saturation case and the integration value 2 of the 0-second waiting time case expresses a magnitude of the redox reaction by light illumination. Thus as a value that indicates this magnitude, a redox reaction magnitude (sQ) is computed as an evaluation value. The value sQ can be determined as: (integration value 2 of the non-saturation case)−(integration value 2 of the 0-second waiting time case).

By computing the value sQ for both the standard sample and the evaluation sample and comparing these, it can be made known how the redox reaction magnitude of the photosynthetic sample has changed due to the environmental factor. A ratio of the redox reaction magnitude (sQ) of the evaluation sample with respect to the redox reaction magnitude (sQ) of the standard sample is thus determined as an evaluation value referred to as a change (vQ) of sQ due to the environmental factor. The value vQ can be determined as: (sQ of the evaluation sample)/(sQ of the standard sample).

As mentioned above, the pQ pool that is in the substantially reduced state at the waiting time of 0 seconds recovers to the unsaturated state by the provision of a waiting time because the reoxidation reaction by the cytb6f then proceeds and the oxidized plastoquinone is formed. That is, in regard to the integration value 2 that reflects the redox state of the pQ pool, by comparing the integration value 2 at a certain waiting time with the integration value 2 at the 0-second waiting time, the amount of oxidized plastoquinone formed at the certain waiting can be made known. This oxidized plastoquinone formation amount decreases when the reoxidation reaction by the cytb6f is inhibited and increases when the cyclic electron transport that reduces the oxidized plastoquinone at the cytb6f is inhibited. Thus an oxidized plastoquinone formation amount (oQ) at a certain waiting time is computed as an evaluation value. The value oQ can be determined as: (integration value 2 at a certain waiting time)−(integration value 2 at the 0-second waiting time).

Furthermore, a percentage (% oQ) of the oxidized plastoquinone at a certain waiting time with respect to the magnitude of the redox reaction of the pQ pool can be determined as: (oQ at a certain waiting time)/sQ×100.

Also with the evaluation method for photosynthetic sample according to the present embodiment, the state of electron accumulation of the PSI of the photosynthetic sample can be evaluated. For example, an evaluation value can be derived using the integration value 3 that is computed from the measurement result of delayed luminescence and reflects the state of electron accumulation in the PSI.

Specifically, by comparing the integration value 3 of the standard sample and the integration value 3 of the evaluation sample at a certain waiting time, how the electron accumulation in the PSI has changed can be made known. A PSI electron accumulation change (eI) is thus computed as an evaluation value. The PSI electron accumulation change (eI) can be determined as: (integration value 3 of the evaluation sample)/(integration value 3 of the standard sample)×100. The PSI electron accumulation change (eI) can be computed for the respective conditions of non-saturation, 0-second waiting time, 10-second waiting time, and 60-second waiting time. That the PSI electron accumulation change (eI) exceeds 100 indicates that the electron accumulation of the PSI has increased. For example, by computing the PSI electron accumulation change (eI) for the non-saturation condition, the change of the electron accumulation of the PSI under a standard condition without any influence of strong light can be evaluated.

When the above-described first excitation light is illuminated, the electron accumulation in the PSI increases. A portion of the electrons of the PSI reduces the pQ pool via the cyclic electron transport pathway and gives rise to the reduced plastoquinone. Much of the electrons transported to the reduced plastoquinone give rise to delayed luminescence at the PSII reaction center (P680) via the pQ pool, the QB site, and the QA site. With respect to the integration value 3 of the non-saturation case, the integration value 3 of the 10-second waiting time case increases transiently. Thus a difference, obtained by subtracting the integration value 3 of the non-saturation case from the integration value 3 of a case where a certain waiting time is provided, expresses the cyclic electron transport from the PSI at that waiting time. The cyclic electron transport (cI) from the PSI is thus computed as an evaluation value. The value cI can be determined as: (integration value 3 at a certain waiting time)/(integration value 3 for the non-saturation case).

As described above, by the present embodiment, changes of the redox state can be evaluated. For example, by applying an environmental factor (for example, ultraviolet rays or a chemical substance, etc.,) to the evaluation sample as described above, evaluation of whether the environmental factor is harmful for the photosynthetic sample or evaluation of actions of the environmental factor is enabled. Furthermore, when river water or soil-extracted water is used in preparing the evaluation sample, an environmental factor (a harmful or beneficial chemical substance) contained in the water can be evaluated.

Usefulness of the evaluation of changes of the redox state indicated in the present embodiment is not restricted to that mentioned above. For example, applications to plant growth diagnosis, evaluation of impact of a chemical substance on a plant, functional analysis and development of an agricultural chemical, photosynthesis research, etc., are also considered possible.

Evaluation Program for Photosynthetic Sample

Figure 33:
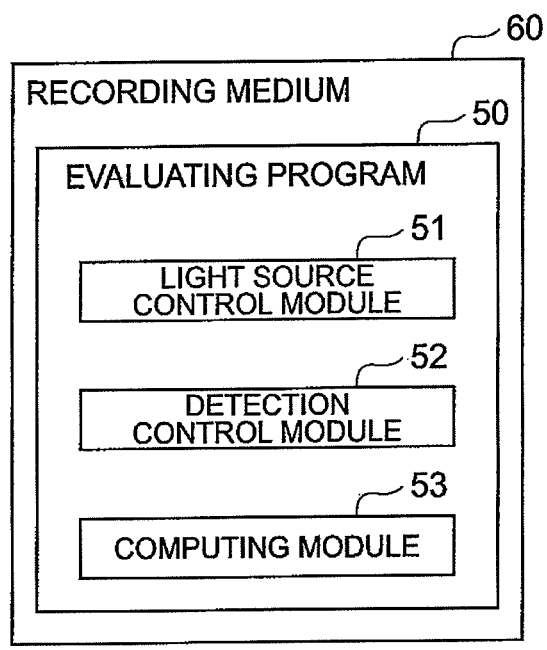
FIG. 33 is a diagram showing a configuration of an evaluation program according to the embodiment along with a storage medium.
Figure 34:
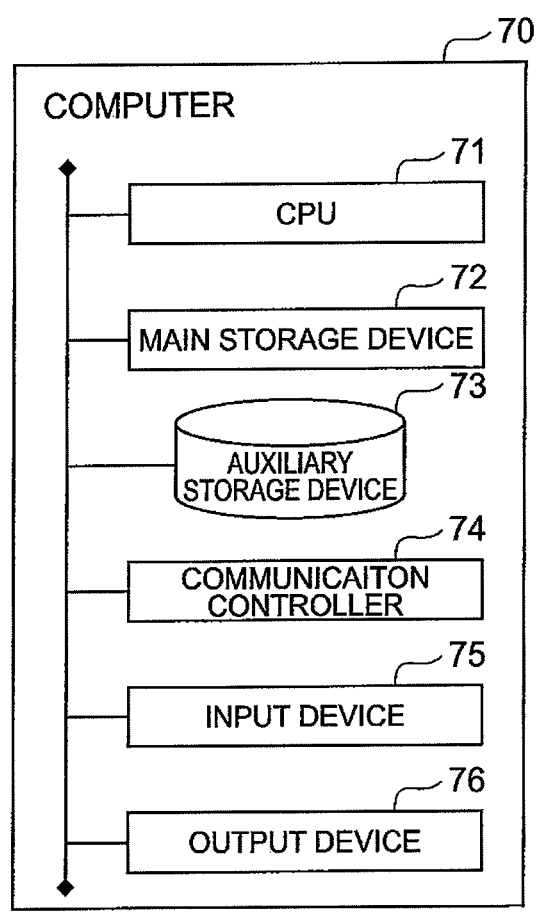
FIG. 34 is a diagram of a hardware configuration of a computer on which the evaluation program shown in FIG. 33 operates.
Figure 35:
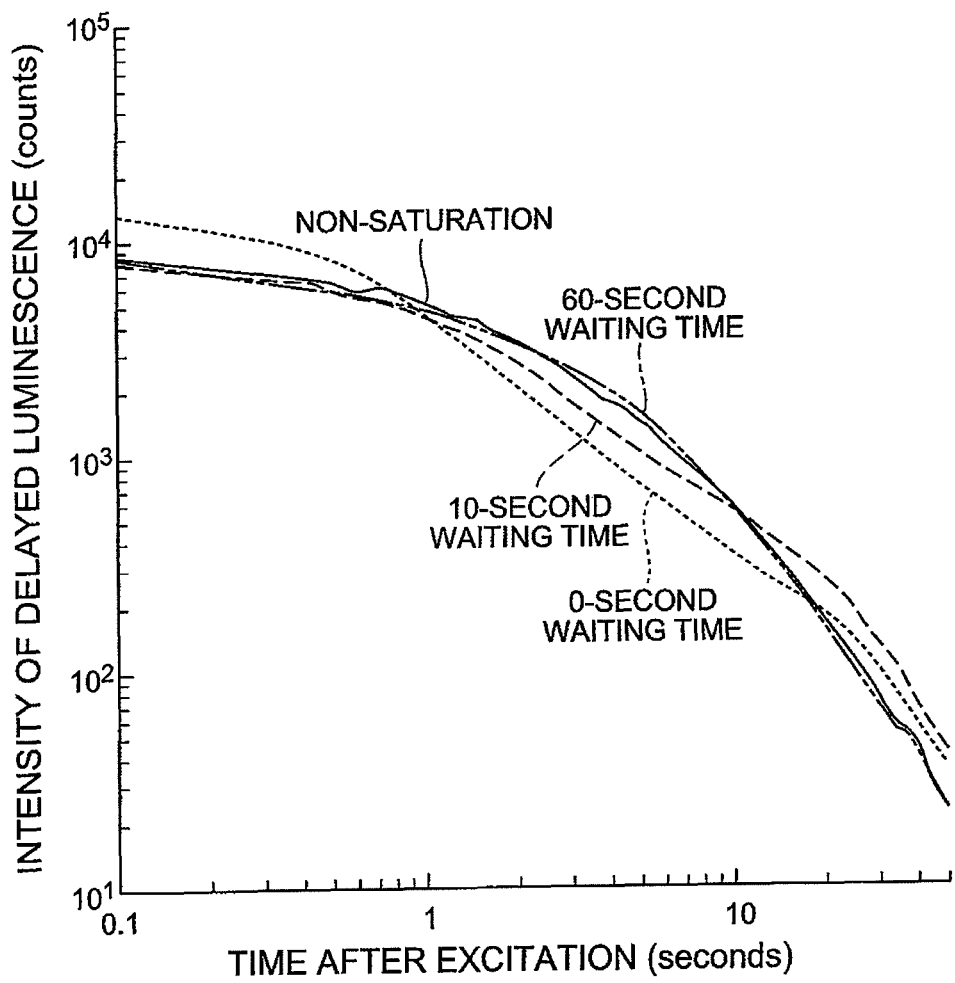
FIG. 35 is a graph of temporal variations of the luminescence amount of delayed luminescence of a standard sample in an example.
Figure 36:
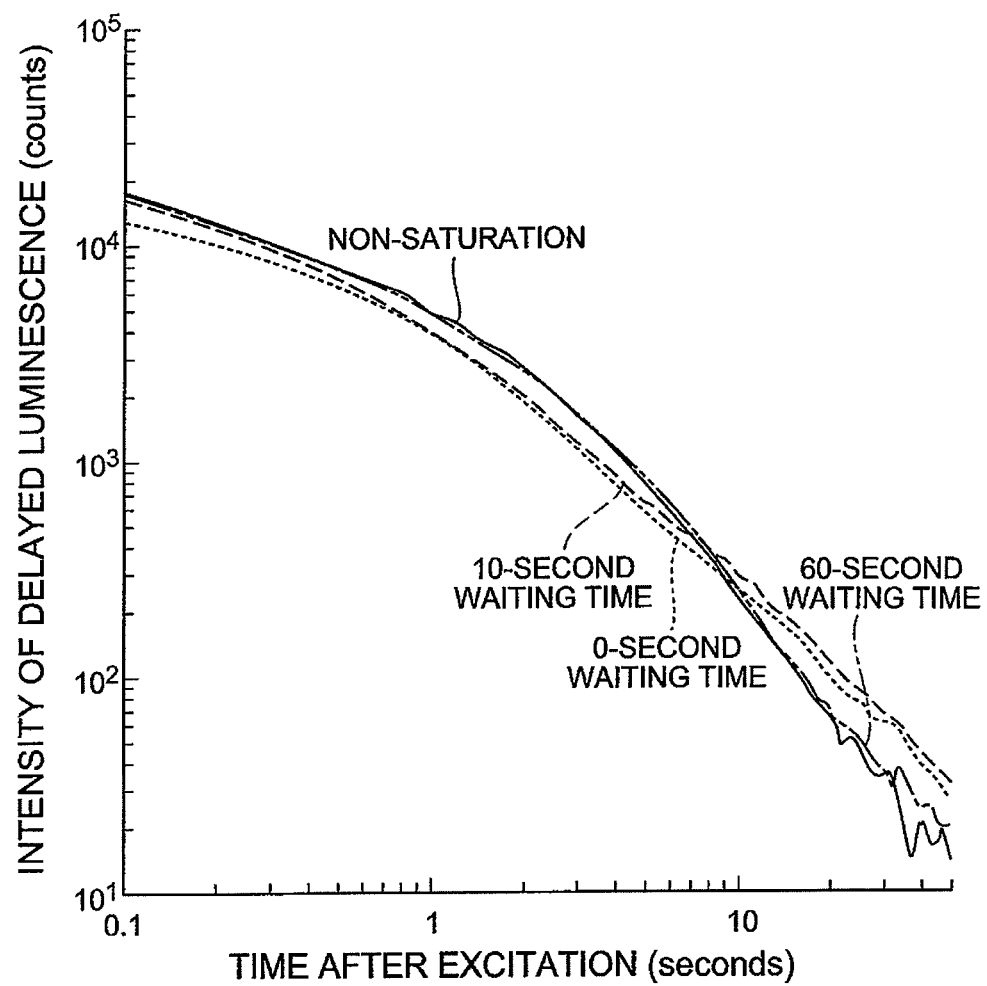
FIG. 36 is a graph of temporal variations of the luminescence amount of delayed luminescence of a DCMU-exposed sample in the example.
Figure 37:
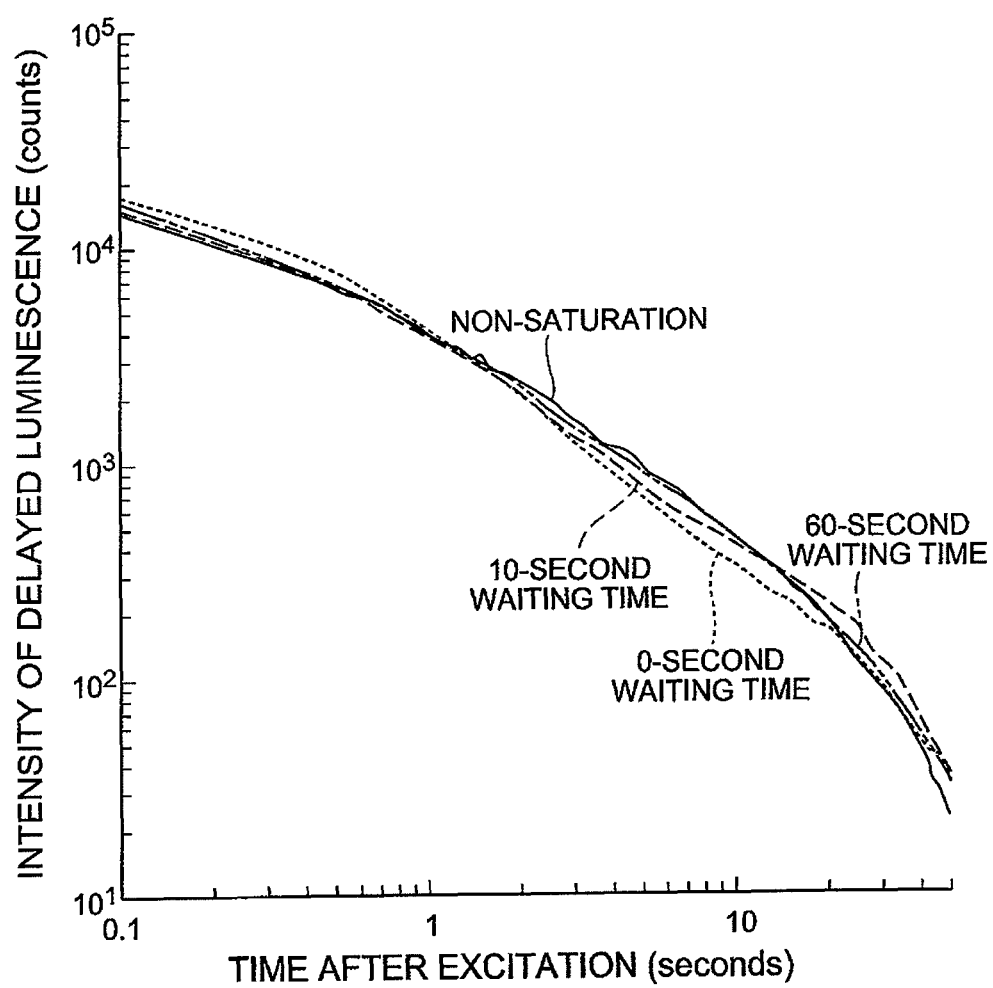
FIG. 37 is a graph of temporal variations of the luminescence amount of delayed luminescence of a DBMIB-exposed sample in the example.
Figure 38:
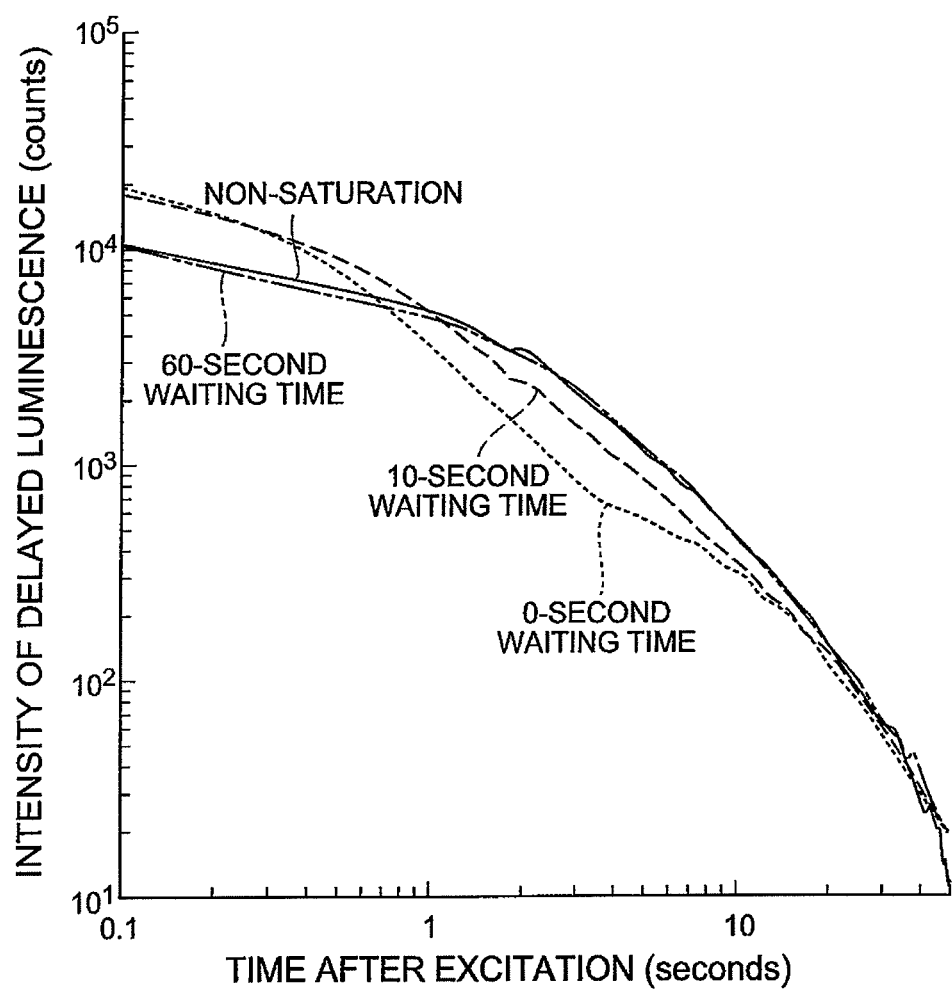
FIG. 38 is a graph of temporal variations of the luminescence amount of delayed luminescence of an Ant-A-exposed sample in the example.

An evaluation program for photosynthetic sample (hereinafter referred to simply as "evaluation program") 50 according to an embodiment shall now be described using FIGS. 33 and 34. FIG. 33 is a diagram showing a configuration of the evaluation program 50 according to the present embodiment along with a storage medium 60. FIG. 34 is a diagram of a hardware configuration of a computer 70 on which the evaluation program 50, shown in FIG. 33, operates.

By the evaluation program 50 operating in cooperation with the computer 70, the computer 70 is enabled to operate as the delayed luminescence measuring device 1. The above-described evaluations of a photosynthetic sample can thereby be realized on the computer 70.

As shown in FIG. 33, the evaluation program 50 includes a light source control module 51, a detection control module 52, and a computing module 53. The light source control module 51 corresponds to the light source controller 31, the detection control module 52 corresponds to the detection controller 32, and the computing module 53 corresponds to the computing unit 22. That is, the computer 70 is made to function as a first excitation unit and a second excitation unit by the light source control module 51, the computer 70 is made to function as a measuring unit by the detection control module 52, and the computer 70 is made to function as an evaluating unit by the computing module 53.

As shown in FIG. 34, the computer 70 is constituted of a CPU 71, executing an operating system and application program, etc., a main storage device 72, in turn constituted of a ROM and a RAM, an auxiliary storage device 73, in turn constituted of a hard disk, etc., a communication controller 74, such as a network card, etc., an output device 76, such as a monitor, printer, etc., and an input device 75, such as a keyboard and mouse, etc. The respective modules described with FIG. 33 are realized by a making a predetermined software be read into the CPU 71 and the main storage device 72 shown in FIG. 34, making the communication controller 74 operate under control by the CPU 71, and performing reading and writing of data from and into the main storage device 72 and the auxiliary storage device 73.

Because with the evaluation program 50, a luminescence amount of delayed luminescence can be measured for each of second illumination conditions that differ, more detailed evaluation values can be derived. Consequently, a redox state of a photosynthetic sample contained in an evaluation sample can be evaluated appropriately and easily.

Example 1

The present invention shall now be described more specifically based on an example. However, the present invention is not restricted to the following example.

A green algae was used as a photosynthetic sample. 2.5 mL of a cell suspension, prepared by adjusting to a 685 nm absorbance OD685 of 0.05 using the C (75) medium as a diluent and thereafter culturing for 1 hour under an environment of 25° C.±1° C. air temperature while illuminating white light of 50 μmol·m−2·s−1, was used as a standard sample. As evaluation samples, a sample exposed to 3-(3,4-dichlorophenyl)-1,1-dimethyl-urea (DCMU) at a concentration of 12 ug/L, a sample exposed to 2,5-dibromo-6-isopropyl-3-methyl-1,4-benzoquinone (DBMIB) at a concentration of 322 μg/L, and a sample exposed to Antimycin A (Ant-A) at a concentration of 0.55 mg/L were prepared. These chemical substances are all inhibitors of photosynthetic electron transport. The samples exposed to DCMU, DBMIB, and Ant-A shall hereinafter be referred to as the DCMU-exposed sample, the DBMIB-exposed sample, and the Ant-A-exposed sample, respectively. For each of the standard sample and the three types of exposed samples, the above-described evaluation method was carried out for the respective conditions of non-saturation, 0-second waiting time, 10-second waiting time, and 60-second waiting time. The redox state of the photosynthetic sample differs among these conditions.

FIGS. 35 to 38 are graphs of temporal variations (decay curves) of the luminescence amount of delayed luminescence determined respectively for the standard sample, the DCMU-exposed sample, the DBMIB-exposed sample, and the Ant-A-exposed sample of the example. As shown in FIGS. 35 to 38, by exposure of a chemical substance, the shape of the decay curve changed with each exposed sample.

Figure 39:
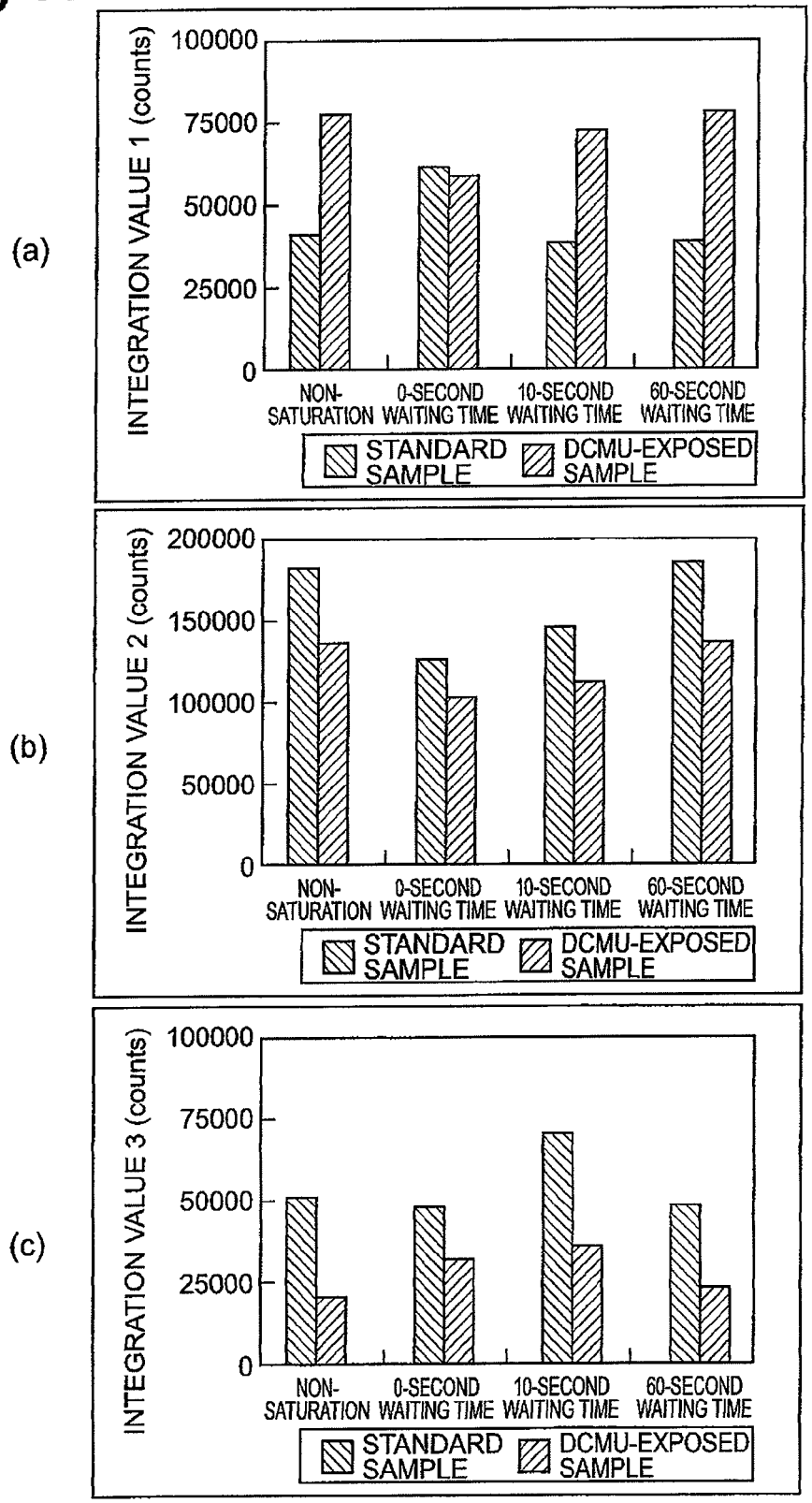
FIG. 39 shows graphs comparing integration values of the standard sample and integration values of the DCMU-exposed sample in the example, with FIG. 39A being a graph of the integration value 1, FIG. 39B being a graph of the integration value 2, and FIG. 39C being a graph of the integration value 3.
Figure 40:
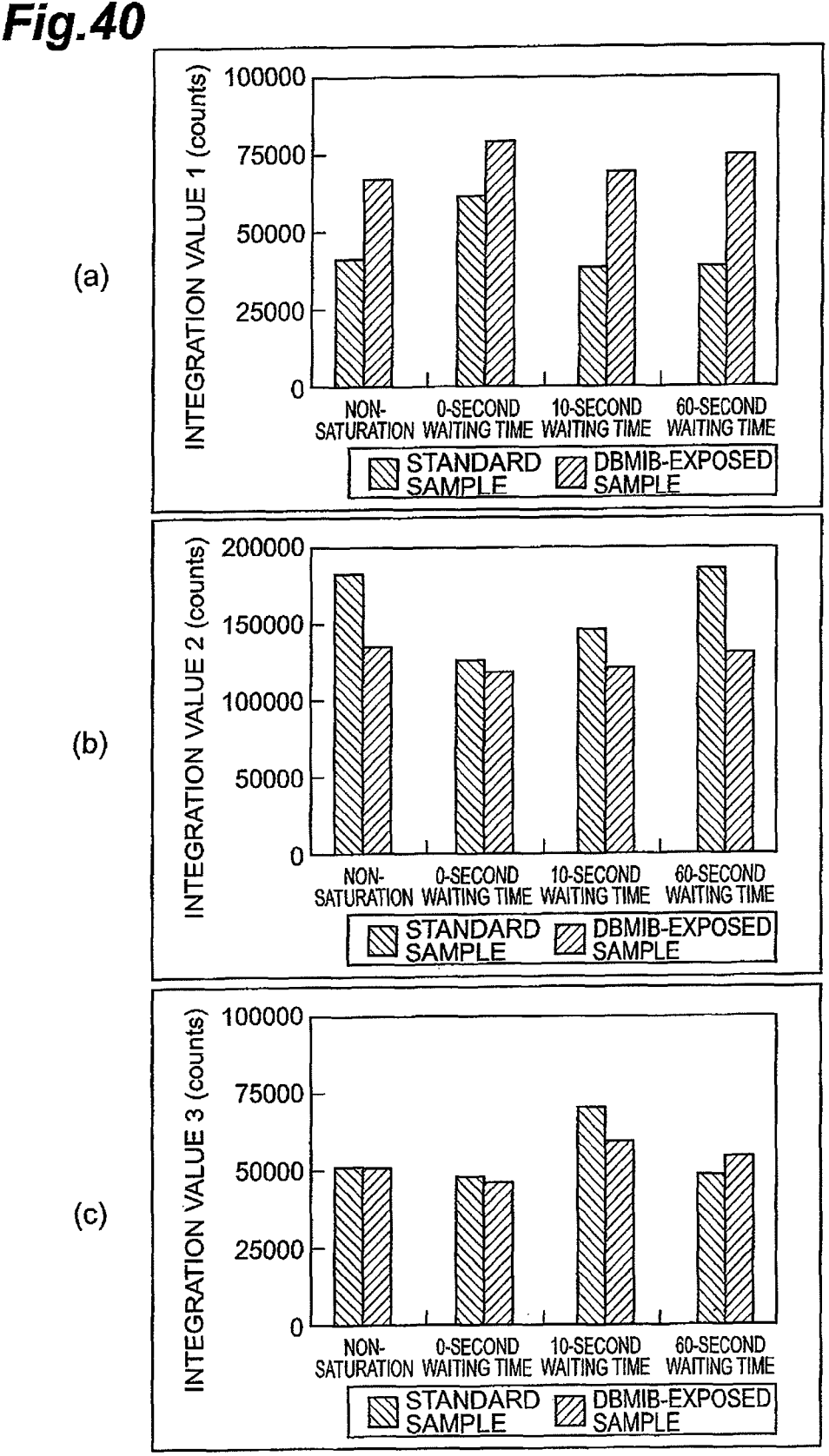
FIG. 40 shows graphs comparing integration values of the standard sample and integration values of the DBMIB-exposed sample in the example, with FIG. 40A being a graph of the integration value 1, FIG. 40B being a graph of the integration value 2, and FIG. 40C being a graph of the integration value 3.
Figure 41:
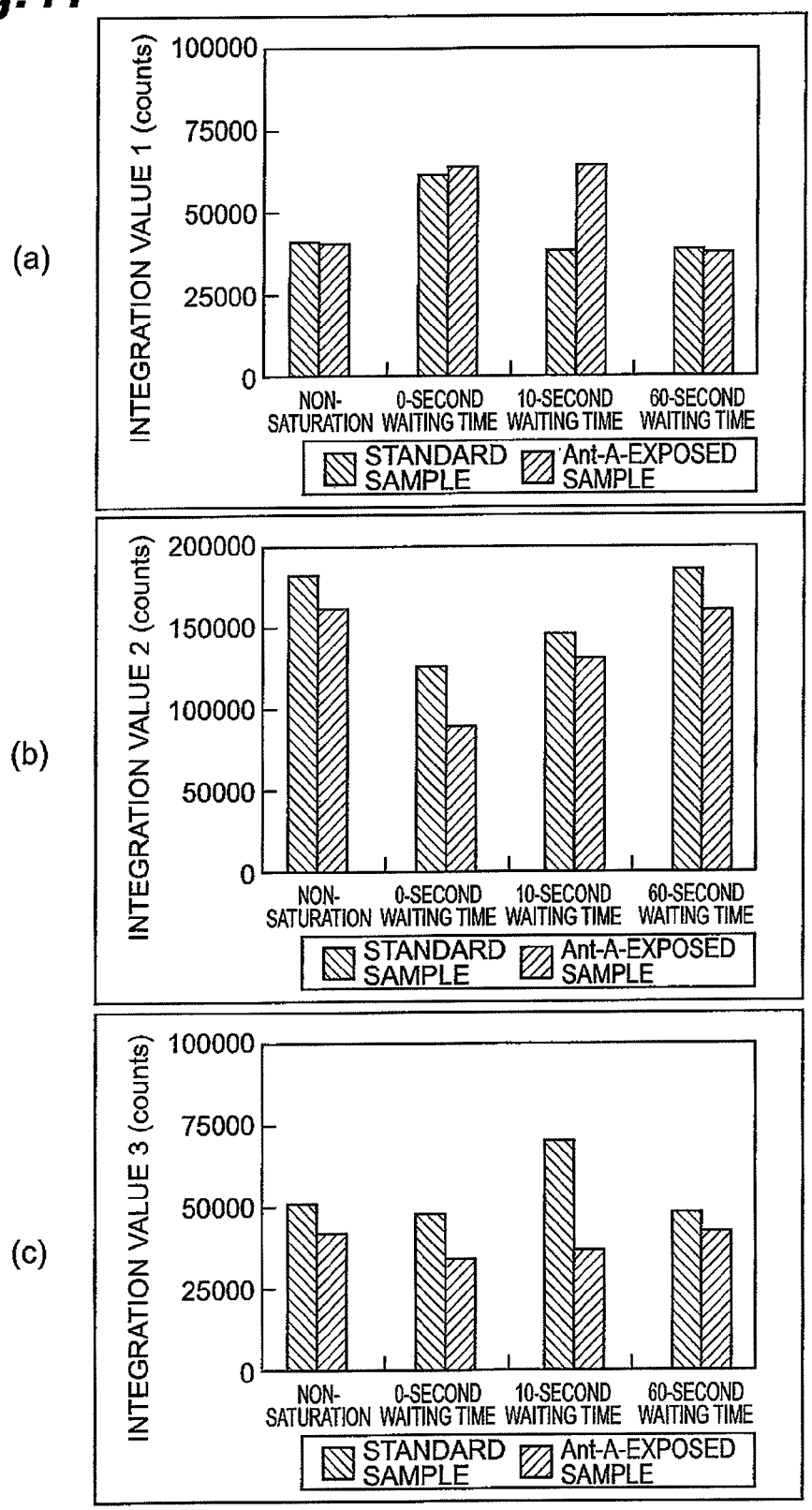
FIG. 41 shows graphs comparing integration values of the standard sample and integration values of the Ant-A-exposed sample in the example, with FIG. 41A being a graph of the integration value 1, FIG. 41B being a graph of the integration value 2, and FIG. 41C being a graph of the integration value 3.

The shape changes of the decay curves shall now be described in detail using integration values. For this description, FIGS. 39 to 41 shall be used. FIG. 39 shows graphs comparing integration values of the standard sample and integration values of the DCMU-exposed sample in the example with FIGS. 39A, 39B, and 39C being graphs concerning the integration value 1, the integration value 2, and the integration value 3, respectively. FIG. 40 shows graphs comparing integration values of the standard sample and integration values of the DBMIB-exposed sample in the example with FIGS. 40A, 40B, and 40C being graphs concerning the integration value 1, the integration value 2, and the integration value 3, respectively. FIG. 41 shows graphs comparing integration values of the standard sample and integration values of the Ant-A-exposed sample in the example with FIGS. 41A, 41B, and 41C being graphs concerning the integration value 1, the integration value 2, and the integration value 3, respectively.

First, results of the standard sample used in common for the respective exposed samples shall be described. With the integration value 1 that reflects the electrons inside the PSII, whereas a maximum value was indicated in the 0-second waiting time case, values approximately equal to that of the non-saturation case were exhibited in the 10-second waiting time and the 60-second waiting time cases. This is due, as mentioned above, to there being a large amount of the reduced plastoquinone being present in the pQ pool immediately after the first excitation light illumination and the electron accumulation in the PSII being increased due to the lessening of the oxidized plastoquinone that can take out electrons from the PSII. For the 10-second and 60-second waiting time cases, it can be understood that recovery to a state equivalent to the non-saturation state where the electron transport reaction of the PSII proceeds smoothly is achieved by formation of the oxidized plastoquinone during the waiting time.

The integration value 2 that reflects the electrons of the pQ pool exhibits a minimum value in the 0-second waiting time case and gradually approaches the value of the non-saturation case as the waiting time becomes longer. This is because, as mentioned above, immediately after the first excitation light illumination, a large amount of the reduced plastoquinone is present in the pQ pool and the oxidized plastoquinone that can bind to the QB site, which is the plastoquinone binding site inside the PSII, is in shortage. Because the oxidized plastoquinone is formed during the waiting time, recovery to a state equivalent to the non-saturation case was achieved in the 60-second waiting time case.

The integration value 3 that reflects the electrons at the PSI onward took on substantially the same value in the non-saturation, 0-second waiting time, and 60-second waiting time case and increased in value only in the 10-second waiting time case. This is because the electrons accumulated in the ferredoxin and NADPH at the PSI onward are transported via the ferredoxin to the oxidized plastoquinone, and the cyclic electron transport reaction, the reverse reaction via the P700, etc., that give rise to the reduced plastoquinone occurred. Because the reactions indicated by the integration value 3 transits through a larger number of reaction pathways in comparison to the reactions indicated by the integration value 1 or the integration value 2, the luminescence amount becomes higher in the 10-second waiting time case than in the 0-second waiting time case. The integration value 3 recovered to a value equivalent to the non-saturation case in the 60-second waiting time case.

The results unique to the respective exposed samples shall now be described. First, the results of the DCMU-exposed sample shall be described. DCMU inhibits binding of the oxidized plastoquinone to the QB site inside the PSII and thereby inhibits the movement of electrons from the interior of the PSII to the pQ pool. The formation of the reduced plastoquinone is thus inhibited and in the plastoquinone pool, the amount of the oxidized plastoquinone present becomes high. As a result of decrease of the electron accumulation in the plastoquinone pool, the formation of the proton gradient by the cytb6f and the supply of electrons to the photosystem I (PSI) are lowered and lowering of NADPH synthesis occurs.

In the respective cases of non-saturation, 10-second waiting time, and 60-second waiting time, the integration value 1 of the DCMU-exposed sample indicated values nearly twice the values of the standard sample and became higher than the value for the 0-second waiting time case, which is closest to the saturated state among the data concerning the standard sample. Whereas with the standard sample, the integration value 1 became higher with the 0-second waiting time (saturated state) than in the non-saturation state, the results were reversed with the DCMU-exposed sample. Also with the DCMU-exposed sample, the value did not decrease even upon recovery from saturation (in the 10-second and 60-second waiting time cases). From this it can be understood that the takeout of electrons from the interior of the PSII is inhibited regardless of the saturation of electron transport by strong light illumination. This is in agreement with DCMU inhibiting the electron transport of PSII.

It is considered that a significant difference was not seen between the standard sample and the DCMU-exposed sample in the 0-second waiting time case because immediately after the first excitation light illumination, cyclic electron transport and other electron dissipation mechanisms operate inside the PSII.

The integration value 2 of the DCMU-exposed sample took on values less than those of the standard sample under all conditions. However, the trend that the minimum value is exhibited in the 0-second waiting time case and the value gradually approaches the value of the non-saturation case as the waiting time becomes longer was the same as in the results of the standard sample. This indicates that although the electron accumulation in the pQ pool was lowered, the process of reoxidation of the reduced plastoquinone was not inhibited. This is in agreement with DCMU lowering the electron transport to the PSII onward but not inhibiting reactions besides this.

The integration value 3 of the DCMU-exposed sample took on values less than those of the standard sample under all conditions. Furthermore, the integration value 3 of the DCMU-exposed sample took on a higher value for the 0-second and 10-second waiting time than for the non-saturation case. Although increase of the value at the 0-second waiting time, which is not seen with the standard sample, is seen, the trend was basically the same as that of the standard sample. This indicates that although the flow of electrons into the PSII due to reverse reactions from the PSI onward decreased, the reverse flow of electrons from the PSI onward was not inhibited. This is in agreement with DCMU lowering the electron transport to the PSII onward but not inhibiting reactions besides this.

Next, the results of the DBMIB-exposed sample shall be described. DBMIB binds to the plastoquinone binding site of the cytb6f complex and thereby inhibits the oxidation of the reduced plastoquinone. Thus in the pQ pool, the amount of the reduced plastoquinone present increases and the amount of the oxidized plastoquinone present decreases.

The integration value 1 of the DBMIB-exposed sample took on values greater than those of the standard sample under all conditions. However, as with the standard sample, the value of the 0-second waiting time case increased in comparison to the non-saturation case and recovered to be nearly the same as that of the non-saturation case in the 10-second and 60-second waiting time cases. This indicates that although the electron accumulation inside the PSII increased, the takeout of electrons from the PSII was not inhibited in itself. This is in agreement with DBMIB inhibiting the production of the oxidized plastoquinone and the takeout of electrons from the PSII being lowered thereby.

In a comparison of the integration value 2 of the DBMIB-exposed sample and the integration value 2 of the standard sample, a large difference is not seen in the 0-second waiting time case that is closest to the saturated state. However, under the other conditions, (non-saturation, 10-second waiting time, and 60-second waiting time), the integration value 2 of the DBMIB-exposed sample was lower than that of the standard sample. That is, with the DBMIB-exposed sample, the difference between the integration value 2 of the state closest to saturation (0-second waiting time) and the integration value 2 of the non-saturation state lessened. This is because in the non-saturation condition, the pQ pool is put in the reduced state and the amount of the oxidized plastoquinone present in the pQ pool increases regardless of not being illuminated by strong light. This is in agreement with DBMIB inhibiting the oxidation of the reduced plastoquinone but not inhibiting electron transport besides this.

In a comparison of the integration value 3 of the DBMIB-exposed sample and the integration value 3 of the standard sample, a large difference was not seen between the two in the non-saturation, 0-second waiting time, and 60-second waiting time cases. However, in a comparison regarding the 10-second waiting time case, whereas the value increased comparatively largely with the standard sample, the increment of the DBMIB-exposed sample was lower than that of the standard sample. This indicates that the flow of electrons from the PSI onward to the pQ pool decreased. This is in agreement with DBMIB lowering the amount present of the oxidized plastoquinone, which becomes an electron acceptor in the cyclic electron transport that is one of the flow pathways of electrons from the PSI to the plastoquinone.

The results of the Ant-A-exposed sample shall now be described. Ant-A is a chemical substance that inhibits the cyclic electron transport by which electrons are transported to the oxidized plastquinone at the cytb6f via the ferredoxin of the PSI to give rise to the reduced plastoquinone. That is, Ant-A inhibits the reaction of cycling electrons from the PSI to the pQ pool.

In a comparison of the integration value 1 of the Ant-A-exposed sample and the integration value 1 of the standard sample, a large difference was not seen for the non-saturation, 0-second waiting time, and 60-second waiting time cases. Also, the trend that in the 0-second waiting time, the integration value 1 increased with respect to the non-saturation case was the same. However, in noting the 10-second waiting time case, whereas with the standard sample, the integration value 1 decreased to become nearly the same as that of the non-saturation case, with the Ant-A-exposed sample, the integration value 1 was increased in the same manner as in the 0-second waiting time case and decreased to be equivalent to that of the non-saturation case in the 60-second waiting time case. In regard to the interior of the PSII being in a state of high electron accumulation even at the 10-second waiting time, at which the electron accumulation inside the PSII should normally be resolved, it is considered that the takeout of electrons from the PSII was not inhibited but there is a possibility that recovery from saturation was slow or that electrons flowed into the PSII from a different pathway.

The integration value 2 of the Ant-A-exposed sample took on values less than those of the standard sample under all conditions. However, the trend that the minimum value is exhibited in the 0-second waiting time case and the value gradually approaches the value of the non-saturation case as the waiting time becomes longer was the same as in the results of the standard sample. This indicates that although the oxidized plastoquinone is decreased in comparison to the standard sample (the pQ pool is in the reduced state), the production of the oxidized plastoquinone at the cytb6f is not inhibited. This is in agreement with Ant-A not inhibiting the production of the oxidized plastoquinone at the cytb6f The integration value 3 of the Ant-A-exposed sample took on values less than those of the standard sample under all conditions. Also, the increase of the integration value 3 at the 10-second waiting time, which was observed with the standard sample, was not observed. Because as mentioned above, it is considered that the cyclic electron transport is involved in the increase of the integration value 3 at the 10-second waiting time, this result can be said to express the decrease of electron accumulation at the PSI onward and the inhibition of the flow of electrons from the PSI to the pQ pool. The inhibition of the flow of electrons from the PSI to the pQ pool is in agreement with Ant-A inhibiting the cyclic electron transport. The decrease of the electron accumulation in PSII is also considered to be caused by decrease of the electrons flowing into the PSI again from pQ pool due to inhibition of the cyclic electron transport. There is also the possibility that electrons, having nowhere to go due to the inhibition of the cyclic electron transport, moved into the PSII by some mechanism and caused the above-mentioned increase of the integration value 1 at the 10-second waiting time.

The values eII, vII, vQ, % oQ, eI, and cI, obtained by carrying out the above-described evaluation value computing methods based on the measured values of the standard sample and the respective exposed samples of the example shall now be described with reference to FIGS. 42 to 44. FIG. 42 is a table of the values eII and vII of the non-saturation cases of the respective samples. FIG. 43 is a table of the values vQ and % oQ of the respective samples. FIG. 44 is a table of the values eI and cI of the non-saturation cases of the respective samples.

As shown in FIG. 42, because the value eII in the non-saturation state of the DCMU-exposed sample is 188, it can be understood that the electron accumulation in the PSII increased in comparison to the standard sample. Because the vII of the DCMU-exposed sample is negative, it can be understood that there is no takeout of electrons from the PSII and that, oppositely, electrons are flowing into the PSII. This is in agreement with the action of DCMU of inhibiting the takeout of electrons from the PSII and thereby increasing the electron accumulation at the PSII.

As shown in FIG. 43, the value vQ was 30 for the DBMIB-exposed sample. This indicates that the redox reaction due to light illumination decreased in comparison to the standard sample. Also, in regard to the value % oQ, whereas with the standard sample, the value was 36 for the 10-second waiting time and 107 for the 60-second waiting time, with the DBMIB-exposed sample, the value was 4 for the 10-second waiting time and 22 for the 60-second waiting time and thus decreased in comparison to the standard sample. This indicates that with the DBMIB-exposed sample, the redox reaction of the pQ pool was lowered and the reoxidation of the plastoquinone by the cytb6f was lowered in comparison to the standard sample. This is in agreement with the action of DBMIB of inhibiting the reoxidation reaction of the plastoquinone at the cytb6f.

As shown in FIG. 44, the value eI for the non-saturation case was 89 for the Ant-A-exposed sample, thus indicating that the electron accumulation in the PSI is not that much lessened in comparison to the standard sample. However, whereas the value cI for the 10-second waiting time case was 38 for the standard sample, the value cI for the 10-second waiting time case was −12 for the Ant-A-exposed sample. This indicates that with the Ant-A-exposed sample, although the electron accumulation in the PSI did not change much, the flow of electrons by the cyclic electron transport, etc., from the PSI into the pQ pool was lowered. This is in agreement with the function of Ant-A of inhibiting the cyclic electron transport.

From the measurement results using DCMU, DBMIB, and Ant-A it can be understood that by measuring the delayed luminescence of photosynthetic samples in different redox states for a standard sample that is not exposed to a harmful substance and exposed samples that are exposed to the harmful substances and comparing the measurement results, the presence/non-presence of a harmful substance and differences in actions on the photosynthetic electron transport reactions can be evaluated. Such a characteristic is useful for evaluation of impacts of a harmful substance on an algae or other photosynthetic sample as represented by ecological risk evaluation of chemical substances.

The present invention has been described above in detail based on the embodiment thereof. However, the present invention is not restricted to the above embodiment. With the present invention, various modifications, such as those given below are possible within a range not falling outside the gist thereof.

Although in the above-described embodiment, evaluation values were derived based on integration values obtained by integrating the measured luminescence amount of delayed luminescence according to measurement time periods, the method for deriving an evaluation value is not restricted thereto. For example, a plurality of functions may be set in advance and coefficient values of the functions may be determined to fit the temporal data (decay curve) of the luminescence amount of delayed luminescence as a sum of the functions, and an evaluation value can be derived based on the coefficient values thus determined.

A method for fitting the temporal data of the luminescence amount of delayed luminescence to temporal data functions (referred to hereinafter as "fitting method") shall now be described in detail. To use the fitting method, information on a plurality of functions is stored in advance in the recording unit 21 of the delayed luminescence measuring device 1. Preferably, hill-shaped functions are used as the functions. A hill-shaped function is a function with a hill-like shape with which the function value takes on a maximum value at a specific variable value and is monotonously non-decreasing at variable values no more than the specific variable value and monotonously non-increasing at variable values no less than the specific variable value.

As the functions, Lorentz functions (Cauchy distributions), each having the following form:

[Mathematical Formula 8]

$$10^{\frac{c_1}{1+a_1(t-b_1)^2}}, 10^{\frac{c_2}{1+a_2(t-b_2)^2}}, 10^{\frac{c_3}{1+a_3(t-b_3)^2}} \quad (3)$$

with $a_i$, $b_i$, and $c_i$ (i=1, 2, 3) being coefficient values of the functions and t being a variable indicating an elapsed time from a base time (time after excitation), may be used. The coefficient value ai influences a spread in a time direction, the coefficient value bi influences the time t after excitation at which the luminescence amount takes on a maximum value, and the coefficient value ci influences a peak value of the maximum value.

In this case, the sum of the functions used for fitting is expressed as follows:

[Mathematical Formula 9]

$$fm(t) = 10^{\frac{c_1}{1+a_1(t-b_1)^2}} + 10^{\frac{c_2}{1+a_2(t-b_2)^2}} + 10^{\frac{c_3}{1+a_3(t-b_3)^2}} \quad (4)$$

Here, the base time of the time t after excitation is, for example, set to a time after elapse of a prescribed time set in advance from a time at which the illumination of light from the light source 12 is ended. In Formula (4), a first term, a second term, and a third term at the right hand side are respectively orders of appearance of the maximum value along the time axis and are expressed as a first function, a second function, and a third function. That is, with the coefficients of the functions, a relationship: b1<b2<b3 holds.

The functions used in the fitting method are not restricted to the above, and quadratic functions, normal distribution functions, and other hill-shaped functions besides the above may be used. Also, as long as the functions fit well, the functions do not have to be hill-shaped functions. Furthermore, functions, expressed by the following formula with which coefficients di (i=1, 2, 3) are added to the functions of Formula (4), may be used instead.

[Mathematical Formula 10]

$$fm(t) = 10^{\frac{c_1}{1+a_1(t-b_1)^{d_1}}} + 10^{\frac{c_2}{1+a_2(t-b_2)^{d_2}}} + 10^{\frac{c_3}{1+a_3(t-b_3)^{d_3}}} \quad (5)$$

To carry out the fitting method, an algorithm for performing fitting is also stored in advance in the recording unit 21. For example, a simplex method, Gauss-Newton method, Davidon Fletcher Powell method, Brent's method, Monte Carlo method, simulated annealing method, etc., may be used as the algorithm for performing fitting.

An evaluation value is then derived based on the coefficient values computed by the fitting method. For example, the evaluation value is computed based on a formula for computing the evaluation value stored in advance in the recording unit 21.

By using such a fitting method, it becomes possible to derive an evaluation value objectively. Also, because the temporal variation of the luminescence amount of delayed luminescence is fitted, for example, to the formula indicated as Formula (4) or the formula indicated as Formula (5) above, an evaluation based on the mechanism of delayed luminescence, described using FIG. 19, etc., is made possible. The redox state of a photosynthetic sample contained in an evaluation sample can thus be evaluated appropriately.

Although with the embodiment described above, the waiting time is employed as the second illumination condition that is changed in repeating the measurement of the luminescence amount of delayed luminescence a plurality of times, the second illumination condition that is changed is not restricted thereto. Because the redox state of a photosynthetic sample depends on the energy of light illuminated onto the photosynthetic sample and the efficiency of electron transport of the photosynthetic sample, for example, at least one of a light amount, wavelength, pulse width, and illumination duration of the second excitation light may be changed. These conditions related to the second excitation light are closely related to changes of the redox state of the photosynthetic sample described using FIG. 19, etc. Thus by repeating illumination of the first excitation light and illumination of the second excitation light a plurality of times while changing at least one of these elements and deriving an evaluation value based on the respective luminescence amounts measured, the redox state of the photosynthetic sample contained in the evaluation sample can be evaluated appropriately.

Also, a temperature, electric field or other environmental factor, by which the electron transport efficiency of a photosynthetic sample changes, may be employed as a load factor. Light illumination conditions, darkness conditions, temperature conditions, electric field conditions, magnetic field conditions, pH conditions, etc., can be cited as load conditions and a plurality of redox states can also be realized using these load conditions. The redox state of the photosynthetic sample contained in the evaluation sample can thus be evaluated appropriately.

For example, a temperature condition may be employed in place of the first illumination condition and the waiting time in the above-described embodiment. Because temperature influences a transport rate of the electron transport system, electron transport in a photosynthetic sample is more promoted the higher the temperature. Thus by controlling the temperature condition loaded on an evaluation sample, states differing in the redox state of the photosynthetic sample contained in the evaluation sample can be realized in a stepwise manner.

A darkness condition may be employed in place of the first illumination condition and the waiting time in the above-described embodiment. Under a darkness condition, a photosynthetic function enters a dormant state and a photosynthetic electron transport efficiency of a photosynthetic sample becomes lowered. Although as the darkness condition becomes longer, the amount of lowering increases, the change stops when a certain period is reached. Although there are differences according to measurement conditions, as one example, when delayed luminescence is measured upon placing the photosynthetic sample in darkness, lowering of the delayed luminescence amount is seen at 10 seconds and later after excitation. Furthermore, when the length of the darkness condition reaches a certain period, the lowering of the luminescence amount stops and becomes fixed.

Ultraviolet rays may be employed as a light illumination condition in place of the first illumination condition and the waiting time in the above-described embodiment. Although ultraviolet rays inflict damage on a photosynthetic function, a magnitude of the influence varies according to wavelength and irradiation amount (irradiation strength×irradiation strength). The shorter the wavelength and higher the irradiation amount, the greater the load (stress) on a photosynthetic sample, and the photosynthetic sample becomes lowered in electron transport efficiency.

A pH condition may be employed in place of the first illumination condition and the waiting time in the above-described embodiment. The pH mainly influences the formation of the proton gradient with which the hydrogen ion concentration becomes high at a mitochondrial inner membrane, which is involved in a respiratory chain inside cell, and inside the thylakoid membrane of the chloroplast, which is related to the photosynthetic electron transport system. The magnitude of influence on algae is made apparent in that when the difference between the pH of an algae cell suspension (culture solution) and the pH inside the thylakoid membrane of the photosynthetic sample (the algae used) becomes low, the load (stress) on the photosynthetic sample becomes high. Also, an extremely high or low pH becomes a physical stress for the photosynthetic sample.

These load conditions may be used in combination. By applying a load by a plurality of load conditions to a photosynthetic sample, states differing in the redox state of the photosynthetic sample can be realized in a stepwise manner.

In the present invention, characteristic values refer to values that indicate characteristics of a plurality of time periods in temporal data of a luminescence amount of delayed luminescence emitted from a photosynthetic sample. One characteristic value or a plurality of characteristic values may be computed for each time period. As examples of the characteristic values, integration values of the luminescence amount of delayed luminescence, determined by integration according to each of one or more measurement time periods, coefficient values, obtained by fitting a temporal variation of the luminescence amount of delayed luminescence as a sum of functions, can be cited.

An evaluation value is a value for evaluating a state of a photosynthetic sample and is computed by weighting the characteristic values. Here, by the weighting, a characteristic value of a high degree of importance with respect to an evaluation condition is made high in its influence on an evaluation value. If a characteristic value of a low degree of importance with respect to an evaluation condition is known, weighting such that this characteristic value is not used in the computation of the corresponding evaluation value may be applied. Oppositely, if a characteristic value of an especially high degree of importance with respect to an evaluation condition is known, weighting such that other characteristic values are not used in the computation of the corresponding evaluation value may be applied.

Reference data refer to the basic data or the standard data in the above-described embodiments.

A second photosynthetic sample is a photosynthetic sample for acquiring the reference data and, with respect to the photosynthetic sample to be evaluated, differs in at least one of either an environment condition (addition of a harmful substance or temperature, etc.,) and a condition (growth condition, etc.,) of the photosynthetic sample itself. Although use of a photosynthetic sample that is not exposed to an environmental factor is preferable as the second photosynthetic sample, the present invention is not restricted thereto.

The invention claimed is:

1. An evaluation method for evaluating a state of a photosynthetic sample with a photosynthetic function based on temporal data of a luminescence amount of delayed luminescence emitted from the photosynthetic sample, method performed on a hardware processor of a computer and comprising:

a characteristic value computing step of computing on the hardware processor, for a plurality of time periods in the temporal data, characteristic values that indicate characteristics for predefined functions that represent timely evolution of luminescence resulting from different reactions in the photosynthetic sample;

an evaluation value computing step of computing on the hardware processor an evaluation value by weighting the characteristic values; and an evaluation step of evaluating on the hardware processor the state of the photosynthetic sample based on the evaluation value by determining a degree of impact of the different reactions in the photosynthetic sample to decide whether the different reactions are harmful or not, wherein the characteristic value computing step comprises a fitting step of determining, as the characteristic values, coefficient values of the predefined functions so that the temporal data are fitted as a sum of the functions, in the evaluation value computing step, the evaluation value is computed based on the coefficient values determined in the fitting step, and the evaluation value is an area value computed based on coefficient values of at least one function among the plurality of functions, the predetermined functions are hill-shaped Lorentz functions, and when $a_i$, $b_j$, and $c_j$ ($i=1, 2, 3$) are the coefficient values of the plurality of functions and t is a variable indicating an elapsed time from a base time, the predetermined functions are respectively expressed as the following mathematical formulas:

$$10^{\frac{c_1}{1+a_1(t-b_1)^2}},$$

$$10^{\frac{c_2}{1+a_2(t-b_2)^2}}, \text{ and}$$

$$10^{\frac{c_3}{1+a_3(t-b_3)^2}}.$$

2. An evaluation method for evaluating a state of a photosynthetic sample with a photosynthetic function based on temporal data of a luminescence amount of delayed luminescence emitted from the photosynthetic sample, method performed on a hardware processor of a computer and comprising:

a characteristic value computing step of computing on the hardware processor, for a plurality of time periods in the temporal data, characteristic values that indicate characteristics for predefined functions that represent timely evolution of luminescence resulting from different reactions in the photosynthetic sample;

an evaluation value computing step of computing on the hardware processor an evaluation value by weighting the characteristic values;

an evaluation step of evaluating on the hardware processor the state of the photosynthetic sample based on the evaluation value by determining a degree of impact of the different reactions in the photosynthetic sample to decide whether the different reactions are harmful or not; and a measuring step of measuring the luminescence amount with time of the delayed luminescence emitted from the photosynthetic sample and making the measurement data the temporal data, wherein the measuring step further comprises a first excitation step of illuminating a first excitation light onto the photosynthetic sample under a predetermined first illumination condition; and a second excitation step of illuminating, after the first excitation step, a second excitation light onto the photosynthetic sample under a second illumination condition that is less in light energy integration value than the first illumination condition;

in the characteristic value computing step, the characteristic values are computed based on temporal data obtained after the second excitation step, and the predetermined functions are hill-shaped Lorentz functions, and when $a_i$, $b_i$, and $c_i$ (i=1, 2, 3) are the coefficient values of the plurality of functions and t is a variable indicating an elapsed time from a base time, the predetermined functions are respectively expressed as the following mathematical formulas:

$$10^{\frac{c_1}{1+a_1(t-b_1)^2}},$$

$$10^{\frac{c_2}{1+a_2(t-b_2)^2}}, \text{ and}$$

$$10^{\frac{c_3}{1+a_3(t-b_3)^2}}.$$

3. The evaluation method for photosynthetic sample according to claim 2, wherein in the measuring step, a plurality of sets of temporal data are acquired by repeatedly measuring the luminescence amount a plurality of times with the second illumination condition being changed.

4. The evaluation method for photosynthetic sample according to claim 3, wherein the second illumination condition is a waiting time from an illumination ending time of the first excitation light to an illumination starting time of the second excitation light.

5. The evaluation method for photosynthetic sample according to claim 3, wherein the second illumination condition is at least one condition selected from the group consisting of a light amount, wavelength, pulse width, and illumination duration of the second excitation light.

6. An evaluation method for evaluating a state of a photosynthetic sample with a photosynthetic function based on temporal data of a luminescence amount of delayed luminescence emitted from the photosynthetic sample, method performed on a hardware processor of a computer and comprising:

a characteristic value computing step of computing on the hardware processor, for a plurality of time periods in the temporal data, characteristic values that indicate characteristics for predefined functions that represent timely evolution of luminescence resulting from different reactions in the photosynthetic sample;

an evaluation value computing step of computing on the hardware processor an evaluation value by weighting the characteristic values; and an evaluation step of evaluating on the hardware processor the state of the photosynthetic sample based on the evaluation value by determining a degree of impact of the different reactions in the photosynthetic sample to decide whether the different reactions are harmful or not, wherein the evaluation step further comprises a comparing step of comparing the evaluation value computed in the evaluation value computing step and reference data on the evaluation value, the predetermined functions are hill-shaped Lorentz functions, and when $a_i$, $b_i$, and $c_i$ (i=1, 2, 3) are the coefficient values of the plurality of functions and t is a variable indicating an elapsed time from a base time, the predetermined functions are respectively expressed as the following mathematical formulas:

$$10^{\frac{c_1}{1+a_1(t-b_1)^2}},$$

$$10^{\frac{c_2}{1+a_2(t-b_2)^2}}, \text{ and}$$

$$10^{\frac{c_3}{1+a_3(t-b_3)^2}}.$$

7. The evaluation method for photosynthetic sample according to claim 6 further comprising:

a reference data generating step of measuring the luminescence amount with time of the delayed luminescence emitted from a second photosynthetic sample and deriving, from the measurement data, the reference data used in the comparing step.

8. An evaluation method for evaluating a state of a photosynthetic sample with a photosynthetic function based on temporal data of a luminescence amount of delayed luminescence emitted from the photosynthetic sample, method performed on a hardware processor of a computer and comprising:

a characteristic value computing step of computing on the hardware processor, for a plurality of time periods in the temporal data, characteristic values that indicate characteristics for predefined functions that represent timely evolution of luminescence resulting from different reactions in the photosynthetic sample;

an evaluation value computing step of computing on the hardware processor an evaluation value by weighting the characteristic values; and an evaluation step of evaluating on the hardware processor the state of the photosynthetic sample based on the evaluation value by determining a degree of impact of the different reactions in the photosynthetic sample to decide whether the different reactions are harmful or not, wherein in the evaluation step, an environmental factor to which the photosynthetic sample is subjected to by the different reactions is evaluated, the predetermined functions are hill-shaped Lorentz functions, and when $a_i$, $b_i$, and $c_i$ (i=1, 2, 3) are the coefficient values of the plurality of functions and t is a variable indicating an elapsed time from a base time, the predetermined functions are respectively expressed as the following mathematical formulas:

$$10^{\frac{c_1}{1+a_1(t-b_1)^2}},$$

$$10^{\frac{c_2}{1+a_2(t-b_2)^2}}, \text{ and}$$

$$10^{\frac{c_3}{1+a_3(t-b_3)^2}}.$$

9. The evaluation method for photosynthetic sample according to claim 8 wherein
the environmental factor is a plant cell growth inhibiting substance.

10. An evaluation system for photosynthetic sample, evaluating a state of a photosynthetic sample with a photosynthetic function based on temporal data of a luminescence amount of delayed luminescence emitted from the photosynthetic sample and comprising:
a characteristic value computing unit, computing, for a plurality of time periods in the temporal data, characteristic values that indicate characteristics for predefined functions that represent timely evolution of luminescence resulting from different reactions in the photosynthetic sample;
an evaluation value computing unit, computing an evaluation value by weighting the characteristic values; and
an evaluating unit, evaluating the state of the photosynthetic sample based on the evaluation value by determining a degree of impact of the different reactions in the photosynthetic sample to decide whether the different reactions are harmful or not,
wherein the characteristic value computing unit comprises a fitting transmit for determining, as the characteristic values, coefficient values of the predefined functions so that the temporal data are fitted as a sum of the functions,
in the evaluation value computing unit, the evaluation value is computed based on the coefficient values determined in the fitting unit, and the evaluation value is an area value computed based on coefficient values of at least one function among the plurality of functions,
the predefined functions are hill-shaped Lorentz functions, and
when $a_i$, $b_i$, and $c_i$ (i=1, 2, 3) are the coefficient values of the plurality of functions and t is a variable indicating an elapsed time from a base time, the predetermined functions are respectively expressed as the following mathematical formulas:

$$10^{\frac{c_1}{1+a_1(t-b_1)^2}},$$

$$10^{\frac{c_2}{1+a_2(t-b_2)^2}}, \text{ and}$$

$$10^{\frac{c_3}{1+a_3(t-b_3)^2}}.$$

11. The evaluation system for photosynthetic sample according to claim 10, further comprising:
a measuring unit, measuring the luminescence amount with time of the delayed luminescence emitted from the photosynthetic sample and making the measurement data the temporal data.

12. The evaluation system for photosynthetic sample according to claim 11 further comprising:
a light source controller, controlling a light source so as to illuminate excitation light onto the photosynthetic sample while changing illumination conditions.

13. The evaluation system for photosynthetic sample according to claim 10, wherein
the evaluating unit evaluates an environmental factor to which the photosynthetic sample is subjected.

14. A non-transitory computer readable medium having an evaluation program recorded thereon, the evaluation program configured for performing a method that makes a hardware computer evaluate a state of a photosynthetic sample with a photosynthetic function based on temporal data of a luminescence amount of delayed luminescence emitted from the photosynthetic sample when executed on said hardware computer, the method comprising:
a characteristic value computing step of computing, for a plurality of time periods in the temporal data, characteristic values that indicate characteristics for predefined functions that represent timely evolution of luminescence resulting from different reactions in the photosynthetic sample;
an evaluation value computing step of computing an evaluation value by weighting the characteristic values; and
an evaluating step of evaluating the state of the photosynthetic sample based on the evaluation value by determining a degree of impact of the different reactions in the photosynthetic sample to decide whether the different reactions are harmful or not,
wherein the characteristic value computing step comprises a fitting step for determining as the characteristic values, coefficient values of the predefined functions so that the temporal data are fitted as a sum of the functions,
in the evaluation value computing step, the evaluation value is computed based on the coefficient values determined in the fitting step, and the evaluation value is an area value computed based on coefficient values of at least one function among the plurality of functions,
the predefined functions are hill-shaped Lorentz functions, and
when $a_i$, $b_i$, and $c_i$ (i=1, 2, 3) are the coefficient values of the plurality of functions and t is a variable indicating an elapsed time from a base time, the predetermined, functions are respectively expressed as the following mathematical formulas:

$$10^{\frac{c_1}{1+a_1(t-b_1)^2}},$$

$$10^{\frac{c_2}{1+a_2(t-b_2)^2}}, \text{ and}$$

$$10^{\frac{c_3}{1+a_3(t-b_3)^2}}.$$

15. The non-transitory computer readable medium according to claim 14, the method further comprising:
a measuring step of measuring the luminescence amount with time of the delayed luminescence emitted from the photosynthetic sample and making the measurement data the temporal data.

16. The non-transitory computer readable medium according to claim 15, wherein
in the measuring step, a first excitation step of illuminating a first excitation light onto the photosynthetic sample under a predetermined first illumination condition, and
a second excitation step of illuminating, after the first excitation step, a second excitation light onto the photosynthetic sample under a second illumination condition that is less in light energy integration value than the first illumination condition, are executed and in the characteristic value computing step, the characteristic values are computed based on temporal data obtained after the second excitation step.

17. The non-transitory computer readable medium according to claim 16, wherein in the measuring step, a plurality of sets of temporal data are acquired by repeatedly measuring the luminescence amount a plurality of times with the second illumination condition being changed.

18. The non-transitory computer readable medium according to claim 14, wherein in the evaluating step, an environmental factor to which the photosynthetic sample is subjected is evaluated.

* * * * *

UNITED STATES PATENT AND TRADEMARK OFFICE
CERTIFICATE OF CORRECTION

PATENT NO.       : 8,798,931 B2
APPLICATION NO.  : 12/279789
DATED            : August 5, 2014
INVENTOR(S)      : Masakazu Katsumata et al.

It is certified that error appears in the above-identified patent and that said Letters Patent is hereby corrected as shown below:

Title page, item (73) "Assignee"

change "Hamamatsu Photonics KK." to --Hamamatsu Photonics K.K.--

Signed and Sealed this
Fourth Day of November, 2014

Michelle K. Lee
*Deputy Director of the United States Patent and Trademark Office*